(12) United States Patent
Brulet et al.

(10) Patent No.: US 8,263,821 B2
(45) Date of Patent: Sep. 11, 2012

(54) NON-INVASIVE REAL-TIME IN VIVO BIOLUMINESCENCE IMAGING OF LOCAL CAÂ2+ DYNAMICS IN LIVING ORGANISMS

(75) Inventors: Philippe Brulet, Paris (FR); Kelly Rogers, Paris (FR); Sandrine Picaud, Vincennes (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 11/032,236

(22) Filed: Jan. 11, 2005

(65) Prior Publication Data

US 2005/0273867 A1   Dec. 8, 2005

Related U.S. Application Data

(60) Provisional application No. 60/543,659, filed on Feb. 12, 2004.

(51) Int. Cl.
  *G01N 33/00* (2006.01)
  *A01K 67/00* (2006.01)
  *A01K 67/027* (2006.01)
(52) U.S. Cl. .................. 800/3; 800/8; 800/14; 800/18
(58) Field of Classification Search .................. None
  See application file for complete search history.

(56) References Cited

FOREIGN PATENT DOCUMENTS

| EP | 1226752 | * | 7/2002 |
|---|---|---|---|
| WO | WO 01/92300 | * | 12/2001 |
| WO | WO 01 92300 A2 | | 12/2001 |

OTHER PUBLICATIONS

Waud et al. Biochem. J. 357:687-697, 2001.*
Baubet et al. PNAS 97:7260-7265; 2000.*
Moreadith et al., J. Mol. Med., 1997, 208-216.*
Thomas et al. Nature Rev./Genet. 4: 346-358; 2003.*
Majewska et al. J. Neurosci. 20(22):8262-8268; 2000.*
Gilland et al. PNAS 96:157-161; 1999.*
Pozzan et al. Eur. J. Biochem. 270: 2343-2352; 2003.*
Kerr et al. Neuron 26:583-594; 2000.*
Cherry Phys. Med. Biol. 49:R13-R48; 2004.*
Rogers et al. PloS ONE 2(10), e974:1-15; 2007.*
International Search Report of corresponding PCT/EP05/000817.
Baubet et al.; Chimeric green fluorescent protein-aequorin as bioluminescent CA2+ reporters at the single-cell level; *PNAS*; vol. 97, No. 13 (Jun. 2000) pp. 7260-7265.
Chiesa et al.; Recombinant aequorin and green fluorescent protein as valuable tools in the study of cell signaling, *Biochem J.*, vol. 355 (Oct. 2001) pp. 1-12.
Brownlee, Colin; Cellular calcium imaging: so, what's new?, *Cell Biol.*, vol. 10 (Oct. 2000) pp. 451-457.
Filippin et al.; Stable interactions between mitochondria and endoplasmic reticulum allow rapid accumulation of calcium in a subpopulation of mitochondria, *J. Biol. Chem.*, vol. 278, No. 40 (Oct. 2003) pp. 39224-39234.
Curie et al. "Red-shifted aequorin-based bioluminescent-reporters for in vivo imaging of $Ca^{2+}$ signaling," Molecular Imaging, 6(1): 30-42 (2007).

* cited by examiner

*Primary Examiner* — Sumesh Kaushal
(74) *Attorney, Agent, or Firm* — Finnegan, Henderson, Farabow, Garrett & Dunner, LLP

(57) ABSTRACT

The invention relates to a method for optical detection of the dynamics of $Ca^{2+}$ in a biological system, said method comprising monitoring the photons emitted by a recombinant $Ca^{2+}$-sensitive polypeptide, which comprises or consists of a chemiluminescent protein linked to a fluorescent protein, present in said biological system. In a particular embodiment, said recombinant polypeptide comprises or consists of the Aequorin and GFP linked by a linker allowing chemiluminescence resonance energy transfer (CRET), and optionally comprises a peptidic fragment capable of targeting said recombinant polypeptide into a specific cellular domain or compartment.

The present invention also concerns a transgenic non-human animal expressing said recombinant polypeptide sensitive to calcium concentration, in conditions enabling the in vivo monitoring of $Ca^{2+}$ dynamics. In a particular embodiment, the expression and/or localization of said recombinant polypeptide is restricted to a specific tissue, a single-cell type and/or in a particular cellular compartment or domain.

17 Claims, 29 Drawing Sheets

Plasmid Data Sheet

Plasmid name: PSDGA
Other name: PSDG5A
Insert size: 3660 bp
Inserted gene: PSD95: bases 616-2788
GFP bases: 2842-3555
Aequorin bases: 3706-4275

Vector: pEGFP-C1 (Clontech)
Resistance gene: Kanamycin

616/1
atg gac tgt ctc tgt ata gtg aca acc aag aaa tac cgc tac caa gat gaa gac acg ccc
Met asp cys leu cys ile val thr thr lys lys tyr arg tyr gln asp glu asp thr pro
                                                    646/11

676/21
cct ctg gaa cac agc ccg gcc cac ctc ccc aac cag gcc aat tct ccc cct gtg att gtc
pro leu glu his ser pro ala his leu pro asn gln ala asn ser pro pro val ile val
                                                    706/31

736/41
aac acg gac acc cta gaa gcc cca gga tat gag ttg cag gtg aat gga aca gag ggg gag
asn thr asp thr leu glu ala pro gly tyr glu leu gln val asn gly thr glu gly glu
                                                    766/51

796/61
atg gag tat gag gag atc aca ttg gaa agg ggt aac tca ggt ctg ggc ttc agc atc gca
met glu tyr glu glu ile thr leu glu arg gly asn ser gly leu gly phe ser ile ala
                                                    826/71

856/81
ggt ggc act gac aac ccg cac atc ggt gac gac ccg tcc att ttt atc acc aag atc att
gly gly thr asp asn pro his ile gly asp asp pro ser ile phe ile thr lys ile ile
                                                    886/91

916/101
cct ggt ggg gct gca gcc cag gat ggc cgc ctc agg gtc aat gac agc atc ctg ttt gta
pro gly gly ala ala ala gln asp gly arg leu arg val asn asp ser ile leu phe val
                                                    946/111

976/121
aat gaa gtg gat gtt cgg gag gtg acc cat tca gct gcg gtg gag gcc ctc aaa gag gca
asn glu val asp val arg glu val thr his ser ala ala val glu ala leu lys glu ala
                                                    1006/131

1036/141
ggt tcc atc gtt cgc ctc tat gtc atg cgc cgg aaa ccc cca gcc gaa aag gtc atg gag
gly ser ile val arg leu tyr val met arg arg lys pro pro ala glu lys val met glu
                                                    1066/151

1096/161
atc aaa ctc atc aaa ggg cct aaa gga ctt ggc ttc agc att gcg ggg ggc gtt ggg aac
ile lys leu ile lys gly pro lys gly leu gly phe ser ile ala gly gly val gly asn
                                                    1126/171

1156/181
cag cac atc cct gga gat aac agc atc tat gta acg aag atc atc gaa gga ggt gct gcc
gln his ile pro gly asp asn ser ile tyr val thr lys ile ile glu gly gly ala ala
                                                    1186/191

1216/201
cac aag gat ggc agg ttg cag att gga gac aag atc ctg gcg gtc aac agt gtg ggg ctg
his lys asp gly arg leu gln ile gly asp lys ile leu ala val asn ser val gly leu
                                                    1246/211

1276/221
gag gac gtc atg cac gag gat gcc gtg gca gcc ctg aag aac aca tat gac gtt gtg tac
glu asp val met his glu asp ala val ala ala leu lys asn thr tyr asp val val tyr
                                                    1306/231

1336/241
cta aag gtg gcc aag ccc agc aat gcc tac ctg agt gac agc tat gct ccc cca gac atc
leu lys val ala lys pro ser asn ala tyr leu ser asp ser tyr ala pro pro asp ile
                                                    1366/251

1396/261
aca acc tcg tat tct cag cac ctg gac aat gag atc agt cat agc agc tac ttg ggc act
thr thr ser tyr ser gln his leu asp asn glu ile ser his ser ser tyr leu gly thr
                                                    1426/271

Fig. 11B

```
1456/281                                    1486/291
gac tac ccc aca gcc atg acc ccc act tcc    cct cgg cgc tac tcc cct gtg gcc aag gac
asp tyr pro thr ala met thr pro thr ser    pro arg arg tyr ser pro val ala lys asp 1516/301                                    1546/311
ctg ctg ggg gag gaa gac att ccc cgg gaa    cca agg cgg atc gtg atc cat cgg ggc tcc
leu leu gly glu glu asp ile pro arg glu    pro arg arg ile val ile his arg gly ser 1576/321                                    1606/331
acc ggc ctg ggc ttc aac atc gtg ggc ggc    gag gat ggt gaa ggc atc ttc atc tcc ttc
thr gly leu gly phe asn ile val gly gly    glu asp gly glu gly ile phe ile ser phe 1636/341                                    1666/351
atc ctt gct ggg ggt cca gcc gac ctc agt    ggg gag cta cgg aag ggg gac cag atc ctg
ile leu ala gly gly pro ala asp leu ser    gly glu leu arg lys gly asp gln ile leu 1696/361                                    1726/371
tcg gtc aat ggt gtt gac ctc cgc aat gcc    agt cac gaa cag gct gcc att gcc ctg aag
ser val asn gly val asp leu arg asn ala    ser his glu gln ala ala ile ala leu lys 1756/381                                    1786/391
aat gcg ggt cag acg gtc acg atc atc gct    cag tat aaa cca gaa gag tat agt cga ttc
asn ala gly gln thr val thr ile ile ala    gln tyr lys pro glu glu tyr ser arg phe 1816/401                                    1846/411
gag gcc aag atc cat gat ctt cgg gaa cag    ctc atg aat agt agc cta ggc tca ggg act
glu ala lys ile his asp leu arg glu gln    leu met asn ser ser leu gly ser gly thr 1876/421                                    1906/431
gca tcc ttg cga agc aac ccc aag agg ggc    ttc tac att agg gcc ctg ttt gat tac gac
ala ser leu arg ser asn pro lys arg gly    phe tyr ile arg ala leu phe asp tyr asp 1936/441                                    1966/451
aag acc aag gac tgc ggt ttc ttg agc cag    gcc ctg agc ttc cgc ttc ggg gat gtg ctt
lys thr lys asp cys gly phe leu ser gln    ala leu ser phe arg phe gly asp val leu 1996/461                                    2026/471
cat gtc att gac gct ggt gac gaa gag tgg    tgg caa gca cgg cgg gtc cac tcc gac agt
his val ile asp ala gly asp glu glu trp    trp gln ala arg arg val his ser asp ser 2056/481                                    2086/491
gag acc gac gac att ggc ttc att ccc agc    aaa cgg cgg gtc gag cga cga gag tgg tca
glu thr asp asp ile gly phe ile pro ser    lys arg arg val glu arg arg glu trp ser 2116/501                                    2146/511
agg tta aag gcc aag gac tgg ggc tcc agc    tct gga tca cag ggt cga gaa gac tcg gtt
arg leu lys ala lys asp trp gly ser ser    ser gly ser gln gly arg glu asp ser val 2176/521                                    2206/531
ctg agc tat gag acg gtg acc cag atg gaa    gtg cac tat gct cgt ccc atc atc atc ctt
leu ser tyr glu thr val thr gln met glu    val his tyr ala arg pro ile ile ile leu 2236/541                                    2266/551
gga ccc acc aaa gac cgt gcc aac gat gat    ctt ctc tcc gag ttc ccc gac aag ttt gga
gly pro thr lys asp arg ala asn asp asp    leu leu ser glu phe pro asp lys phe gly
```

Fig. 11B/1

```
2296/561                                    2326/571
tcc tgt gtc cct cat acg aca cgt cct aag    cgg gaa tat gag ata gac ggc cgg gat tac
ser cys val pro his thr thr arg pro lys    arg glu tyr glu ile asp gly arg asp tyr 2356/581                                    2386/591
cac ttt gtc tcc tcc cgg gag aaa atg gag    aag gac atc cag gca cac aag ttc att gag
his phe val ser ser arg glu lys met glu    lys asp ile gln ala his lys phe ile glu 2416/601                                    2446/611
gct ggc cag tac aac agc cac ctc tat ggg    acc agc gtc cag tct gtg cga gag gta gca
ala gly gln tyr asn ser his leu tyr gly    thr ser val gln ser val arg glu val ala 2476/621                                    2506/631
gag cag ggg aag cac tgc atc ctc gat gtc    tcg gcc aat gcc gtg cgg cgg ctg cag gcg
glu gln gly lys his cys ile leu asp val    ser ala asn ala val arg arg leu gln ala 2536/641                                    2566/651
gcc cac ctg cac ccc atc gcc atc ttc atc    cgt ccc cgc tcc ctg gag aat gtg cta gag
ala his leu his pro ile ala ile phe ile    arg pro arg ser leu glu asn val leu glu 2596/661                                    2626/671
atc aat aag cgg atc aca gag gag caa gcc    cgg aaa gcc ttc gac aga gcc acg aag ctg
ile asn lys arg ile thr glu glu gln ala    arg lys ala phe asp arg ala thr lys leu 2656/681                                    2686/691
gag cag gag ttc aca gag tgc ttc tca gcc    atc gta gag ggc gac agc ttt gaa gag atc
glu gln glu phe thr glu cys phe ser ala    ile val glu gly asp ser phe glu glu ile 2716/701                                    2746/711
tat cac aaa gtg aaa cgt gtc att gaa gac    ctc tca ggc ccc tac atc tgg gtc cca gcc
tyr his lys val lys arg val ile glu asp    leu ser gly pro tyr ile trp val pro ala 2776/721                                    2806/731
cga gag aga ctc tCC AAT TCG GTC CGG CGG    GAG CGG ATC CGG CGG CCA GTC CCC GCG GGC
arg glu arg leu ser asn ser val arg arg    glu arg ile arg arg pro val pro ala gly 2836/741                                    2866/751
CCC ACC ATG agc aag ggc gag gag ctg ttc    acc ggg gtg gtg ccc atc ctg gtc gag ctg
pro thr met ser lys gly glu glu leu phe    thr gly val val pro ile leu val glu leu 2896/761                                    2926/771
gac ggc gac gta aac ggc cac aag ttc agc    gtg tcc ggc gag ggc gag ggc gat gcc acc
asp gly asp val asn gly his lys phe ser    val ser gly glu gly glu gly asp ala thr 2956/781                                    2986/791
tac ggc aag ctg acc ctg aag ttc atc tgc    acc acc ggc aag ctg ccc gtg ccc tgg ccc
tyr gly lys leu thr leu lys phe ile cys    thr thr gly lys leu pro val pro trp pro 3016/801                                    3046/811
acc ctc gtg acc acc ctg acc tac ggc gtg    cag tgc ttc agc cgc tac ccc gac cac atg
thr leu val thr thr leu thr tyr gly val    gln cys phe ser arg tyr pro asp his met 3076/821                                    3106/831
aag cag cac gac ttc ttc aag tcc gcc atg    ccc gaa ggc tac gtc cag gag cgc acc atc
lys gln his asp phe phe lys ser ala met    pro glu gly tyr val gln glu arg thr ile
```

Fig. 11B/2

```
3136/841                                              3166/851
ttc ttc aag gac gac ggc aac tac aag acc  cgc gcc gag gtg aag ttc gag ggc gac acc
phe phe lys asp asp gly asn tyr lys thr  arg ala glu val lys phe glu gly asp thr 3196/861                                              3226/871
ctg gtg aac cgc atc gag ctg aag ggc atc  gac ttc aag gag gac ggc aac atc ctg ggg
leu val asn arg ile glu leu lys gly ile  asp phe lys glu asp gly asn ile leu gly 3256/881                                              3286/891
cac aag ctg gag tac aac tac aac agc cac  aac gtc tat atc atg gcc gac aag cag aag
his lys leu glu tyr asn tyr asn ser his  asn val tyr ile met ala asp lys gln lys 3316/901                                              3346/911
aac ggc atc aag gCC aac ttc aag atc cgc  cac aac atc gag gac ggc agc gtg cag ctc
asn gly ile lys ala asn phe lys ile arg  his asn ile glu asp gly ser val gln leu 3376/921                                              3406/931
gcc gac cac tac cag cag aac acc ccc atc  ggc gac ggc ccc gtg ctg ctg ccc gac aac
ala asp his tyr gln gln asn thr pro ile  gly asp gly pro val leu leu pro asp asn 3436/941                                              3466/951
cac tac ctg agc acc cag tcc gcc ctg agc  aaa gac ccc aac gag aag cgc gat cac atg
his tyr leu ser thr gln ser ala leu ser  lys asp pro asn glu lys arg asp his met 3496/961                                              3526/971
gtc ctg ctg gag ttc gtg acc gcc gcc ggg  atc act cAc ggc atg gac gag ctg tac aag
val leu leu glu phe val thr ala ala gly  ile thr his gly met asp glu leu tyr lys 3556/981                                              3586/991
tCC GGC GGG AGC GGA TCC GGC GGC CAG TCC  GGC GGG AGC GGA TCC GGC GGC CAG TCC GGC
ser gly gly ser gly ser gly gly gln ser  gly gly ser gly ser gly gly gln ser gly 3616/1001                                             3646/1011
GGG AGC GGA TCC GGC GGC CAG TCC GGC GGG  AGC GGA TCC GGC GGC CAG TCC GGC GGG AGC
gly ser gly ser gly gly gln ser gly gly  ser gly ser gly gly gln ser gly gly ser 3676/1021                                             3706/1031
GGA TCC GGC GGC CAG Tcc gga ctc aGA TCT  gtc aaa ctt aca tca gac ttc gac aac cca
gly ser gly gly gln ser gly leu arg ser  val lys leu thr ser asp phe asp asn pro 3736/1041                                             3766/1051
aga tgg att gga cga cac aag cat atg ttc  aat ttc ctt gat gtc aac cac aat gga aaa
arg trp ile gly arg his lys his met phe  asn phe leu asp val asn his asn gly lys 3796/1061                                             3826/1071
atc tct ctt gac gag atg gtc tac aag gca  tct gat att gtc atc aat aac ctt gga gca
ile ser leu asp glu met val tyr lys ala  ser asp ile val ile asn asn leu gly ala 3856/1081                                             3886/1091
aca cct gag caa gcc aaa cga cac aaa gat  gct gtG gaa gcc ttc ttc gga gga gct gga
thr pro glu gln ala lys arg his lys asp  ala val glu ala phe phe gly gly ala gly 3916/1101                                             3946/1111
atg aaa tat ggt gtg gaa act gat tgg cct  gca tat att gaa gga tgg aaa aaa ttg gct
met lys tyr gly val glu thr asp trp pro  ala tyr ile glu gly trp lys lys leu ala
```

Fig. 11B/3

```
3976/1121                                       4006/1131
act gat gaa ttg gag aaa tac gcc aaa aac   gaa cca acC ctc atc cgC atC tgg ggt gat
thr asp glu leu glu lys tyr ala lys asn   glu pro thr leu ile arg ile trp gly asp 4036/1141                                       4066/1151
gct ttg ttt gat atc gtt gac aaa gat caa   aat gga gct att aca ctg gat gaa tgg aaa
ala leu phe asp ile val asp lys asp gln   asn gly ala ile thr leu asp glu trp lys 4096/1161                                       4126/1171
gca tac acc aaa gct gct ggt atc atc caa   tca tca gaa gat tgc gag gaa aca ttc aga
ala tyr thr lys ala ala gly ile ile gln   ser ser glu asp cys glu glu thr phe arg 4156/1181                                       4186/1191
gtg tgc gat att gat gaa agt gga caa ctc   gat gtt gat gag atg aca aga caG cat CtG
val cys asp ile asp glu ser gly gln leu   asp val asp glu met thr arg gln his leu 4216/1201                                       4246/1211
gga ttt tgg tac acc atg gat cct gct tgc   gaa aag ctc tac ggt gga gct gtc ccc taa
gly phe trp tyr thr met asp pro ala cys   glu lys leu tyr gly gly ala val pro stop
```

Fig. 11B/4

Plasmid Data Sheet
Plasmid name: mtGA
Other name: mitoG5A, mtG5A
Insert size: 1434 bp
Inserted gene: GFP: bases 741-1454
Aequorin: bases 1605-2174

Vector: pCMV/myc/mito (Invitrogen)
Resistance gene: Ampicillin

```
636/1                                           666/11
ATG TCC GTC CTG ACG CCG CTG CTG CTG CGG GGC TTG ACA GGC TCG GCC CGG CGG CTC CCA
Met ser val leu thr pro leu leu leu arg gly leu thr gly ser ala arg arg leu pro 696/21                                          726/31
GTG CCG CGC GCC AAG ATC CAT TCG TTG ctg cag ccg cgg gcc acc atg agc aag ggc gag
val pro arg ala lys ile his ser leu leu gln pro arg ala thr met ser lys gly glu 756/41                                          786/51
gag ctg ttc acc ggg gtg gtg ccc atc ctg gtc gag ctg gac ggc gac gta aac ggc cac
glu leu phe thr gly val val pro ile leu val glu leu asp gly asp val asn gly his 816/61                                          846/71
aag ttc agc gtg tcc ggc gag ggc gag ggc gat gcc acc tac ggc aag ctg acc ctg aag
lys phe ser val ser gly glu gly glu gly asp ala thr tyr gly lys leu thr leu lys 876/81                                          906/91
ttc atc tgc acc acc ggc aag ctg ccc gtg ccc tgg ccc acc ctc gtg acc acc ctg acc
phe ile cys thr thr gly lys leu pro val pro trp pro thr leu val thr thr leu thr 936/101                                         966/111
tac ggc gtg cag tgc ttc agc cgc tac ccc gac cac atg aag cag cac gac ttc ttc aag
tyr gly val gln cys phe ser arg tyr pro asp his met lys gln his asp phe phe lys 996/121                                         1026/131
tcc gcc atg ccc gaa ggc tac gtc cag gag cgc acc atc ttc ttc aag gac gac ggc aac
ser ala met pro glu gly tyr val gln glu arg thr ile phe phe lys asp asp gly asn 1056/141                                        1086/151
tac aag acc cgc gcc gag gtg aag ttc gag ggc gac acc ctg gtg aac cgc atc gag ctg
tyr lys thr arg ala glu val lys phe glu gly asp thr leu val asn arg ile glu leu 1116/161                                        1146/171
aag ggc atc gac ttc aag gag gac ggc aac atc ctg ggg cac aag ctg gag tac aac tac
lys gly ile asp phe lys glu asp gly asn ile leu gly his lys leu glu tyr asn tyr 1176/181                                        1206/191
aac agc cac aac gtc tat atc atg gcc gac aag cag aag aac ggc atc aag gCC aac ttc
asn ser his asn val tyr ile met ala asp lys gln lys asn gly ile lys ala asn phe 1236/201                                        1266/211
aag atc cgc cac aac atc gag gac ggc agc gtg cag ctc gcc gac cac tac cag cag aac
lys ile arg his asn ile glu asp gly ser val gln leu ala asp his tyr gln gln asn 1296/221                                        1326/231
acc ccc atc ggc gac ggc ccc gtg ctg ctg ccc gac aac cac tac ctg agc acc cag tcc
thr pro ile gly asp gly pro val leu leu pro asp asn his tyr leu ser thr gln ser 1356/241                                        1386/251
gcc ctg agc aaa gac ccc aac gag aag cgc gat cac atg gtc ctg ctg gag ttc gtg acc
ala leu ser lys asp pro asn glu lys arg asp his met val leu leu glu phe val thr 1416/261                                        1446/271
gcc gcc ggg atc act cAc ggc atg gac gag ctg tac aag tCC GGC GGG AGC GGA TCC GGC
ala ala gly ile thr his gly met asp glu leu tyr lys ser gly gly ser gly ser gly
```

Figure 12B

```
1476/281                              1506/291
GGC CAG TCC GGC GGG AGC GGA TCC GGC GGC CAG TCC GGC GGG AGC GGA TCC GGC GGC CAG
gly gln ser gly gly ser gly ser gly gly gln ser gly gly ser gly ser gly gly gln 1536/301                              1566/311
TCC GGC GGG AGC GGA TCC GGC GGC CAG TCC GGC GGG AGC GGA TCC GGC GGC CAG TCC GGA
ser gly gly ser gly ser gly gly gln ser gly gly ser gly ser gly gly gln ser gly 1596/321                              1626/331
CTC AGA TCT gtc aaa ctt aca tca gac ttc gac aac cca aga tgg att gga cga cac aag
leu arg ser val lys leu thr ser asp phe asp asn pro arg trp ile gly arg his lys 1656/341                              1686/351
cat atg ttc aat ttc ctt gat gtc aac cac aat gga aaa atc tct ctt gac gag atg gtc his met phe asn phe leu asp val asn his asn gly lys ile ser leu asp glu met val
1716/361                              1746/371
tac aag gca tct gat att gtc atc aat aac ctt gga gca aca cct gag caa gcc aaa cga tyr lys ala ser asp ile val ile asn asn leu gly ala thr pro glu gln ala lys arg
1776/381                              1806/391
cac aaa gat gct gtG gaa gcc ttc ttc gga gga gct gga atg aaa tat ggt gtg gaa act
his lys asp ala val glu ala phe phe gly gly ala gly met lys tyr gly val glu thr 1836/401                              1866/411
gat tgg cct gca tat att gaa gga tgg aaa aaa ttg gct act gat gaa ttg gag aaa tac
asp trp pro ala tyr ile glu gly trp lys lys leu ala thr asp glu leu glu lys tyr 1896/421                              1926/431
gcc aaa aac gaa cca acC ctc atc cgC atC tgg ggt gat gct ttg ttt gat atc gtt gac
ala lys asn glu pro thr leu ile arg ile trp gly asp ala leu phe asp ile val asp 1956/441                              1986/451
aaa gat caa aat gga gct att aca ctg gat gaa tgg aaa gca tac acc aaa gct gct ggt
lys asp gln asn gly ala ile thr leu asp glu trp lys ala tyr thr lys ala ala gly 2016/461                              2046/471
atc atc caa tca tca gaa gat tgc gag gaa aca ttc aga gtg tgc gat att gat gaa agt
ile ile gln ser ser glu asp cys glu glu thr phe arg val cys asp ile asp glu ser 2076/481                              2106/491
gga caa ctc gat gtt gat gag atg aca aga caG cat CtG gga ttt tgg tac acc atg gat
gly gln leu asp val asp glu met thr arg gln his leu gly phe trp tyr thr met asp 2136/501                              2166/511
cct gct tgc gaa aag ctc tac ggt gga gct gtc ccc taa
pro ala cys glu lys leu tyr gly gly ala val pro Stop
```

Figure 12B/1

NON-INVASIVE REAL-TIME IN VIVO BIOLUMINESCENCE IMAGING OF LOCAL CA²⁺ DYNAMICS IN LIVING ORGANISMS

CROSS-REFERENCE TO RELATED APPLICATIONS

This application is based on and claims the benefit of U.S. Provisional Application No. 60/543,659, filed Feb. 12, 2004, The entire disclosure of this application is relied upon and incorporated by reference herein.

BACKGROUND OF THE INVENTION

This invention provides a method to permit optical detection of localised calcium signaling (e.g. high $Ca^{2+}$ concentration microdomains) using a genetically encoded bioluminescent reporter. This invention describes a method to detect the effect of a pharmacological agent or neuromodulator on localised $Ca^{2+}$ signalling. The invention especially provides a method to visualise dynamic fluctuations in localised $Ca^{2+}$ associated with cell or tissue activation, such as neuronal activation and relating to optical detection of ion channel function (receptors/channels permeable to $Ca^{2+}$) and synaptic transmission. This invention also concerns a method for optical detection of the dynamics of $Ca^{2+}$ in a biological system, said method comprising monitoring the photons emitted by a recombinant $Ca^{2+}$-sensitive polypeptide, which comprises or consists of a chemiluminescent protein linked to a fluorescent protein, present in said biological system. Also, this invention provides a transgenic non-human animal expressing a recombinant polypeptide sensitive to calcium concentration, consisting of at least a chemiluminescent protein linked to a fluorescent protein, in conditions enabling the in vivo monitoring of local calcium dynamics. $Ca^{2+}$ is one of the most universal and physiologically important signaling molecules that plays a role in almost all cellular functions, including fertilization, secretion, contraction-relaxation, cell motility, cytoplasmic and mitochondrial metabolism, synthesis, production of proteins, gene expression, cell cycle progression and apoptosis (Rizzuto et al., 2002).

Characteristics of $Ca^{2+}$ transients at the cellular and subcellular level are complex, and vary according to spatial, temporal and quantitative factors. Up to a 20,000-fold difference in the concentration of $Ca^{2+}$ exists between the cytoplasm and the extracellular space, such that even when channels are open for a short time, a high rate of $Ca^{2+}$ influx will occur. Factors such as diffusion, $Ca^{2+}$ binding to buffer proteins and sequestration by cellular compartments, will create a $Ca^{2+}$ gradient and result in a high concentration microdomain within a few hundred nanometers from the pore of a channel. Over longer distances such as tens of microns, the effective diffusion coefficient of $Ca^{2+}$ will be strongly reduced.

Because $Ca^{2+}$ signals are highly regulated in space, time and amplitude, they have a defined profile (e.g. amplitude and kinetics). $Ca^{2+}$ transients are shaped by cytosolic diffusion of $Ca^{2+}$, buffering by $Ca^{2+}$ binding proteins and $Ca^{2+}$ transport by organellar (Bauer, 2001; Llinas et al., 1995). The concentration of $Ca^{2+}$ reached and its kinetics in any given cellular microdomain is critical for determining whether a signaling pathway succeeds or not in reaching its targets. $Ca^{2+}$ is necessary for activation of many key cellular proteins, including enzymes such as kinases and phosphatases, transcription factors and the protein machinery involved in secretion. $Ca^{2+}$ signaling cascades may also mediate negative feedback on the regulation of biochemical pathways or functional receptors and transport mechanisms. The propagation of $Ca^{2+}$ within a cell can also help to link local signaling pathways to ones that are more remote within a cell or for facilitating long distance communication between cells or networks of cells (e.g. central nervous system) (Augustine et al., 2003).

$Ca^{2+}$ transients producing high $Ca^{2+}$ concentration microdomains are associated with a diverse array of functions important in development, secretion and apoptosis, and many cellular processes, including gene expression, neurotransmission, synaptic plasticity and neuronal cell death (Augustine et al., 2003; Bauer, 2001; Llinas et al., 1995; Neher, 1998). Characterising the spatiotemporal specificity of $Ca^{2+}$ profiles is important to understand the mechanisms contributing to perturbed cellular $Ca^{2+}$ homeostasis, which has been implicated in many pathological processes, including migraine, schizophrenia and early events associated with the onset of neurodegenerative diseases such as Alzheimer's, Parkinson's and Huntington's diseases (Mattson and Chan, 2003). Because $Ca^{2+}$ is directly or indirectly associated with almost all cell signaling pathways, optical detection of $Ca^{2+}$ is a universal measure of biological activity at the molecular, cellular, tissue and whole animal level. Tremendous progress has been made in the imaging of localised $Ca^{2+}$ events using light microscopy. To this end, $Ca^{2+}$ signalling in single dendritic spines (Yuste, 2003) and more recently in a single synapse (Digregorio, 2003) has been accomplished using fluorescent dyes. However, one way to spatially improve measurements of $Ca^{2+}$ is to genetically target a reporter protein to a specific location whereby $Ca^{2+}$ activity can be directly visualised. Specifically, such a reporter protein could be fixed in a microdomain (within 200 nm of the source or acceptor) or even within a nanodomain (within 20 nm) (see Augustine et al. 2003 for review). Expression of a reporter gene under the control of cell type-specific promoters in transgenic animals, can also offer a non-invasive way to follow dynamic changes in a single cell type, tissues or anatomically in whole animal imaging.

Monitoring calcium in real-time can help to improve the understanding of the development, the plasticity and the functioning of a biological system, for example the central nervous system. Indeed, much effort has been dedicated to the development of an optical technique to image electrical activity in single-cell type and particularly single neurons and networks of neurons, but there continues to be a need to achieve this goal through use also of electrophysiological techniques. Genetic targeting of a $Ca^{2+}$ reporter probe in spatially restricted areas of a cell or living system (e.g. inside of a compartment, to microdomains or nanodomains, or by fusion to a specific polypeptide) is a molecular imaging approach for detecting specific cellular activities or physiological functions. This invention aids in fulfilling these needs in the art, by providing a method for optical detection of the dynamics of $Ca^{2+}$ in a biological system, said method comprising monitoring the photons emitted by a recombinant $Ca^{2+}$-sensitive polypeptide, which comprises or consists of a chemiluminescent protein linked to a fluorescent protein, present in said biological system, as well as a transgenic non-human animal expressing said recombinant polypeptide sensitive to calcium. The non-invasive nature of this technique as well as the evidence that the recombinant protein is non-toxic, means that the method could possibly also be applied in humans.

BRIEF DESCRIPTION OF THE DRAWINGS

This invention will be described with reference to the following drawings.

DESCRIPTION OF THE INVENTION

Figure 1:
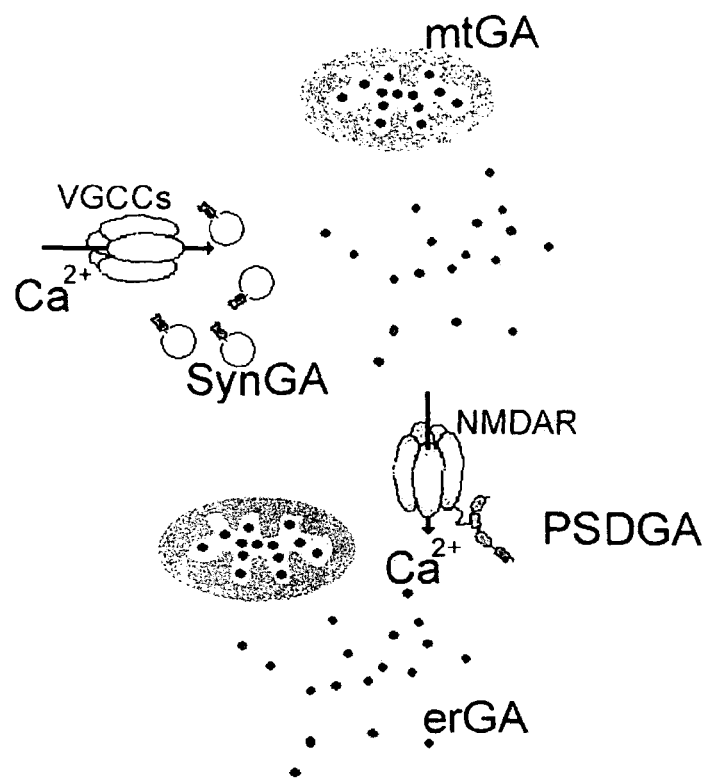
FIG. 1: Schematic diagram showing the localisation of the different GFP-Aequorin reporters targeted to specific subcellular domains in the pre- and post-synaptic compartment. The GFP-aequorin reporter has been targeted to different cellular domains, including the mitochondrial matrix (mtGA), by fusion to synaptotagmin I (SynGA), to the lumen of the endoplasmic reticulum (erGA) and by fusion to PSD95 (PSDGA). The low-affinity version of each reporter could allow selective detection of high-calcium concentration microdomains that are indicative of specific cellular activities.

Among the coelenterates, bioluminescent species exist. Numerous studies have shown that the bioluminescence is generated by photoproteins that are often sensitive to calcium. Sensitive as used herein when referring to a protein means any modification in said sensitive protein in its conformation, affinity for other molecules, localisation, or in the emission of light. Particular proteins of this type emit a flash of light in response to an increase in the concentration of calcium ions. Among these photoproteins, aequorin is one of the most well studied (Blinks et al., 1976).

Isolated in the jellyfish *Aequoria victoria* (Shimomura et al., 1962), aequorin is a Ca2+ sensitive photoprotein, i.e., it is modified and/or activated when interacting with Ca2+. Said modification and/or activation is detectable especially through non-invasive ways. More particularly, when aequorin interacts with Ca2+, after binding with two or three calcium ions, it emits a flash of blue light with a spectrum of maximum wavelength 470 nm. Contrary to a classical luciferase-luciferin reaction, the emission of light does not require exogenous oxygen, and the total amount of light is related to the amount of protein and the concentration of Ca2+. Oxygen is molecularly bound and the reconstitution of aequorin occurs, by the action of apoaequorin, a protein with a molecular mass of 21 kDa, and coelenterazine. The emission of photons is caused by a peroxidation reaction in the coelenterazine, after binding with the calcium ions on the aequorin protein. Two hypotheses have been suggested for this process: (i) the binding between aequorin and calcium ions induces the emission of light by a conformational change in the protein, allowing oxygen to react with coelenterazine, and (ii) oxygen plays a role in the binding between coelenterazine and apoaequorin (Shimomura and Johnson, 1978). Aequorin may be recreated in vitro and in vivo by coelenterazine for example by adding it directly into the medium or by administration, and particularly injection, into an organism (Shimomura and Johnson, 1978).

Up to thirty different semi-synthetic aequorins can be produced by replacing the coelenterazine moiety in aequorin with different analogues of coelenterazine (Shimomura, 1995). The different semi-synthetic aequorins show spectral variations, different Ca2+ binding affinities, variations in stability, membrane permeability and relative regeneration rates. Measurements of Ca2+ concentrations can be undertaken between 100 nM and 1 mM, using different combinations. When native aequorin is reconstituted with native coelenterazine, it has a low affinity for Ca2+ (Kd=10 μM), making it a good sensor in the range of biological Ca2+ concentration variations. Although the relationship between light emission and calcium ion concentration may not be linear, a logarithmic relationship between the emission of light and the calcium ion concentration has nonetheless been determined (Johnson and Shimomura, 1978). The fractional rate of aequorin consumption is proportional, in the physiological pCa range, to [Ca2+]. Indeed, a 200-fold increase in the signal to background noise ratio is measured when the Ca2+ concentration goes from 10-7M to 10-6M, and by a factor of 1000, from 10-6M to 10-5M (Cobbold and Rink, 1987). Moreover, the kinetics of the signal emission is rapid enough to detect transitory increases in Ca2+ ion concentrations. An increase in light intensity with a time constant of 6 msec, under calcium saturation conditions, has been shown (Blinks et al., 1978). Aequorin is thus a photoprotein that is well adapted to measure rapid and elevated increases in Ca2+ ions under physiological conditions. Recent studies have investigated the CRET response time of a GFP-aequorin reporter with a linker (Gorokhovatsky et al, 2004). They indicate that the Ca2+ triggered bioluminescence reaction of GFP-aequorin exhibits the typical flash-type bioluminescence reaction of aequorin. After addition of Ca2+ in a stopped-flow apparatus, light emission begins immediately and reaches a peak within 50 ms. The response kinetics appears to be comparable with the association rate constant indicated for 'cameleons' (Miyawaki et al, 1997).

The cloning of the apoaequorin gene by Prasher et al., (1985) and Inouye et al. (1985) has led to the creation of expression vectors, making possible its targeting in a specific cell compartment by fusion with nuclear, cytoplasmic, mitochondrial, endoplasmic reticulum or plasma membrane signal peptides (Kendall et al., 1992; Di Giorgio et al., 1996). In addition, the in vivo expression of the protein makes possible its detection at low levels, leaving the intracellular physiology of calcium undisturbed.

In nature, photoprotein activity is very often linked to a second protein. The most common is the "green fluorescent protein" or GFP. The light emitted in this case is in fact green. The hypothesis of an energy transfer between aequorin and GFP by a radiative mechanism was proposed in the 1960s by Johnson et al., (1962). The blue light emitted by aequorin in the presence of Ca2+ is presumably absorbed by GFP and reemitted with a spectrum having a maximum wavelength of 509 nm. Other studies have shown that this transfer of energy occurs through a non-radiative mechanism made possible through the formation of heterotetramer between GFP and aequorin. Morise et al. (1974) have succeeded in visualizing this energy transfer in vitro, by co-adsorption of the two molecules on a DEAE-cellulose membrane. However, these studies indicated that the quantum yield of Ca2+-triggered luminescence of aequorin in this condition was 0.23, which coincides with that of aequorin alone (Morise et al, 1974).

GFP, also isolated in the jellyfish *Aequoria victoria*, was cloned (Prasher et al., 1992). It has been used in different biological systems as a cellular expression and lineage marker (Cubift et al., 1995). Detecting this protein using classical fluorescence microscopy is relatively easy to do in both living organisms and fixed tissue. In addition, fluorescent emission does not require the addition of a cofactor or coenzyme and depends on an autocatalytic post-translational process. The fluorophore, consisting of nine amino acids, is characterized by the formation of a cycle between serine 65 and glycine 67, which gives rise to an intermediate imidazolidine 5, followed by oxidation of tyrosine 66, transforming it into dehydrotyrosine (Heim et al., 1994). This group is found inside a cylinder composed of 11β layers, which constitutes an environment that interacts directly with the chromophore (Yang et al., 1996).

Monitoring calcium fluxes in real time could help to understand the development, the plasticity, and the functioning of many organs, such as the central nervous system, the heart, the brain and the liver, and their associated pathologies. In jellyfish, the chemiluminescent, calcium binding, aequorin protein is associated with the green fluorescent protein (GFP), and a green bioluminescent signal is emitted upon Ca2+ stimulation. Aequorin alone is difficult to detect on the cellular and subcellular level owing to the weak emission of photons after excitation and makes it extremely difficult to detect in single-cells or with good temporal resolution.

A new marker sensitive to calcium with an apparent higher quantum yield is described in WO01/92300. This marker utilizes Chemiluminescence Resonance Energy Transfer (CRET) between the two molecules. Calcium sensitive bioluminescent reporter genes were constructed by fusing GFP and aequorin resulting in much more light being emitted. Different constructs obtained by recombination of the nucleic acid molecules encoding the GFP linked to aequorin are disclosed in the international application WO 01/92300, which is incorporated herein by reference.

Chemiluminescent and fluorescent activities of these fusion proteins were assessed in mammalian cells. Cystosolic Ca2+ increases were imaged at the single cell level with a cooled intensified CCD (coupled charge device) camera. This bifunctional reporter gene allows the investigation of calcium activities in neuronal networks and in specific subcellular compartments in transgenic animals.

This invention utilizes a fusion protein or recombinant protein constructed with aequorin and GFP to increase the quantum yield of Ca2+-induced bioluminescence. This activity can not be increased simply by co-expressing GFP with aequorin Aequorin has a low calcium binding affinity (Kd=10 μM) so it should not have a major effect as a [Ca2+]i buffer system nor should it flatten Ca2+ gradients. Kinetics of the signal emission is rapid enough to detect transitory increases in Ca2+ ion concentration, with a time constant of 6 msec, under calcium saturation conditions. The total amount of light is proportional to the amount of protein and Ca2+ concentration. It is therefore possible to calibrate the amount of light emitted at any given time point into a concentration of calcium. Studies have shown that Aequorin alone is extremely difficult to detect at the single-cell and subcellular level due to the weak level of photon emission.

The binding of Ca2+ to aequorin, which has three EF-hand structures characteristic of Ca2+ binding sites, induces a conformational change resulting in the oxidation of celenterazine via an intramolecular reaction. The coelenteramide produced is in an excited state and blue light (max: 470 nm) is emitted when it returns to its ground state (Shimomura & Johnson, 1978). When GFP is fused to Aequorin by a flexible linker (WO 01/92300), the energy acquired by aequorin after Ca2+ binding, is transferred from the activated oxyluciferin to GFP without emission of blue light. The GFP acceptor fluorophore is excited by the oxycoelenterazine through a radiationless energy transfer. The result is the emission of a green shifted light (max, 509 nm) when the excited GFP returns to its ground state.

The GFP-Aequorin of the invention is a dual reporter protein combining properties of Ca2+-sensitivity and fluorescence of aequorin and GFP, respectively. The recombinant protein can be detected with classical epifluorescence in living or fixed samples and can be used to monitor Ca2+ activities by detection of bioluminescence in living samples. The GFP-Aequorin polypeptide is genetically-encoded and the coding sequence and/or the expressed polypeptide can be localised to specific cellular domains. It can also or alternatively be transferred to organisms by transgenesis without perturbing the function of the photoprotein. This nucleic acid encoding the recombinant polypeptide of the invention can also be expressed under the control of an appropriate transcriptional and/or translational system. "Appropriate" as used herein refers to elements necessary for the transcription and/ or the translation of a nucleic acid encoding the recombinant polypeptide of the invention in a given cell type, given tissue, given cellular compartment (such as mitochondria, chloroplast . . . ) or given cellular domains. To achieve said specific expression the nucleic acid is for example recombined under the control of cell-type specific promoters or tissue-type specific promoter, which can enable the measurement of Ca2+ signaling in a single-cell type or single tissue-type, within a determined tissue or in whole animals.

Chemiluminescent and fluorescent activities of the GFP-Aequorin protein have been assessed in mammalian cells. Cytosolic Ca2+ increases have been previously imaged at the single-cell level with a cooled intensified CCD (coupled charge device) camera (WO 01/92300). Our studies of GFP-Aequorin at the single-cell level demonstrate the sensitivity of this recombinant polypeptide for use as a probe (see results hereafter). GFP-Aequorin does not significantly interfere with local Ca2+ signaling due to its low affinity for Ca2+. GFP-aequorin is therefore a bioluminescent reporter of intracellular Ca2+ activities and can be used to follow dynamic changes in single-cells, tissue slices or living animals. GFP fluorescence is also a valuable reporter of gene expression and marker of cellular localization. Moreover, bioluminescent molecules do no not require the input of radiative energy as they utilize chemical energy to produce light. Hence, there is virtually no background in the signal.

In contrast, fluorescent dyes cannot be localised exclusively to subcellular domains. Cameleons on the other hand are genetically targetable. These reporters generally have a low signal-to-noise ratio and long-term imaging is difficult due to phototoxicity and problems associated with photobleaching. This limits the use of these probes for visualising dynamic changes over prolonged periods, for example in studies of learning and memory, development and circadian rhythms. Fluorescence requires radiative energy, which results in photobleaching, phototoxicity, autofluorescence and a high background signal. An external light source is necessary in order to excite fluorescent molecules. Excitation light will be absorbed when passing through tissue to excite fluorescent molecules. Similarly, the same will occur when the emission light is detected through tissue. For the moment, in vivo non-invasive whole animal imaging is largely restricted to bioluminescent reporters.

Other Related Techniques:

Electrophysiological recording is restricted to the cell-soma or large dendritic regions that are accessible with a micropipette.

Yuste et al. decribes the use of fluorescent indicators to detect activation of a "follower" neuron that relates to the optical detection of a connection between two neurons or between a plurality of neurons (Yuste et al, 2003). This approach, however, suffers from the disadvantage that these fluorescent indicators are useful only for short-term or time lapse imaging applications and because they can not be genetically-targeted. Specifically; (1) Non-selective staining and the problem of dye leakage from cells after a short period at physiological temperature (2) The requirement of light excitation restricts long-term dynamic imaging due to photobleaching and photodynamic damage caused to living (or fixed) dissociated cell culture or tissue samples. (3) Imaging localised Ca2+ dynamics or high Ca2+ concentration microdomains with fluorescent dyes is difficult and below the limits of spatial resolution offered by light microscopy techniques.

Voltage-sensitive dyes are discussed as a useful technique for monitoring "multineuronal activity in an intact central nervous system" (Wu et al, 1998). These probes are fluorescent and are therefore subject to the same limitations as discussed for Ca2+ sensitive fluorescent dyes (see Knöpfel et al, 2003 for review). A genetically encodable form has also been developed (Siegel & Isacoff, 1997), but has a low signal-to-noise ratio.

'Cameleons' are a class of genetically encoded Ca2+ sensitive fluorescent probes consisting of two GFP's covalently linked by a calmodulin binding sequence. Cameleons generally have a low signal-to-noise ratio and long-term imaging is difficult due to phototoxicity and problems associated with photobleaching. Targeting of this probe has been made to the mitochondrial matrix (Fillipin et al, 2003), to the lumen of the endoplasmic reticulum (Varadi & Rutter, 2002) and to the surface of large dense core secretory vesicles via fusion with a transmembrane protein known as phogrin (Emmanouilidou et al, 1999).

This invention describes a novel approach using combined fluorescence/bioluminescence imaging of single-cell type, including neurons and neuronal populations, to detect calcium signalling microdomains associated with synaptic transmission and to visualise in real-time the calcium dynamics in single-cell type, such as in neurons and neuronal networks as well as other organs and tissues.

In particular, this invention provides a recombinant polypeptide useful for detection of Ca2+ microdomains. The recombinant polypeptide comprises a bioluminescent polypeptide, optionally fused to a peptide or a protein capable of targeting to a subcellular domain. In one embodiment of the invention, the bioluminescent polypeptide comprises a chemiluminescent peptide that binds calcium ion, and a fluorescent peptide. In another example, the recombinant polypeptide consists of said chemiluminescent peptide binding calcium ions and said fluorescent peptide. The recombinant polypeptide may also consist of a chemiluminescent peptide, a fluorescent peptide and a linker, and optionally is further fused to a peptide or a protein capable of targeting to a subcellular domain. In a particular embodiment, the recombinant polypeptide consists of a chemiluminescent peptide, a fluorescent peptide and a peptide or a protein capable of targeting to a subcellular domain. Another example is a recombinant polypeptide consisting of a chemiluminescent peptide, a fluorescent peptide, a linker and a peptide or a protein capable of targeting to a subcellular domain Targeting of GFP-Aequorin (GA) to subcellular compartments or cellular microdomains is possible by fusion with a peptide signal or a peptide or protein of interest.

According to a particular embodiment, this invention describes the targeting and use of the dual fluorescent/bioluminescent recombinant protein (GFP-Aequorin), to detect calcium signalling in cellular compartments and particularly in calcium microdomains associated with synaptic transmission. This invention also describes the use of these recombinant polypeptides for the 'real-time' optical detection of calcium dynamics in single cell or population of cells, such as single neurons and in neuronal populations. Although these studies describe the use of this recombinant polypeptide in neurons, they are intended also to highlight the sensitivity and other important characteristics offered by this reporter polypeptide. The use of this recombinant polypeptide is certainly not restricted to use in neurons. GFP-Aequorin has tremendous utility also in other cell types but certainly in most animal cells, plants, bacteria and also yeast, specifically any living system whereby calcium signalling is important.

An example of a chemiluminescent peptide is Aequorin or a mutant of aequorin. In a preferred embodiment, the mutant Aequorin has a different, and preferably lower, affinity for calcium ion, such as the mutant aequorin Asp407→Ala, wherein the numbering corresponds to the position of the mutation in Aequorin in a fusion protein comprising a fluorescent protein and Aequorin. In another example, it can have a higher affinity, when the h-coelenterazine analogue is used to regenerate the aequorin protein.

An example of a fluorescent peptide is green fluorescent protein (GFP), a variant of GFP or a mutant of GFP. Such a variant has the feature to emit photons at a different wavelength. Examples of such GFP variants are CFP (cyan fluorescent protein), YFP (yellow fluorescent protein) and RFP (red fluorescent protein).

A mutant or a variant of a chemiluminescent peptide or a fluorescent peptide is defined herein as a sequence having substitutions, deletions or additions according to the reference sequence. The amino acid substitutions can be conservative, semi-conservative or non-conservative.

Therefore, a particular recombinant polypeptide consists of Aequorin and GFP, especially of fusion polypeptide GFP-aequorin, with or without linker between them. Are included in the scope of the invention, fusions between Cyan fluorescent protein and aequorin (CFP-aequorin), between yellow fluorescent protein and aequorin (YFP-aequorin), between red fluorescent protein and aequorin (RFP) or triple fusions including any of these combinations (e.g. RFP-YFP-aequorin) as well as mutant or variant of the original GFP-aequorin, being a red-shifted version of GFP-aequorin or having mutations improving the brightness, the stability and/or the maturation of the reporter protein.

This invention also provides a recombinant polypeptide which consists of Aequorin, GFP and a linker, especially a peptidic linker. In a particular recombinant polypeptide, said chemiluminescent peptide is aequorin, the fluorescent peptide is GFP, and the aequorin and GFP are linked by a peptidic linker allowing Chemiluminescence Resonance Energy Transfer (CRET). A peptidic linker allowing CRET comprises or consists preferably of 4-63 amino acids and especially of 14-50 amino acids. In a particular embodiment, such a peptidic sequence comprises or consists of the sequence [Gly-Gly-Ser-Gly-Ser-Gly-Gly-Gln-Ser]n (SEQ ID NO: 1) with n is 1-5, and preferably n is 1 or n is 5.

In another particular embodiment of the recombinant polypeptide of the invention, the peptide or protein which is capable of targeting to a subcellular domain is selected from Synaptogamin, PSD95, subunit VIII of cytochrome C oxidase, and immunoglobulin heavy chain or a fragment thereof such as the N-terminal fragment.

This invention also provides a recombinant polynucleotide encoding the polypeptide of the invention.

In addition, this invention provides a vector comprising the polynucleotide of the invention and a host cell containing said recombinant polynucleotide or said vector. The cell can be, for example, a eukaryotic cell, or a prokaryotic cell, such as an animal cell, a plant cell, a bacteria, or a yeast.

The invention concerns a method for optical detection of the dynamics of Ca2+ in a biological system, said method comprising monitoring the photons emitted by a recombinant Ca2+-sensitive polypeptide of the invention, which comprises or consists of a chemiluminescent protein fused, or linked to a fluorescent protein, present in said biological system. Any polypeptide described in this application can be used in the carrying out of said detecting method. This method is useful for the optical detection of intracellular Ca2+ signaling or of the propagation of Ca2+ signal to detect communication from one cell to another.

Said method can be carried out for the monitoring of photons emission in different biological systems: in vitro in a cell or group of cells, in vivo in a animal or plant expressing said recombinant polypeptide of the invention or ex vivo in a tissue or group of cells from a transgenic animal or plant.

Said method comprises, prior to the monitoring of the emission of photons, the administration of said recombinant polypeptide or of a polynucleotide encoding said recombinant polypeptide into the biological system. In whole animal system, the recombinant polypeptide or the nucleic acid encoding it (or corresponding vector) is administrated preferably by intravenous, intraperitoneal or intramuscular injection. The administration of the nucleic acid encoding the recombinant polypeptide of the invention can be carried out by any appropriate means especially by recombinant vectors, in particular by recombinant viral vectors. In a particular embodiment of the invention, transgenic non-human animal or transgenic plant are provided, which have especially been transformed by the nucleic acid encoding the recombinant polypeptide. The transformation can be transient or definitive. In this case, the recombinant polypeptide of the invention is expressed from the modified genome of the plant or animal.

When expressed from the genome of a transgenic plant or animal, the expression and/or localization of said recombinant polypeptide may be restricted to a specific tissue, a single-cell type (such as neural, heart or liver cell) or a cellular compartment or domain (such as mitochondria or chloroplast).

Said method can also comprise, prior to the monitoring of the emission of photons, the administration of a molecule allowing the activation of the bioluminescent and/or fluorescent proteins. In the GFP-aequorin reporter protein, the method comprises the administration of coelenterazine in the biological system, in conditions and concentrations enabling the activation of the aequorin. Aequorin/coelenterazine systems have been disclosed in the art (Shimomura, 1991).

In a particular embodiment, this invention provides a method for detecting or quantifying Ca2+ at the subcellular level. The method comprises expressing in vivo a recombinant polypeptide of the invention encoded by a polynucleotide of the invention in a host cell especially in a non-human animal, and visualizing the presence of Ca2+. Optionally, the Ca2+ can be semi-quantified. In a preferred embodiment, the detection is a so-called "real-time" detection.

The invention also provides a method for the identification of physiological and/or pathological processes comprising optionally the characterization of the development morphology or functioning of a group of cells, a tissue, a cell or a cellular compartment or domain by GFP fluorescence detection, and the characterization of dynamics of Ca2+ in said group of cells, said tissue, said cell or said cellular compartment or domain by the method of optical detection of the invention.

The invention further relates to a method for the identification of physiological and/or pathological processes that may involve variations of calcium fluxes or signaling out of known normal ranges, wherein the method comprises the optical detection of the dynamics of Ca2+ in accordance with the present application. Alternatively said optical detection of the dynamics of Ca2+ can rather be included as a part of a protocol for the identification of such processes in particular in order to perform diagnosis or monitoring, for example monitoring of a therapeutic response.

In addition, this invention provides a transgenic non-human animal or plant, comprising a host cell of the invention.

This invention also provides a transgenic non-human animal, usable in the above-method of optical detection, expressing a genetically-encoded recombinant polypeptide of the invention as described above. In a particular embodiment, the recombinant polypeptide is encoded by a polynucleotide, optionally under the control of an appropriate transcriptional and translational system, inserted in the genome of said transgenic animal. This non-human animal can be a vertebrate and particularly mammals, such as primates or rodents. In a particular embodiment, this non-human animal is rat, rabbit or mouse.

This invention also concerns a method for producing a transgenic non-human animal of the invention comprising:
transferring a DNA construct into embryonic stem cells of a non-human animal, wherein said DNA construct comprises or consists of a sequence so-called transgene encoding a recombinant polypeptide sensitive to calcium concentration, said recombinant polypeptide comprising or consisting of a chemiluminescent protein linked to a fluorescent protein, and wherein said transgene is under the control of a promoter and optionally of conditional expression sequences,
selecting positive clones, wherein said DNA construct is inserted in the genome of said embryonic stem cells,
injecting said positive clones into blastocytes and recovering chimeric blastocytes,
breeding said chimeric blastocytes to obtain a non-human transgenic animal.

In a particular embodiment, wherein the expression of the recombinant polypeptide is conditional, the following method for producing a transgenic non-human animal can be used:
transferring a DNA construct into embryonic stem cells of a non-human animal, wherein said DNA construct comprises or consists of a sequence so-called transgene encoding a recombinant polypeptide sensitive to calcium concentration, said recombinant polypeptide comprising or consisting of a chemiluminescent protein linked to a fluorescent protein, and wherein said transgene is under the control of a promoter and optionally of conditional expression sequences,
selecting positive clones, wherein said DNA construct is inserted in the genome of said embryonic stem cells,
injecting said positive clones into blastocytes and recovering chimeric blastocytes,
breeding said chimeric blastocytes to obtain a first non-human transgenic animal,
crossing said resulting first non-human transgenic animal with an animal expressing an endonuclease, acting on said conditional expression sequences, in the tissues or cells in which expression of said recombinant polypeptide is needed, and
recovering a transgenic non-human animal expressing said recombinant polypeptide in specific tissue or cells.

"Conditional" as used herein means that the recombinant protein sensitive to calcium concentration of the invention is expressed at a chosen time throughout the development of the non-human transgenic animal. Therefore, in a particular embodiment, the recombinant protein is expressed when a recombinase catalyzes the recombination of conditional expression sequence, and for example when the enzyme Cre catalyses the recombination of the Lox recognition sites.

The expression of the recombinase or endonuclease, such as Cre, can be both spatially and temporally regulated according to the promoter located upstream of the nucleic acid encoding said recombinase. Said promoter can be a cell-specific promoter allowing the expression of the recombinase for example in liver, heart or brain cells.

In a particular embodiment, the expression of the recombinase may be activated by natural or synthetic molecules. Therefore, a ligand-dependent chimeric Cre recombinase, such as CreERT or CreERT2 recombinases, can be used. It consists of Cre fused to modified hormone binding domains of the estrogen receptor. The CreERT recombinases are inactive, but can be activated by the synthetic estrogen receptor ligand tamoxifen, therefore allowing for external temporal control of Cre activity. Indeed, by combining tissue-specific expression of a CreERT recombinase with its tamoxifen-dependent activity, the recombination of conditional expression sites, such as Lox sites, DNA can be controlled both spatially and temporally by administration of tamoxifen to the animal.

The invention also relates to the offspring of the transgenic non-human animals of the invention. These offspring may be obtained by crossing a transgenic animal of the invention with mutant animals or models of disease.

In a further embodiment of the invention, there is provided a method for screening molecules of interest to assay their capacity in modulating Ca2+ transients, wherein said method comprises:

a) detecting the dynamics of Ca2+ by the method of optical detection of the invention in a transgenic animal expressing a recombinant polypeptide sensitive to calcium concentration,
b) administering or expressing the molecule of interest into said transgenic animal,
c) repeating step a), and
d) comparing the location, the dynamics, and optionally the quantity, of Ca2+ before and after injection, wherein a variation in the location, the dynamics and/or the quantity of Ca2+ is indicative of the capability of the molecule to modulate Ca2+ transients.

This invention also provides a recombinant peptidic composition capable of being expressed in vivo in a non-human animal by a polynucleotide encoding GFP, aequorin, and a peptide or a protein capable of targeting said recombinant peptide into a cellular domain. The peptidic composition is involved in the visualization or the quantification of Ca2+ changes in a cell, group of cells, subcellular domain or tissue of interest.

This invention provides means to genetically target the bioluminescent reporter, GFP-Aequorin, to different microdomains including those important in synaptic transmission. GFP-Aequorin has an excellent signal-to-noise ratio and can be targeted to proteins or to cellular compartments without perturbing photoprotein function. The invention therefore, enables 'real-time' visualisation of localised Ca2+ dynamics at molecular, cellular, tissue and whole animal level or in dissociated cell cultures, excised tissues, acute and organotypic cultures or living animals.

The reporters of the invention enable selective detection of subcellular or high. Ca2+ concentration microdomains. The genetically encoded bioluminescent Ca2+ reporter, GFP-Aequorin, can therefore be used to optically detect synaptic transmission and to facilitate the mapping of functional neuronal circuits in the mammalian nervous system.

Whole-animal bioluminescence imaging represents a very important non-invasive strategy for monitoring biological processes in the living intact animal. To date, applications describing in vivo imaging of cellular activity with use of bioluminescent reporters have been almost exclusively undertaken with the luciferin-luciferase system from the firefly. The approach takes advantage of the luciferase reporter system for internally generated light linked to specific biological processes. Bioluminescent reactions usually involve the oxidation of an organic substrate (luciferin or chromophore). Light is generated when cells expressing the luciferase are combined with the substrate, luciferin (peak at 560 nm). Both ATP and O2 are required for the light reaction to take place. As these reporters have been developed to emit light shifted in the red at longer wavelengths, the light produced is less absorbed by tissue, making this technology ideal for following tumour progression or infection.

The aequorin based system offers alternative applications to the luciferase based reporter system for BLI. Light is generated in the presence of Ca2+ and the substrate, coelenterazine. In contrast to the luciferin-luciferase system, the Ca2+ dependent light emission of GFP-aequorin (peak at 515 nm) does not require exogenous O2. In contrast, molecular O2 is tightly bound and the luminescence reaction can therefore take place in the complete absence of air. Therefore, the bioluminescence kinetics of the photoprotein is not influenced by the oxygen concentration. The second feature of aequorin is that the light intensity can be increased up to 1 million fold or more on the addition of calcium. The coelenterazine-GFP-aequorin system therefore enables a specific analysis of Ca2+ activities and can be more suitable than the firefly system as a reporter, because it does not require the co-factors ATP and Mg2+. Given that the luciferase reaction results in the emission of red light, it is more suited for deep tissue analysis and therefore ideal for following infectious process or for following tumor progression. However the aequorin based system, can be utilized to monitor Ca2+-dependent biological processes with spatial and fine temporal resolution at more superficial tissue sites (analysis of Ca2+ signal in the mammalian cortex, in skeletal muscles or in skin). With the development of new instrumentation, the GFP-aequorin-coelenterazine system could be imaged in deep tissue layers in the same manner as the luciferase-luciferin system. Whole animal in-vivo imaging of the GFP-aequorin-coelenterazine system can therefore allow to investigate dynamic biological processes in living animal models of human biology and disease.

The inventors have developed transgenic mice expressing different GFP-aequorin reporter polypeptides. The expression of the nucleic acid encoding this recombinant polypeptide of the invention is driven by appropriate transcriptional and/or translational elements, which preferentially localize upstream of said nucleic acid, but may also localize downstream.

These reporter mice offer several advantages over other non gene-based or gene-based reporters, because they can report non-invasively multiple activities in living samples and can be realized in-vivo. A preferred embodiment is a transgenic mouse expressing mitochondrially targeted GFP-aequorin, where mitochondrial Ca2+ activities can be monitored by bioluminescence imaging and GFP fluorescence can be visualized to localize reporter expression and to study specific morphological characteristics. Mitochondrial function is a useful biosensor of cellular activities, particularly for following pathological processes.

Transgenic animals expressing GFP-aequorin reporters could be used for developing diagnostics or for screening new drugs or for evaluating therapeutic response in preclinical trials. Transgenic animals expressing GFP-aequorin reporters could also be crossed with transgenic animal models of disease in order to study pathological processes. For example, transgenic mice expressing mitochondrially targeted GFP-aequorin in all cells or selected cell types can be crossed with transgenic mouse models of Alzheimer's disease to assess pathological processes, develop new diagnostics or evaluate therapeutic response in preclinical trials. Excised tissues and/or dissociated cells derived from transgenic animals expressing GFP-aequorin reporters, can also be applied in high-throughput screening assays for discovery of new drugs, or for assessing activities of existing drugs or to evaluate therapeutic response in preclinical trials or to develop diagnostics.

A problem to be solved in the construction of a transgenic animal is the expression of the inserted transgene, that must be sufficiently efficient for the production of the encoding protein. This may be carried out by the insertion of the polynucleotide encoding the recombinant protein sensitive to calcium concentration or the corresponding DNA construct in a transcriptionally active region of the genome of the animal to transform, or by reconstituting a particularly favourable environment ensuring a correct gene expression, such as a reconstituted HPRT locus. The insertion is carried out having recourse to any technique known from the skilled person in the art, and particularly by homologous recombination.

Another problem to face is the specific expression of this recombinant protein in tissue, organs or cell types. This can be achieved by using recombination system comprising conditional expression sequences and corresponding recombinases such as endonuclease. Particular conditional xpression sequences are Lox sites and the corresponding endonuclease is Cre, that is preferentially expressed under the control of a cell- or tissue-specific promoter.

In vivo imaging of GFP-aequorin according to the invention has been shown to be non-invasive, and can be used to monitor physiological processes, pharmacokinetics, pathological and other aspects of biomolecular processes occurring functions in the living animal. Detection of Ca2+ could be used to assess and monitor many different cellular signaling pathways in the context of studying different pathologies, drug effects and physiological processes. Detection of Ca2+ is a useful diagnostic in many pathological conditions, including, cancer, infection processes, neuropathological disesases, muscle disorders (e.g. muscular dystrophy), for treatment and diagnosis of cardiovascular disorders. GFP-aequorin technology could also be applied to all mammals and other animals, e.g. worms (e.g. Nematodes), fish (e.g. Zebrafish), frogs (*Xenopus* sp.) and flies (*Drosophila* sp.).

For instance, calcium imaging offers an alternative approach for monitoring liver, heart or brain activity. For example, Ca2+ signals are linked to the electrical activity of neurons and to the propagation of activity via glial to glial, glial to neuron, neuron to neuron or neuron to glial cell signaling (e.g. chemical and gap-junctional coupling). Furthermore, Ca2+ is involved in many intracellular signalling pathways. Spatiotemporal profiles of Ca2+ in cellular microdomains regulate the activation of key signalling pathways. Hence, by genetically localizing a reporter to nanodomains or microdomains, cellular events can be monitored in real-time at the molecular level, even when there is very little spatial resolution, as it is the case in whole animal imaging. Described hereafter are multi-functional reporter mice for in-vivo, ex-vivo and in-vitro imaging in research and development applications.

Figure 2:
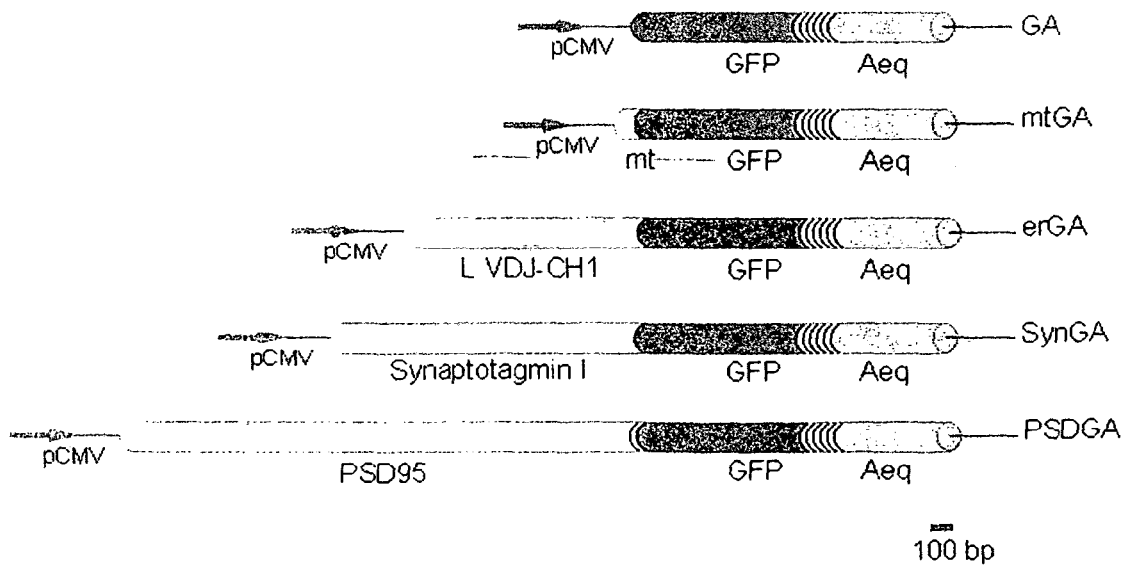
FIG. 2: Schematic representation of the different GA chimaeras for cell specific targeting. The white asterisk shows the position of the (Asp-119→Ala) mutation in aequorin, reducing the $Ca^{2+}$ binding affinity of the photoprotein, as described by Kendall et al, 1992. GA represents non-targeted GFP-Aequorin, denoted G5A, and containing a flexible linker between the two proteins (GA and SynGA are declared in the application PCT/EP01/07057). mtGA, mitochondrially targeted GFP-aequorin by fusing GA to the cleavable targeting sequence of subunit VIII of cytochrome c oxidase; erGA, GFP-aequorin targeted to the lumen of the endoplasmic reticulum after fusion to the N-terminal region of the immunoglobulin heavy chain, PSDGA, fusion of GFP-aequorin to PSD95 for localised targeting in postsynaptic structures. All constructs are under the control of the human cytomegalovirus promoter (pCMV).

Material and Methods
Construction of Targeted Vectors (FIGS. 1 and 2)

Figure 11A:
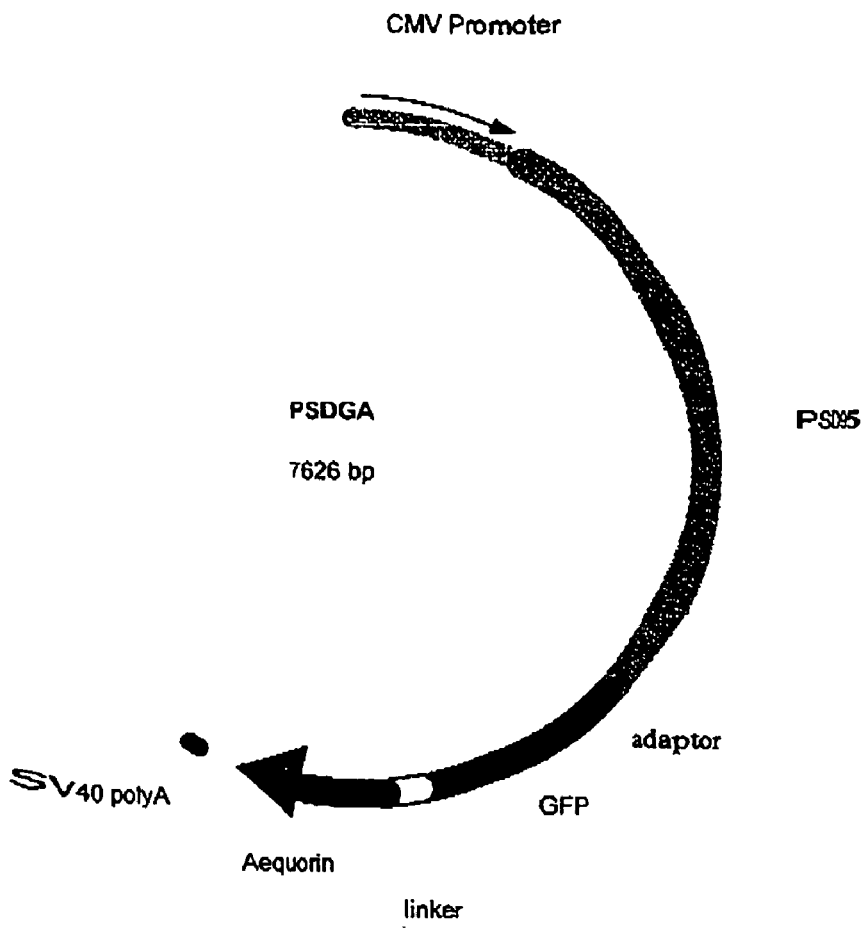
FIG. 11: (A) Map of the PSDGA vector and (B) the coding sequence (SEQ ID NO: 3; and corresponding protein sequence, SEQ ID NO: 4) of the insert comprising PSD95 (nucleotide positions 616 to 2788), an adaptor (capital letters), GFP (2842 to 3555), a linker (3556 to 3705, capital letters) and the aequorin (3706 to 4275).

GA represents non-targeted GFP-Aequorin denoted G5A containing a 5-repeat flexible linker between the two proteins. Construction of GFP-Aequorin (GA) and Synaptotagmin-G5A (SynGA) has been described previously (WO 01/92300). For targeting of the GFP-Aequorin chimaera to a post-synaptic domain, we created a fusion between the N-terminal region of PSD95 and GA. In this construction the full length of the PSD95 gene (FIG. 12) was cloned HindIII/EcoRI into pGA (C.N.C.M. I-2507, deposited on Jun. 22, 2000) to give the plasmid, PSDGA. A flexible linker was then added between PSD95 and the start of GFP, composed of the following sequence 5' A ATT CGG TCC GGC GGG AGC GGA TCC GGC GGC CAG TCC CCG C '3 (SEQ ID NO: 2; FIG. 11).

Figure 12A:
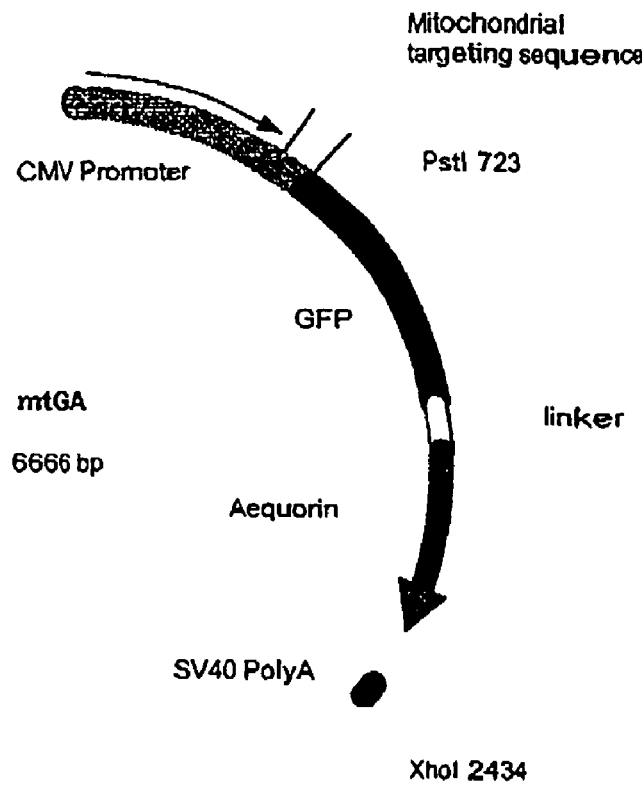
FIG. 12: (A) Map of the mtGA vector and (B) coding sequence (SEQ ID NO: 5; and corresponding protein sequence, SEQ ID NO: 6) of the insert comprising the cleaveable targeting sequence of subunit VIII of cytochrome C oxidase (nucleotide positions 636 to 722, capital letters), GFP (741 to 1454), a linker (1455 to 1604, capital letters) and the aequorin (1605 to 2174).
Figure 13:
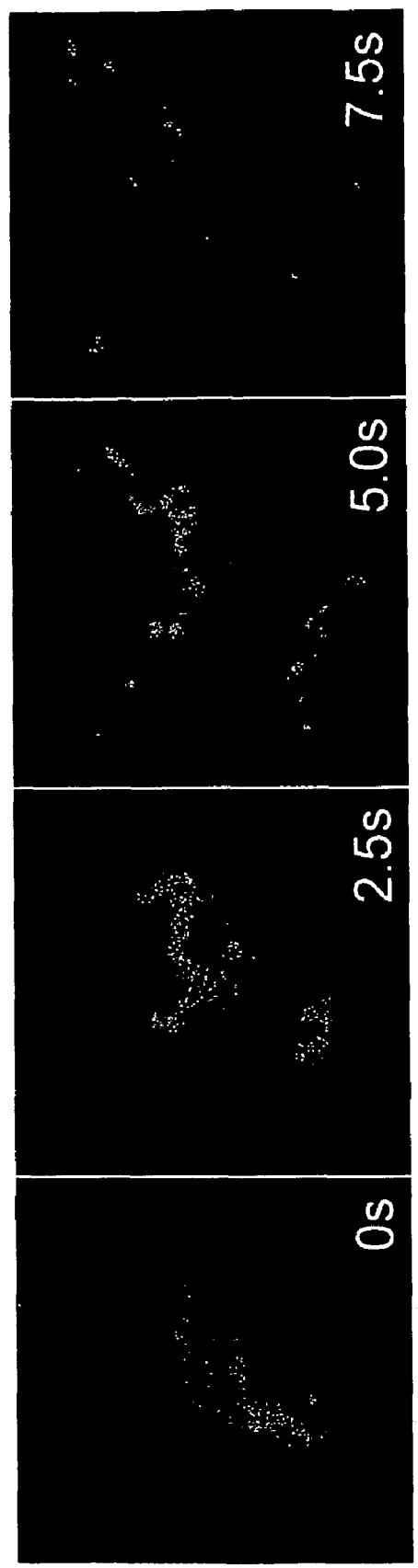
FIG. 13. Detection of dynamic activity in single-cells when GFP-aequorin is localized to specific cellular domains. Ca2+-induced bioluminescence in a cortical neuron transfected with PSDGA. The propagation of Ca2+ waves and response profiles produced subcellularly were shown to be highly complex. The IPD camera used in these studies provides µs time resolution and integration times are specified only for on-line visualization. Working with a highly variable time scale enables the full extent of the spatiotemporal properties of Ca2+ activity to be investigated, which is itself a physiological parameter. Scale bar=20 µm.
Figure 14:
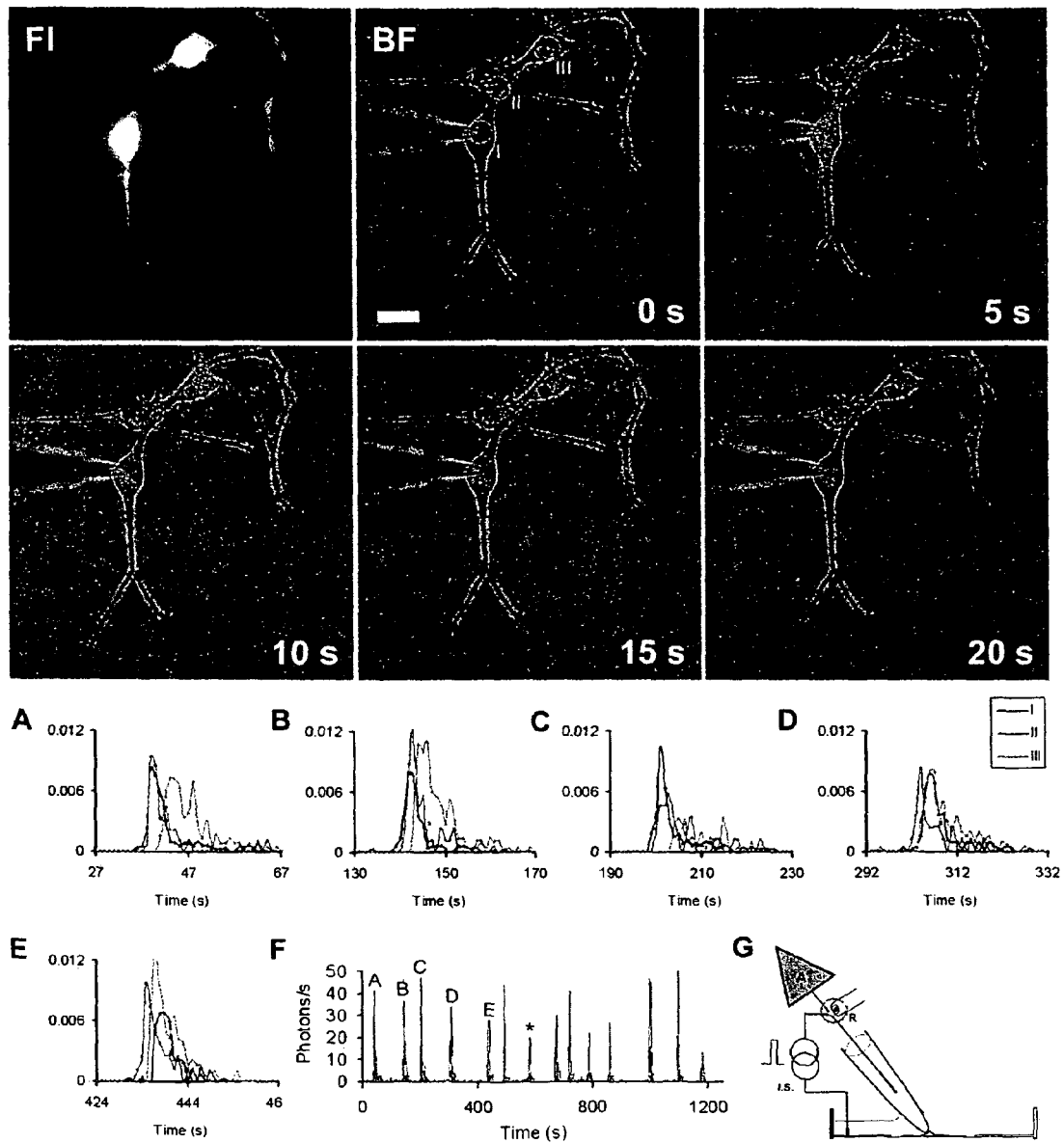
FIG. 14. Electrically induced Ca2+-oscillations in hippocampal neurons. Fluorescence (FI) and brightfield images (BF) from a 24 day old culture, whereby a patch-like pipette (7-10 MΩ) connected to a pulse generator was brought in gentle contact with the somatic region of the 'lower' cell shown in the image. Scale bar=20 µm. Light emission induced by a single 2 ms electrical pulse (A) is shown in 5 s frames and in A to E graphs shown on the lower panel. The applied voltage is given on each graph (polarity refers to the battery side the pipette is connected to). The photon images are superimposed with the brightfield image. The fractional light emission (L/Lmax) from the 3 regions indicated in BF appears in the graphs A to E and correspond to successive electrical stimulations. (F) All Ca2+ transients recorded in each region of interest during a 20-minute period are shown as a function of time. The asterisk indicates the first of a series of spontaneously occurring transients. (G) Schematic diagram of the electrical arrangement. I.S, isolated stimulator, R, electrical relay, A, patch amplifier head. Neurons were transfected with a viral vector containing the GFP-aequorin gene (see Methods for more detail).
Figure 15:
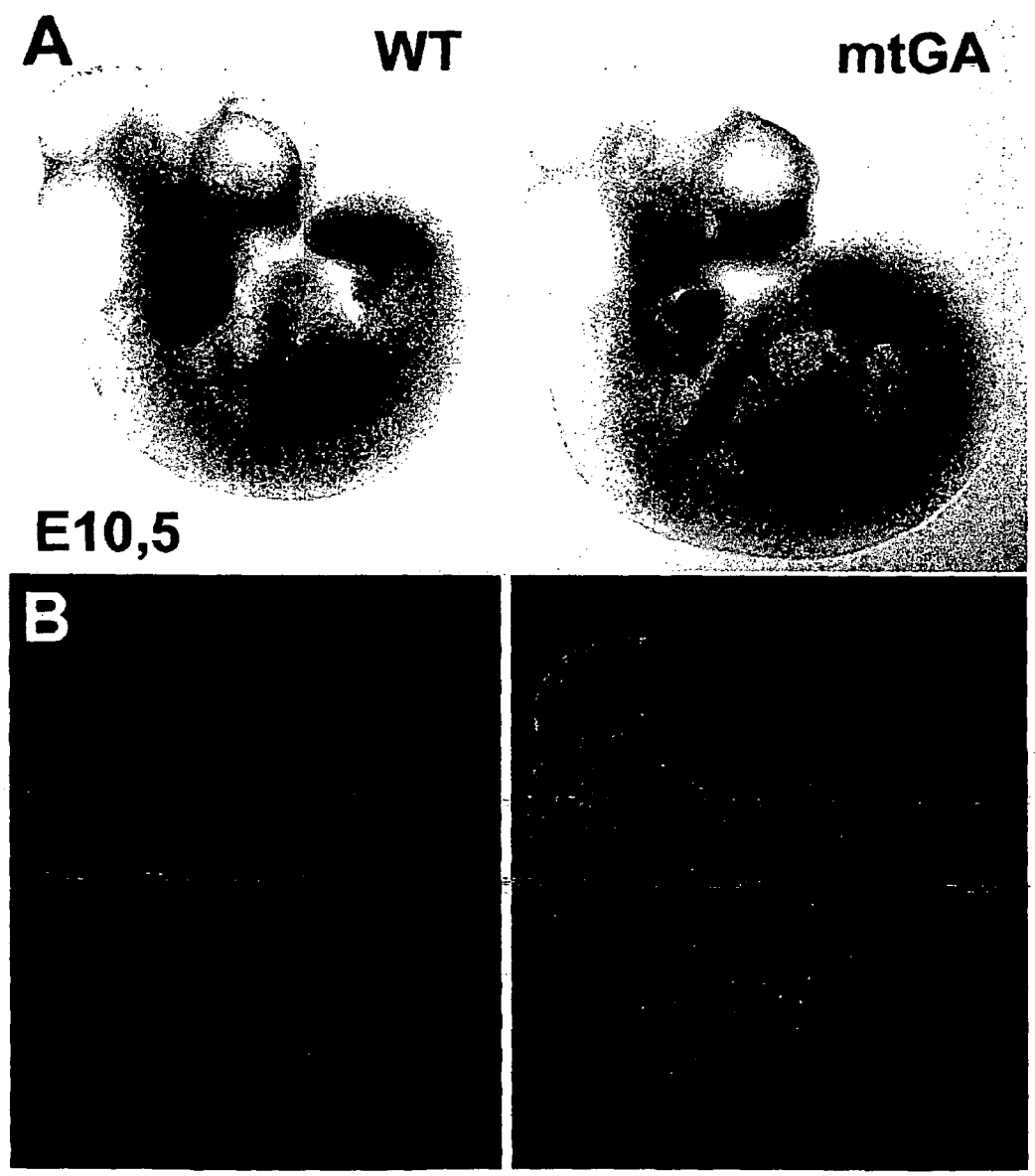
FIG. 15. GFP fluorescence of 10.5 day old transgenic embryos vs wildtype embryos. Chimeric mtGA (pCAG-Lox-stop-Lox-mtGA) mice were crossed with a PGK-CRE mouse to activate expression of the transgene in all cells of the body from the beginning of development. (A) Brightfield images of a 10.5 day old embryo from wild-type and transgenic mice; (B) Corresponding GFP fluorescence images. No phenotypic abnormalities are apparent.
Figure 16:
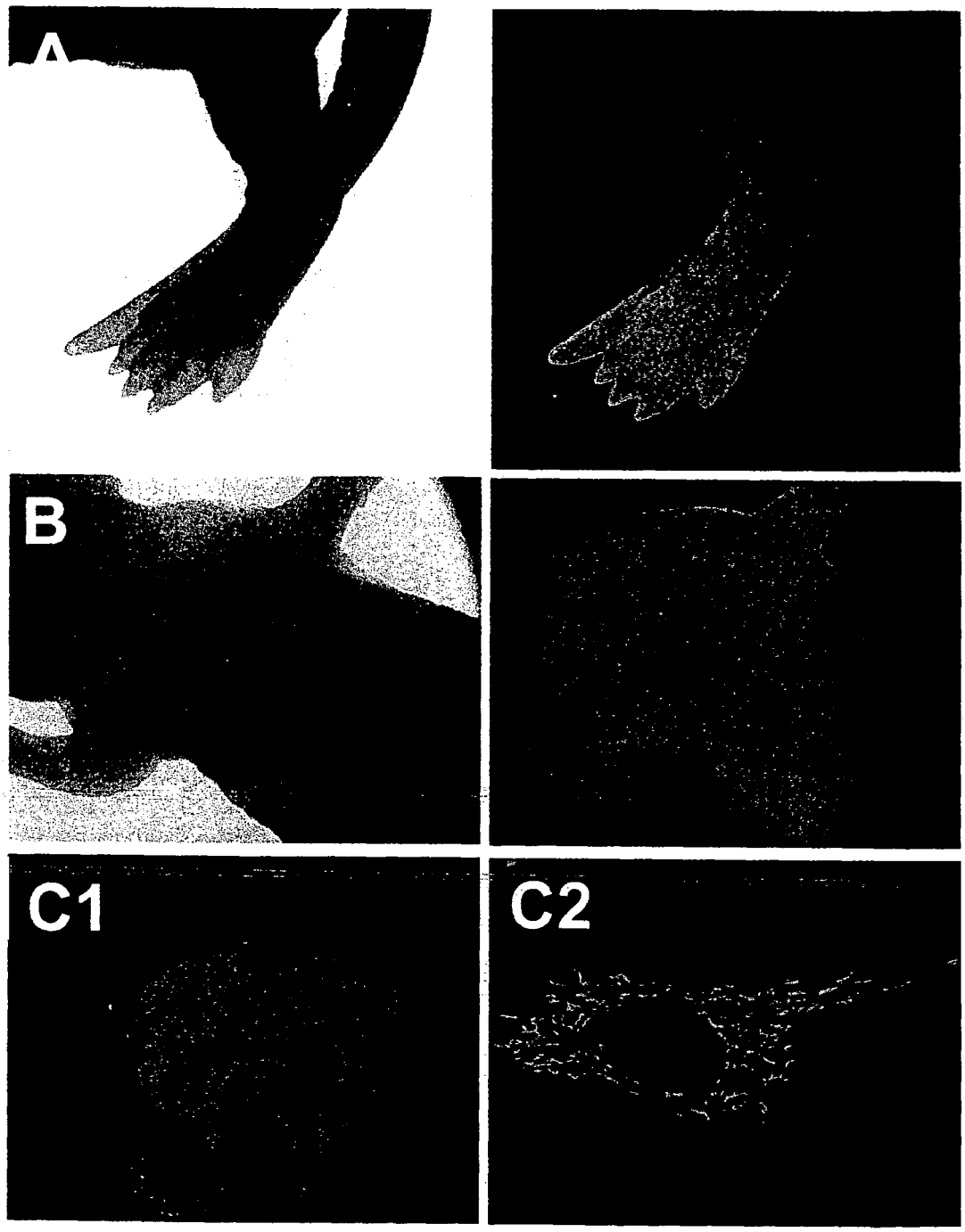
FIG. 16. GFP fluorescence in neonatal transgenic mice expressing the mitochondrially targeted GFP-aequroin protein in all cells. Brightfield and corresponding GFP fluorescence images of mtGA mouse after activation of the transgene (by crossing with PGK-CRE) in all cells of the body from the beginning of development. (A) Foot, (B) Dorsal view of the upper body, (C1) Dorsal view of the head and (C2) targeting of mtGA in cortex of P1 mtGA mouse. No physical or behavioral abnormalities are apparent in newborn or adult mice.

The GFP-Aequorin chimaera (GA) has been targeted to the mitochondrial matrix by cloning the reporter gene into the Pst I/xho I sites of the vector containing the cleavable targeting sequence of subunit VIII of cytochrome c oxidase (pShooter, Invitrogen) to give the plasmid mtGA (FIG. 12). GA was also targeted to the ER lumen, by cloning in frame to the N-terminal region of the immunoglobulin (IgG) heavy chain gene, which consists of the leader sequence, VDJ and the CH1 domains. The coding sequence for the N-terminal region of the IgG heavy gene was removed with Nhe I and Hind III from the plasmid erAEQmut, which was kindly provided by Dr J Alvarez (Universidad de Valladolid, Spain). The gene insert was ligated in frame to the N-terminal of the G5A gene in the pEGFP-C1 vector (Clontech), to give the plasmid erGA.

A mutation (Asp-407→Ala) to reduce the $Ca^{2+}$ binding affinity of the photoprotein (Kendall et al., 1992), wherein the numbering corresponds to the position of the mutation in Aequorin in the GA construct, was generated by PCR in each of the targeted GA constructs to give the plasmids, mtGAmut, erGAmut, SynGAmut and PSDGAmut. All constructs are under the control of the human cytomegalovirus promoter (pCMV). All sequences have been verified by DNA sequencing.

Single-Cell Bioluminescence Studies (FIGS. 5-9)

Cultures were plated on to glass-bottomed dishes and mounted to a stage adapter on a fully automated inverted microscope mounted in a black-box. GFP-Aequorin was reconstituted with 2.5-5 μM coelenterazine for 30 minutes at 37° C. Incubation of cells with coelenterazine that had been transfected with SynGA was undertaken at room temperature to reduce the consumption of the photoprotein during the reconstitution process. Cells were perfused with tyrodes buffer. Prior to bath application of NMDA, cells were perfused for 1 minute without $Mg^{2+}$. All recordings were made at room temperature (22-25° C.). Cells having a cell soma diameter between 10-15 μm, which were phase bright without granular appearance, were selected for measurements. Cells transfected with SynGA and reconstituted with wildtype coelenterazine, regularly displayed a low level of bioluminescence activity at resting state. Activity appeared to be homogenous and more evident in the cell soma region. This suggests that GA targeted in this fashion, is within a domain endowed with a high concentration of $Ca^{2+}$. On two occasions, cells transfected with PSDGA, showed spontaneous activity that was localised to dendritic regions.

Figure 10:
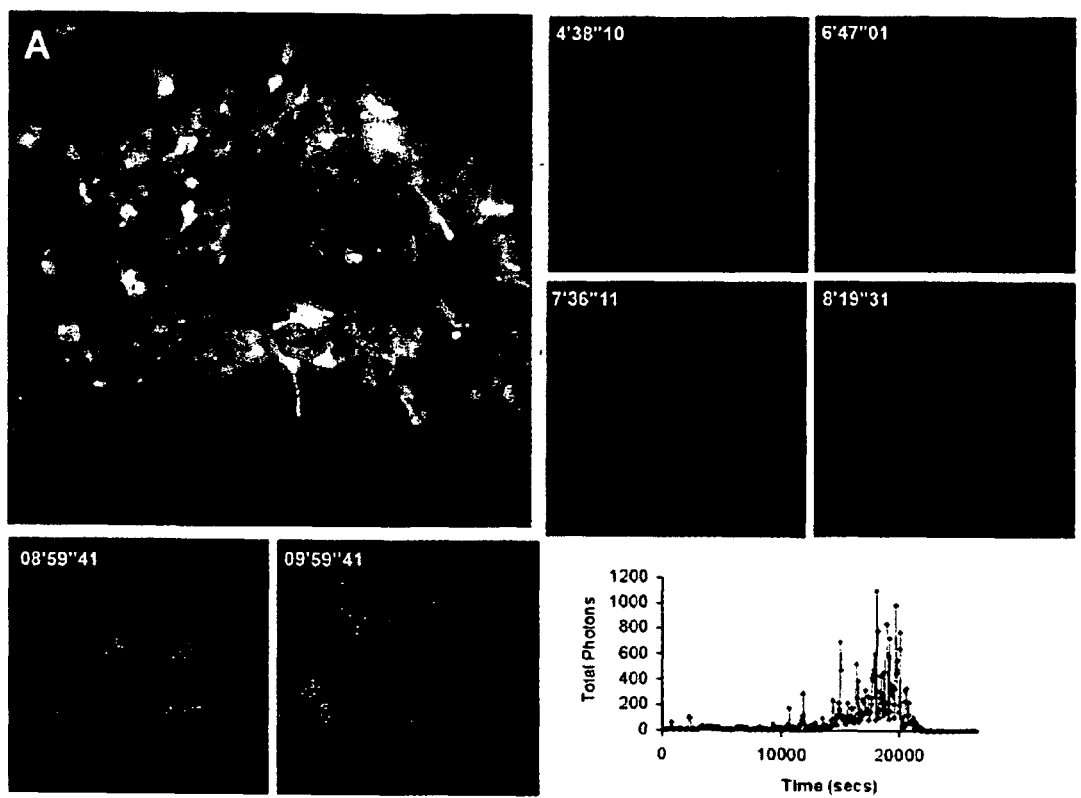
FIG. 10: Long-term bioluminescence imaging of Ca2+ dynamics in an organotypic hippocampal slice culture from neonatal mouse brain, infected with an adenoviral-GFP-Aequorin vector. (A) GFP fluorescence shows individual cells expressing the Ca2+ reporter. Activity was recorded for a period of approximately 9 hours before cell death became apparent as indicated by a large increase in bioluminescence activity and loss of fluorescence. Fluorescence images were taken periodically (each 30 min) throughout the acquisition. Representative photon images are shown as well as the corresponding graphical data (last 7 hours). Background <1 photon/sec.×10.
Figure 19:
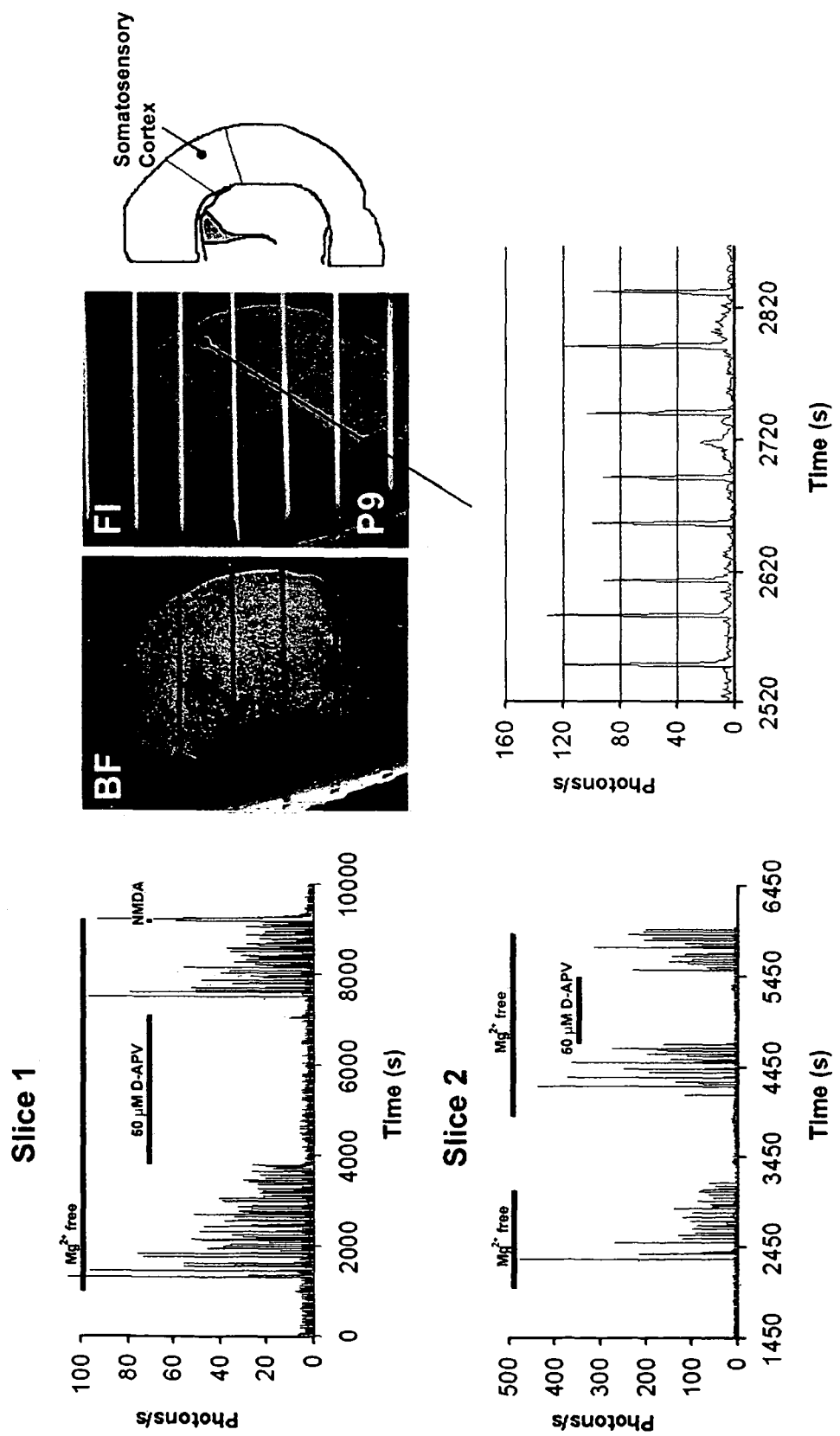
FIG. 19. Synchronized oscillations of mitochondrial Ca2+ transients in the somatosensory cortex of the immature mouse brain. (BF, brightfield & FI, fluorescence images) Organotypic slices (coronal) were cut from P4 transgenic mice expressing the mitochondrially targeted GFP-aequorin in all cells of the brain. Slices were kept in culture for 4-5 days before imaging. After incubation with coelenterazine (wt), slices were perfused in a buffer (with or without Mg2+). The results for two slices are represented, showing that removal of Mg2+ from the buffer generates Ca2+ oscillations that are detected from within the mitochondrial matrix and that are completely and reversibly blocked by the NMDA antagonist, D-APV (50 µM). Photons were collected from a 550 µm2 region corresponding to somato sensory cortex in layers I-III/IV and V of the cerebral cortex.

Imaging $Ca^{2+}$ Dynamics in Organotypic Slice Cultures (FIGS. 10 and 19)

Organotypic hippocampal slices were prepared from 4-5 day old mice pups. Briefly, brains were rapidly removed in ice-cold Hanks buffer and sliced into 200 μm slices with a tissue chopper. Hippocampal slices were identified using a stereo microscope and transferred into sterile transwell collagen coated chambers (12 mm diameter, 3.0 μm pore size). Slices were maintained in Neurobasal medium supplemented with B27 at 37° C., in a humidified atmosphere containing 5% $CO_2$. Slices were infected at day 9 with the Adenovirus-GFP-Aequorin vector and maintained in culture for a further 4 or 5 days before imaging. At this stage, slices appeared healthy and individual cells could be clearly distinguished by GFP fluorescence. After incubation with coelenterazine, slices could be maintained on an inverted microscope at room temperature for up to 9 hours at which time cell death became apparent, indicated by large increases in bioluminescence activity and loss of cellular fluorescence. Because light excitation is not required to detect the $Ca^{2+}$ reporter, long-term imaging can be performed without causing photodynamic damage. Imaging over long periods is continuous. It is not necessary to select an integration period. Background is extremely low, less than 1 photon/sec in a 256×256 pixel region (665.6×665.6 μm). In some experiments, coronal 400-450 μm slices from the somatosensory cortex of transgenic mice were cut using a vibratome and placed in culture for 4-5 days before imaging. Slices were perfused with ACSF bubbled with 95% $O_2$ and 5% $CO_2$. Following 1 hour of incubation, slices were perfused with Mg2+ free ACSF. Recordings were made at room temperature (25-28° C.). Drugs were added via the perfusate.

Construction of Transgenic Animals (FIGS. 15-23)

We have genetically engineered new reporter molecules, whereby GA is targeted to sub-cellular domains in transgenic mice. The GA transgene can be expressed in any cell type and/or at any stage of development. Expression has been made conditional by using a Lox-stop-Lox sequence immediately after the strong promoter, β-Actin (CAG). Selection of the expressing cells is made by using an appropriate endonuclease Cre, driven by specific promoters. The time at which the transcription will be started will be realized by injecting tamoxifen when the gene Cre-$ER^{T2}$ will be used. Finally, to have the possibility to express in any cell, the transcription unit has been introduced by homologous recombination in ES cells in the reconstituted HPRT locus (X chromosome) to minimize the influence of the integration site on the level of expression. In the experiments shown here, a PGK Cre transgenic mouse that activates the GA transgene in very early embryo was used.

Recombinant viruses containing CRE that are under the regulation of a cell specific promoter can also be used. Mice have been constructed by injection of genetically modified ES cells into blastocysts.

Figure 18:
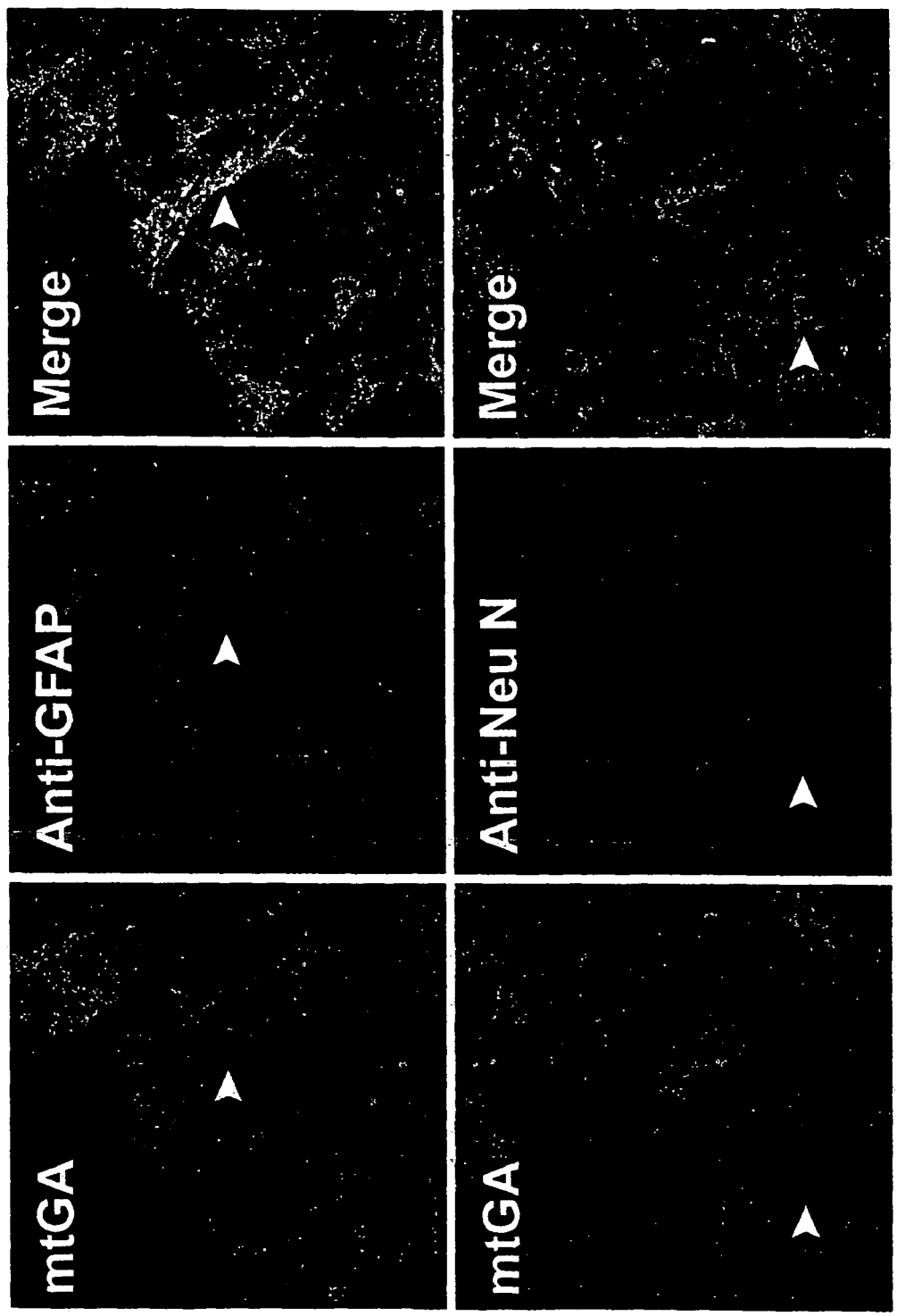
FIG. 18. Confocal analysis of mtGA in cortex of transgenic animals expressing the transgene in all cells. Transgenic mice were crossed with PGK-CRE mice for activated expression of the mtGA transgene in all cells of the living animal. Organotypic slices were prepared from P4 mouse and kept in culture for 4 days before undertaking experiments to detect Ca2+-induced bioluminescence. At the completion of the experiment, slices were fixed and then stained for GFAP (for detection of glial cells) and NeuN (for detection of neurons). Both antibodies colocalize to expression of the mtGA transgene. GFP fluorescence shows expected expression patterns of the GA reporters after fusion to the signal peptide of cytochrome c for targeting to the mitochondrial matrix (mtGA). These results show that the mtGA transgene is expressed in all cells of the brain when transgenic mtGA reporter mice are crossed with PGK-CRE mice, which activates Cre in all cells.

Immunolocalisation Studies with mtGA (FIG. 18)

Cortical neurons or brain slices expressing the mitochondrially targeted GFP-aequorin reporter were fixed for 20 min in 4% formaldehyde in PBS at RT. After washing with PBS, cell membranes were permeabilised with PBS containing 0.1% Triton-X 100 and BSA. Cells were then incubated at RT for 1-2 hours with primary antibodies. Targeting was compared to anti-cytochrome c (1:500; BD Biosciences Pharmingen, Calif., USA) and MitoTracker® Red CMXRos (200 nM; Molecular Probes Inc.). The binding of antibodies was determined after incubation for 1 hour in secondary antibodies conjugated to Alexa Fluor®546 (Molecular Probes, Inc.). After washing, cells were mounted on slides in Fluoromount and visualized by confocal analysis. Images were acquired on an Axiovert 200M laser scanning confocal microscope (Zeiss LSM-510; version 3.2) through a 63×/1.4 NA, oil immersion objective using LP560 and BP505-550 filters. The pinhole aperture was set at 98 Tm and images were digitized at a 8-bit resolution into a 512×512 array.

Combined Fluorescence/Bioluminescence Imaging (FIGS. 5-7, 8-10, 13, 14 and 19)

The fluorescence/bioluminescence wide field microscopy system was custom built by ScienceWares, Inc. The system includes a fully automated inverted microscope (200M, Zeiss Germany) and is housed in a light-tight dark box. Mechanical shutters control illumination from both halogen and HBO arc lamps, which are mounted outside of the box and connected via fiber optic cables to the microscope. Low level light emission (photon rate <100 kHz), was collected using an Image Photon Detector (IPD 3, Photek Ltd.) connected to the baseport of the microscope, which assigns an X, Y coordinate and time point for each detected photon (Miller et al., 1994). The system is fully controlled by the data acquisition software, which also converts single photon events into an image that can be superimposed with brightfield or fluorescence images made by a connected CCD camera to the C-port (Coolsnap HQ, Roper Scientific). Any $Ca^{2+}$ activity that is visualised can therefore be analysed in greater detail by selecting a region of interest and exporting photon data. After an experiment has been completed, the recorded movie file can be replayed and data can be extracted according to the users needs. The IPD can provide sub-milisecond time resolution and integration times are not required to be specified for the acquisition. The system we are using has very low background levels of photon counts, <1 photon/second in a 256×256 pixel region.

Calibration of bioluminescence measurements into intracellular $Ca^{2+}$ values in living cells can be performed by in vitro calibration. Intracellular $[Ca^{2+}]$ measurements were made by determining the fractional rate of photoprotein consumption. For in vitro calibration, Neuro2A cells were transiently transfected with the different constructs. After 48 hours, cells were washed with PBS and harvested using a cell scraper. The cell suspension was transferred to a 1.5 ml Eppendorf tube and incubated in an aequorin reconstitution buffer containing 10 mM mercaptoethanol, 5 mM EGTA, and with either the native (wt), n or h coelenterazine 5 μM in PBS, at 4° C. for 2 hours. After 2 hours, cells were washed and resuspended in a hypo-osmotic buffer containing 20 mM Tris/HCl, 10 mM EGTA and 5 mM mercaptoethanol in $dH_2O$ and protease inhibitor, EDTA free (Roche Diagnostics). Cell membranes were further lysed by three freeze-thaw cycles, followed by passing the suspension through a 26 GA needle. 10 μl aliquots of cell lysates containing the reporter protein were dispensed into the wells of white opaque 96-well plates, which contained EGTA buffered solutions having known concentrations of $CaCl_2$ (Molecular Probes, Inc.). Free $Ca^{2+}$ was calculated using the WEBMAXC program (Bers et al., 1994). Luminescence was directly measured using a 96-well plate reader (Mithras, Berthold Tech. Germany). Light was recorded for 10 s, with 100 ms integration after injection of the cell lysate. After 10 s, 100 μL of a 1 M $CaCl_2$ solution was injected into the same well and recording was continued until light returned to basal levels and all of the photoprotein had been consumed (Lmax). Light emission is expressed as the fractional rate of photoprotein consumption, which is the ratio between the emission of light (L, $s^{-1}$) from that time point (defined $[Ca^{2+}]$) and the integral of total light emission from that point until full exhaustion of the photoprotein (Lmax) (saturating $Ca^{2+}$). Experiments were undertaken at 25-28° C.

Electrical Stimulation and Viral Transfection

In some experiments, electrical pulses were delivered to the cell under study via a classical patch pipette (5-10 MΩ), pulled from borosilicate glass (World Precision Instruments, Fla., USA). An electrically operated relay system made within the laboratory, allowed for measurement of the pipette resistance between stimulations delivered by an isolated stimulator (DS2A, Digitimer Ltd, England) (see FIG. 14). The propagation rate of $Ca^{2+}$ waves was calculated by taking the time point corresponding to the half maximum of light emitted after stimulation and dividing by the distance measured between the center of the two regions analysed.

Whole Animal Bioluminescence Detection

Native coelenterazine (4 μg/g of body weight; Interchim France) was introduced by an intra-peritoneal injection into P1-P4 mice. Imaging of mice began 1-1.5 hours after injection of the substrate, coelenterazine. An IVIS® Imaging System 100 Series, which allows real-time imaging to monitor and record cellular activity within a living organism was utilized in these studies to detect local Ca2+ changes at the whole animal level. The system features a cooled back-thinned, back illuminated CCD camera, inside a light-tight, low background imaging chamber. A greyscale surface image of mice was initially acquired by using a 10 cm field of view, 0.2 s exposure time, a binning resolution factor of 2, 16 f/stop (aperture) and an open filter. Bioluminescence images were acquired immediately after the greyscale image. Acquisition times for bioluminescence images ranged from 1-5 seconds, binning 8 & 16, field of view 10 cm; f/stop 1. Relative intensities of transmitted light from in vivo bioluminescence were represented as a pseudocolor image ranging from violet (least intense) to red (most intense). Corresponding grayscale photographs and color luciferase images were superimposed with LivingImage (Xenogen) and Igor (Wavemetrics, Lake Oswego, Oreg.) image analysis software.

Results

Result 1: Targeting of GA to Subcellular Domains.

Figure 4:
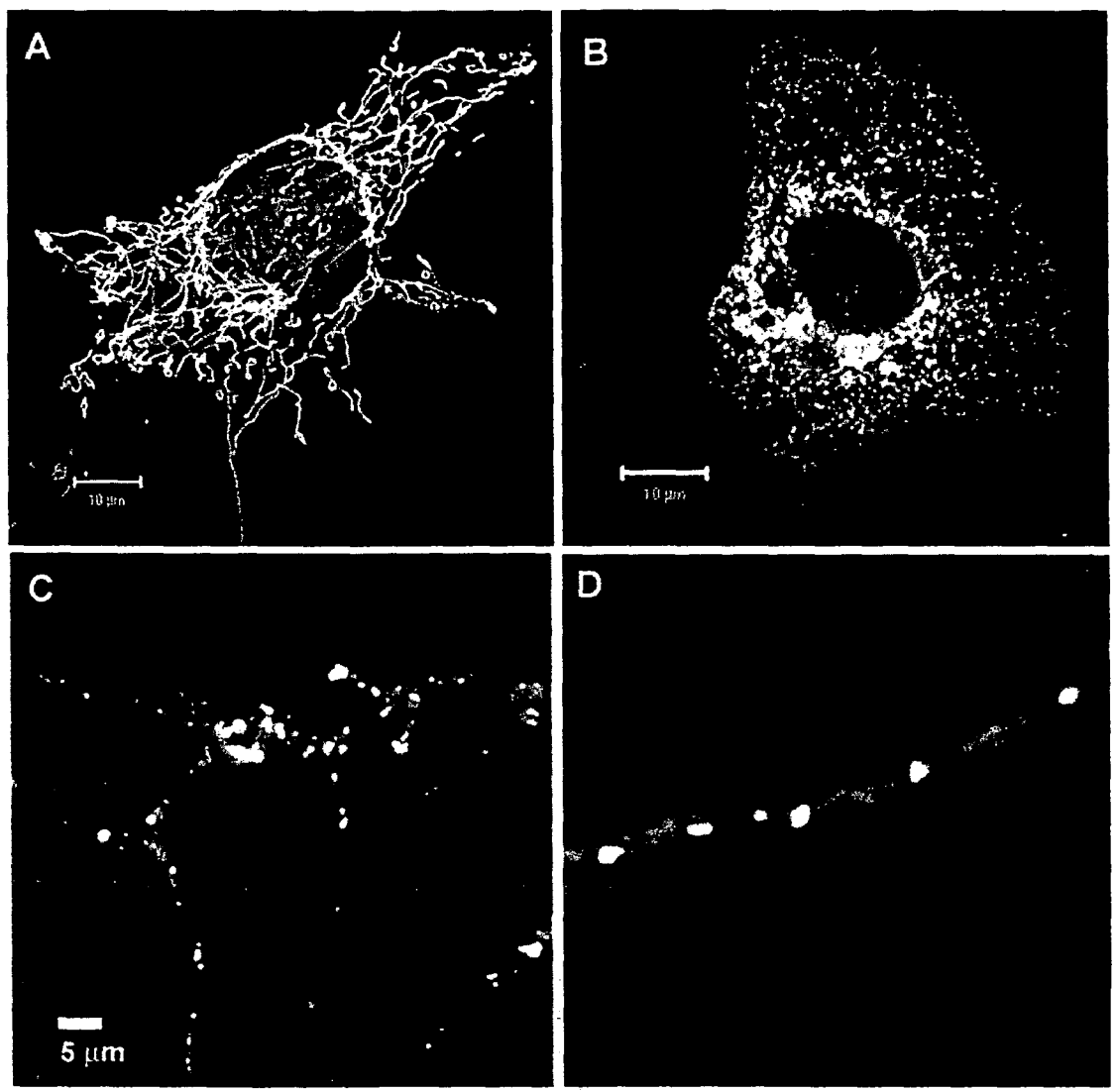
FIG. 4: Confocal microscopy analysis of the different GFP-Aequorin chimaeras targeted to specific subcellular domains. (A) mtGA, GFP-Aequorin is well targeted to the mitochondrial matrix in COS7 and cortical neurons. (B) erGA, GFP-Aequorin is well targeted to the lumen of the endoplasmic reticulum (C) PSDGA, GFP-Aequorin fused to the C-terminus of the PSD95 protein, results in punctate labeling of the $Ca^{2+}$-reporter that resembles targeting of the native protein in dissociated cortical neurons. (D) SynGA, GFP-Aequorin fused to the C-terminus of synaptotagmin I, the synaptic vesicle transmembrane protein, labels synaptic regions. Targeted GA reporters have also been verified by immunohistochemical staining with relevant antibodies.

Different GA reporters were constructed by fusion to a signal peptide or protein of interest with the aim to direct expression into specialized subcellular compartments (FIGS. 1 & 2). GA was targeted to domains that are important in synaptic transmission: mitochondrial matrix, endoplasmic reticulum, synaptic vesicles and the post-synaptic density. Confocal analysis shows expected expression patterns of the GA reporters after fusion to the signal peptide of cytochrome c for targeting to the mitochondrial matrix (mtGA), to IgG heavy chain for targeting to the lumen of the ER (erGA), to synaptotagmin I protein for targeting to the cytosolic side of the synaptic vesicle membrane (SynGA) or to PSD-95 protein for targeting to the postsynaptic density (PSDGA) (FIG. 4) (see Christopherson et al., 2003; Conroy et al., 2003).

Result 2: GA Reports $Ca^{2+}$ Concentrations with Single-Cell Resolution.

Figure 5:
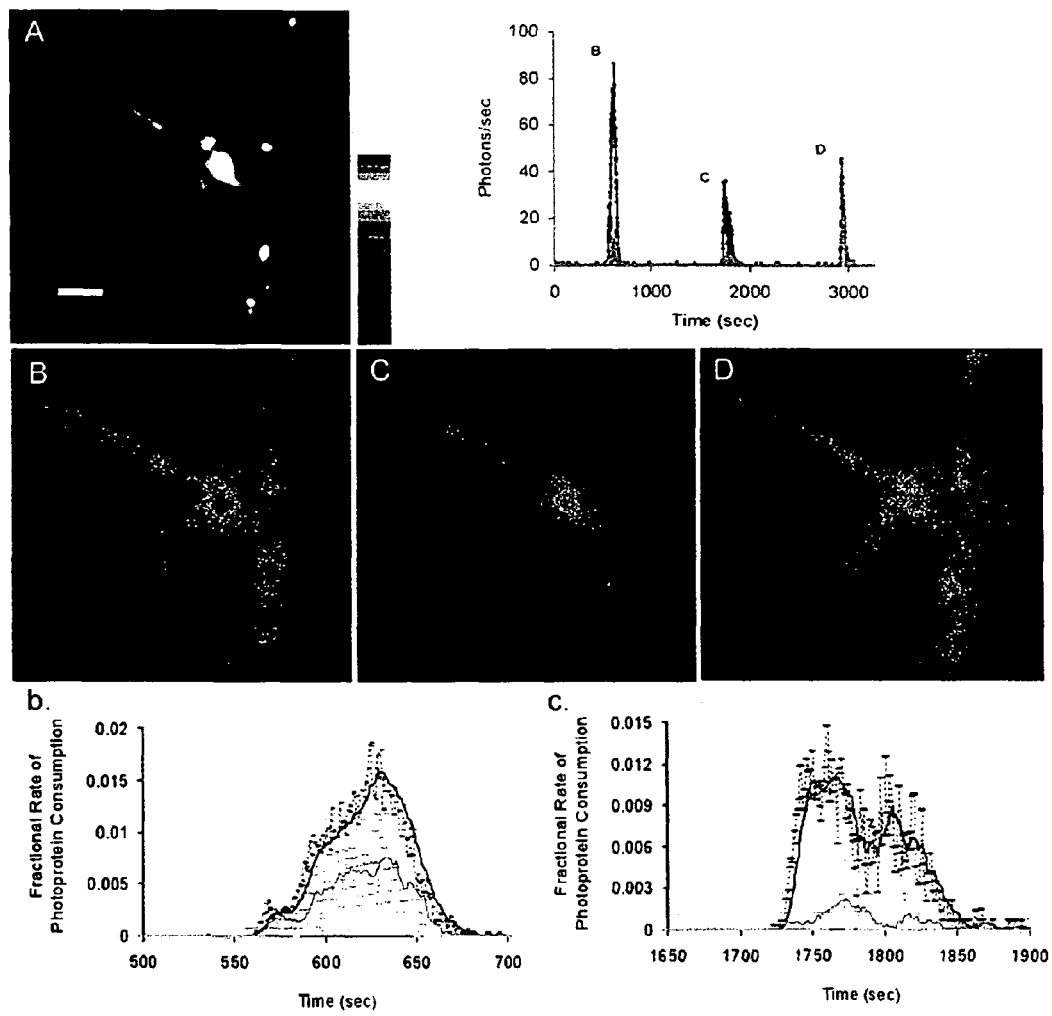
FIG. 5. Cortical cells transfected with the non-targeted version of GFP-Aequorin. GFP-aequorin were reconstituted with the high affinity h version of coelenterazine. (A) GFP fluorescence shows homogenous distribution of the Ca2+ reporter. Ca2+ induced bioluminescence and corresponding graphical data after application of (B, b.) 100 μM NMDA and (C, c.) 90 mM KCl to a single cortical neuron transfected with GA. (D) High Ca2+ solution containing digitonin was added at the end of the experiment to quantitate the total amount of photoprotein for calibration of the Ca2+ concentration. Images were obtained at room temperature (23-25° C.) using a ×40 objective with a 1.3 NA. Scale bar=15 μm Changes in [Ca2+] as indicated by the number of photons detected, are coded in pseudocolor (1-5 photons/pixel), where dark blue represents low and red represents high pixel counts.

We began these studies with the non-targeted GA, which distributes homogenously in neurons (FIG. 5). After reconstitution of GA with h coelenterazine (a high affinity version of the luciferin), stimulation with NMDA (100 μM) and KCl (90 mM) produced a robust signal in cortical neurons (FIGS. 5B & C). This is the first time that $Ca^{2+}$ responses in small mammalian neurons have been directly visualised at the single and subcellular level with a bioluminescent reporter. Application of digitonin and high $Ca^{2+}$ at the end of the experiment indicates that there was still sufficient photoprotein remaining (FIG. 5D). High $Ca^{2+}$ and digitonin were also added at the end of the experiment to measure the total available GFP-aequorin (Lmax) for normalizing the data (see definition of Lmax in the methods section).

Result 3: Optical Detection of GFP-Aequorin Targeted to a Synaptic Protein Associated with Calcium Signaling.

Microdomains of High Ca2+ are Detected with Targeted GFP-Aequorin Reporters after Stimulation of Cortical Neurons.

Example 1

Figure 6:
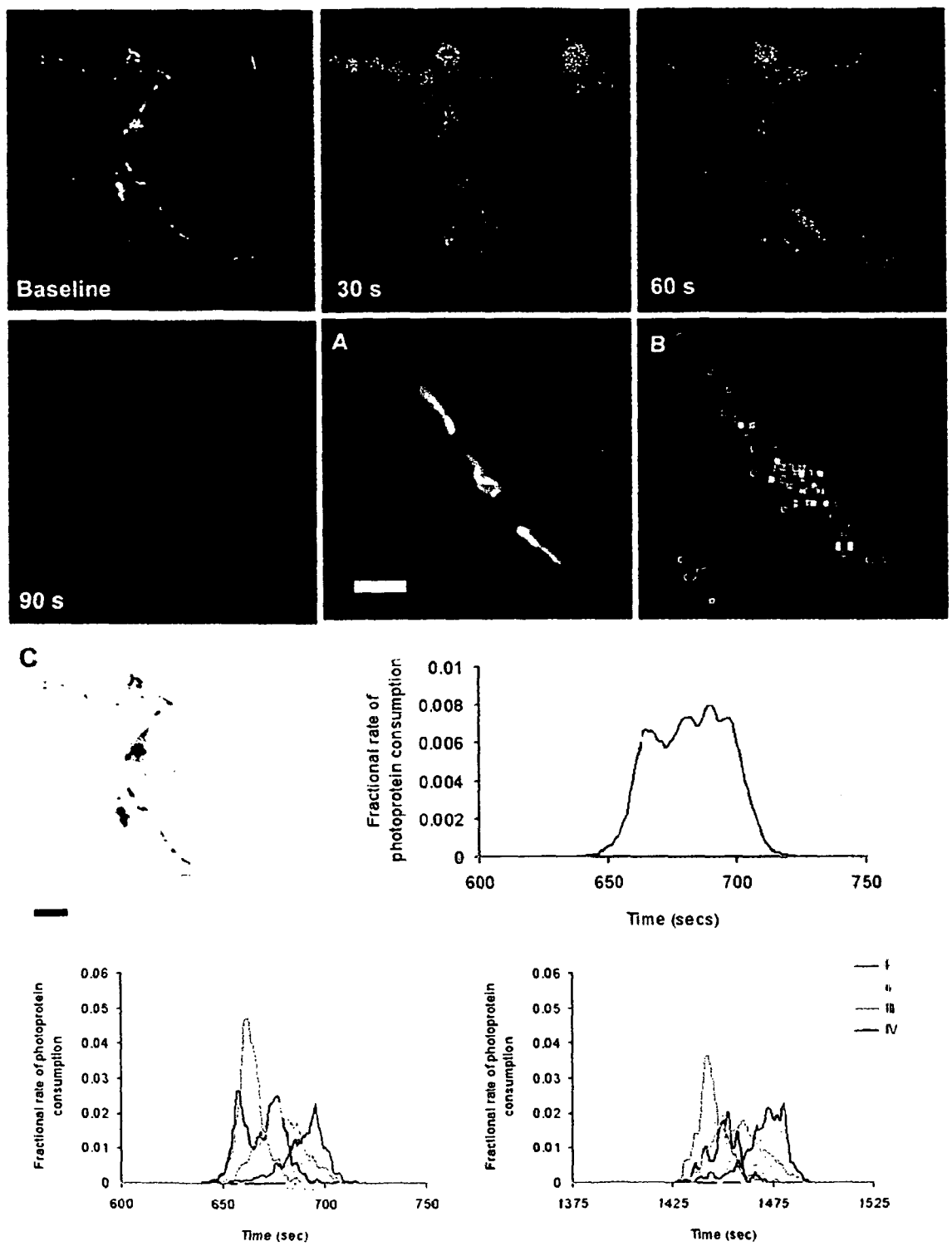
FIG. 6: NMDA induced influx of Ca2+ in a cortical neuron transfected with mtGA. GFP enables the expression patterns of the Ca2+ reporter to be visualized by fluorescence microscopy as shown in the first image, baseline, where the GFP fluorescence image has been superimposed with the photon image prior to stimulation. Using a highly sensitive image photon detector (IPD), Ca2+ induced bioluminescence was recorded after application of NMDA (100 μM. IPD detection provides a high degree of temporal resolution and a moderate degree of spatial resolution. See the zoomed region showing a comparison of the spatial resolution between (A) the CCD fluorescence image, scale bar=5 μm and (B) the IPD photon image. (C) GFP fluorescence image showing regions of interest and corresponding graphical data. Scale bar=10 μm). A graph is represented also for the whole cell response. Each photon image represents 30 seconds of accumulated light. Background <1 photon/sec. The color scale represents luminescence flux as 1-5 photons/pixel.

Differences in the kinetic properties of $Ca^{2+}$ responses can be detected subcellularly when GA is targeted to compartments, such as in the mitochondrial matrix (FIG. 6). A representative example is shown where NMDA application caused $Ca^{2+}$ responses in defined cellular locations with different temporal profiles. FIGS. 6A & B illustrates that, despite the low levels of light emission and moderate spatial resolution compared with conventional fluorescence, we can analyse the $Ca^{2+}$ response in specific areas. When reporters are subcellularly targeted, we can still detect a signal that is up to a 1000 fold higher than the background (15×15 pixel region, each pixel=0.65 μm). The graphical data derived from localized regions shown in the graphs demonstrates the diversity in the spatiotemporal properties of mitochondrial $Ca^{2+}$ changes.

Example 2

Optical detection of $Ca^{2+}$ induced bioluminescence in neurons using GFP-Aequorin targeted to the calcium sensor synaptic vesicle transmembrane protein, synaptotagmin 1. See FIGS. 1, 2 4D & 7. Synaptotagmin I is a low-affinity $Ca^{2+}$ sensor believed to be involved in the regulation of rapid exocytosis events (Davis et al, 1999). Previous studies show that Synaptotagmin I is; "tuned" to respond to $Ca^{2+}$ concentrations (21-74 μM that trigger synaptic vesicle membrane fusion (threshold >20 μM half-maximal rates at 194 μM. We have constructed a low-affinity version of GFP-Aequorin targeted to synaptic vesicles by fusion to Synaptotagmin I, known as SynGAmut. By using the low-affinity version of the $Ca^{2+}$ reporter, which only detects high calcium concentration domains, it should be possible to optically probe neuronal exocytosis in a specific manner. For example, SynGAmut could allow specific detection of vesicles located in close proximity to voltage-gated $Ca^{2+}$ channels, which are docked for neurotransmitter release (FIG. 4D). These vesicles would be located close enough to the mouth of a channel and therefore within a high $Ca^{2+}$ concentration domain, which is believed to be necessary to drive vesicle exocytosis that facilitates synaptic transmission. Given that the reporter has a lower affinity for $Ca^{2+}$, vesicles that are not docked for release would be sufficiently far enough away not to be detected.

Example 3

Figure 3:
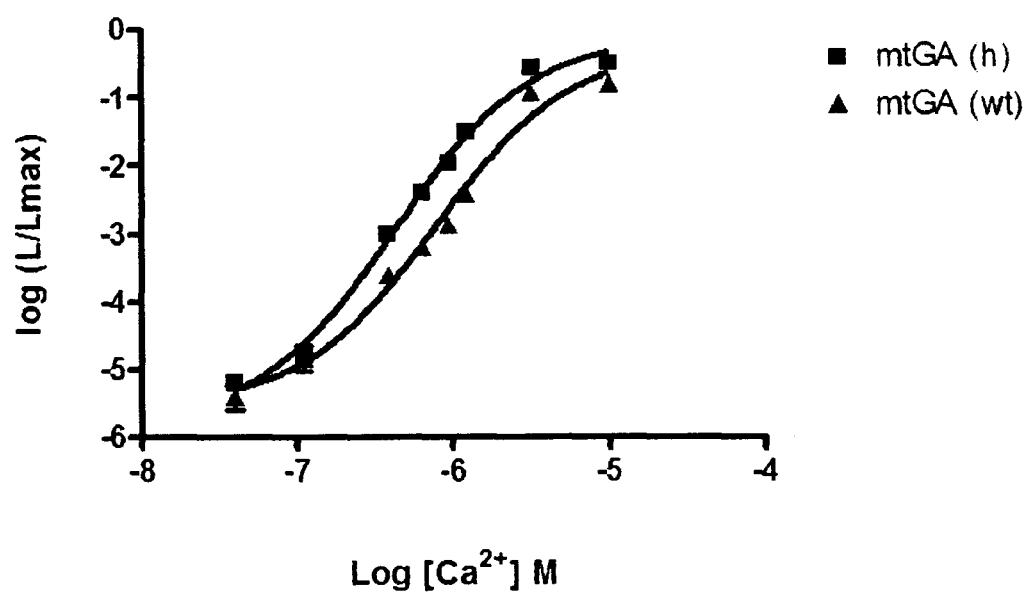
FIG. 3: $Ca^{2+}$ concentration response curves for mtGA. $Ca^{2+}$ concentration response curves for mtGA after reconstitution of the recombinant protein with the native or the synthetic analog, h coelenterazine, which is reported to be more sensitive to $Ca^{2+}$ than is the native complex. (determined at pH 7.2 and 26° C. (n=3)). The fractional rate of aequorin consumption is proportional in the physiological pCa range, to $[Ca^{2+}]$. The fractional rate of photoprotein consumption is expressed as the ratio between the emission of light at a defined $[Ca^{2+}]$ (L) and the maximal light emission at a saturating $[Ca^{2+}]$ (Lmax).
Figure 7:
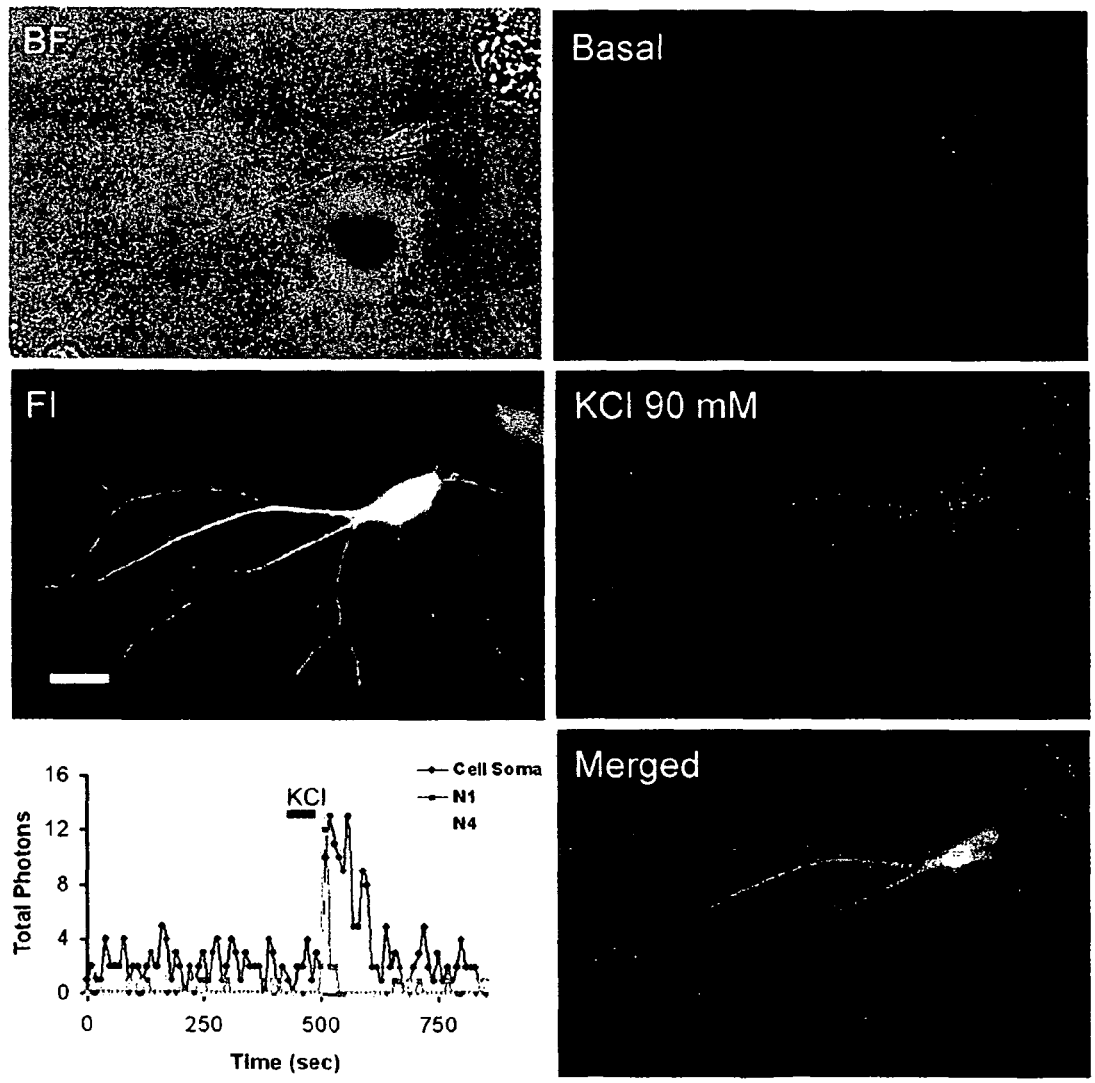
FIG. 7: Ca2+ induced bioluminescence activity in a cortical neuron transfected with SynGA. In basal conditions, before the addition of a neuromodulator, regions analysed showed a higher level of activity in comparison to background. This is consistently observed in neurons transfected with SynGA. Normally, it is difficult to detect resting levels of Ca2+ when GFP-Aequorin is regenerated with native aequorin, given the low binding affinity of the reporter. mtGA and PSDGA, do not generally exhibit the same kind of activity, although PSDGA sometimes shows very localized Ca2+ fluxes that occur spontaneously and in a stochastic fashion. These results suggest that SynGA is targeted to a cellular domain that is higher in Ca2+ than normally reported for resting levels of cytosolic Ca2+. Background photons were less than 1 photon/sec in the 256×256 pixel region. 20×20 pixel regions were selected from the cell soma and various places along the neurites. Graphical data also shows the increase in background counts for each region. Note, that background is very close to zero, so it is not seen. Influx of Ca2+ in the cell soma and neurites after addition of high K+(90 mM KCl). Corresponding (BF) brightfield and (FI) fluorescence images are shown as well as the superimposition of the photon image with the fluorescence image. Scale bar=20 μm. Photon images were scaled for 1-5 photons/pixel.
Figure 8:
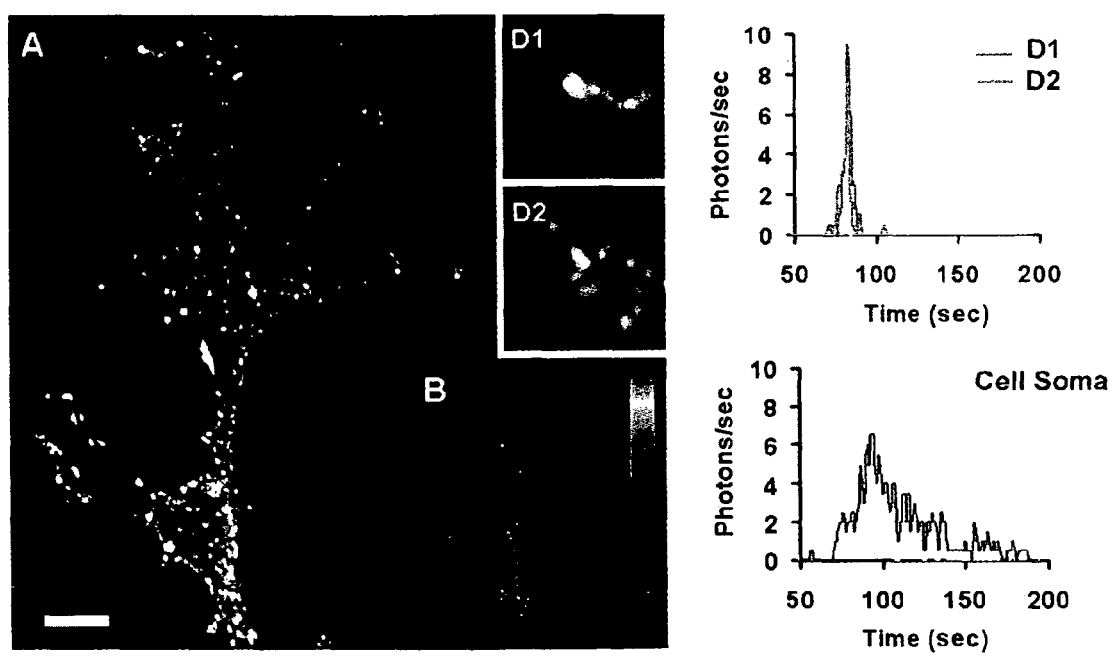
FIG. 8. Cortical neurons transfected with PSDGA. (A) GFP fluorescence was visualized to identify those neurons showing expression of the Ca2+ reporter, which resembles that of the native PSD95 protein. Photon emission in two dendritic regions (15×15 pixels), denoted D1 and D2 and in the same size region from the cell soma, were investigated and are graphically represented. The dynamics of Ca2+ signaling was found to be identical in the two dendritic regions analysed, but markedly different in comparison to the cell soma. (B) Photon image showing the total integration (50-200 s) of photons emitted after the first application of NMDA. Photons were only detected in the cell soma region after a second application of NMDA as the total photoprotein in the two dendritic regions analysed was completely consumed after the first application of NMDA. The pseudo-color scale represents 1-5 photons/pixel. Scale bar=10 μm.

Ca2+ induced bioluminescence could also be visualized with subcellular resolution in cortical neurons expressing PSDGA and mtGA after NMDA application (FIGS. 7 & 8). In contrast to GA, application of NMDA to neurons transfected with PSDGA, produced $Ca^{2+}$ transients with faster kinetics and larger amplitudes (see FIG. 8 for a representative example of 3 experiments). Distinct differences in the $Ca^{2+}$ dynamics in the dendrites (FIGS. 8D1 & D2) versus the cell soma were observed (FIG. 8, cell soma). In particular, the dendritic regions analysed exhibited a faster rate of rise with a rapid decay in the $Ca^{2+}$ response. The rapid rate of decay suggests that the photoprotein was completely consumed, rendering the temporal dynamics and amplitude of the $Ca^{2+}$ response to be artifactual. In addition, there was no further available photoprotein remaining, suggesting that the concentration of $Ca^{2+}$ in the domain where PSDGA was targeted to, would have been very high (refer to FIG. 3 for $Ca^{2+}$ binding curve).

Example 4

Figure 9:
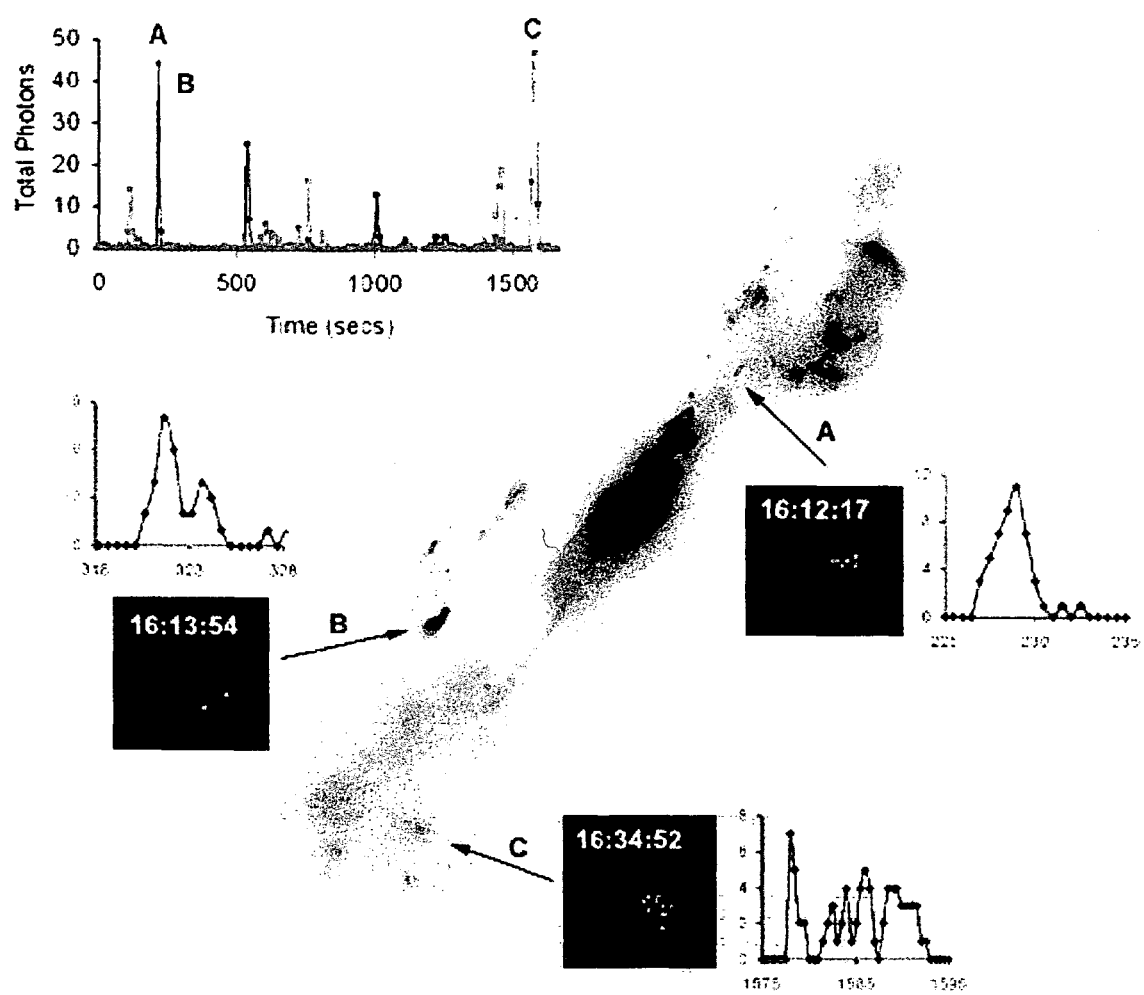
FIG. 9: Observation of spontaneous activity recorded from a cortical cell expressing PSDGA (GFP-Aequorin fused to PSD95). Responses were recorded under basal conditions and are graphically represented (colors represent data collected from the same 20×20 pixel region, each pixel=0.65 μm). Corresponding examples are demonstrated and include the integrated photon image and graphical data.

Transient transfection of cortical neurons with PSDGA directs localized expression of GA to dendritic structures (FIGS. 8 & 9). The localized targeting of GA when it is fused to PSD-95 enabled us to observe a specific type of activity in cortical neurons that were kept in basal conditions. In contrast to SynGA where the rate of light emission was constant, we observed random and non-synchronized $Ca^{2+}$-transients over a very low background that were spatially localized in some experiments. In at least two experiments (a representative example is shown in FIG. 9), the calcium transients occurred relatively frequently and were localized to dendritic regions (See FIGS. 9A, C & B).

Example 5

Progation of $Ca^{2+}$ intracellularly in a cortical neuron transfected with PSDGA (FIG. 13)
Result 4: Use of Genetically Targeted GFP-Aequorin for 'Real-Time' Visualisation of Calcium Dynamics in Neuronal Populations for Mapping Neural Connectivity.

We next examined the use of these reporters for following cell-cell communication in cultured neurons. We also electrically stimulated hippocampal neurons expressing the GA reporter to visualize the propagation of $Ca^{2+}$ activity and cellular communication within simple neural networks. In these experiments, we used a replication defective adenoviral vector coding for GA (Ad5-GA) to transfect dissociated hippocampal neurons. FIG. 14FI shows at least 2 cells expressing the GA reporter. Application of a short electrical pulse to the somatic region of the cell labelled I (FIG. 14BF), results in the propagation of a Ca2+ wave to the neighbouring cell labelled III. Analysis of Ca2+ responses in three regions, suggests that the propagation of $Ca^{2+}$ was variable between each region. From region I to II the wave was calculated to travel at a rate of 60 μm/s. In contrast, it was calculated to travel at a rate of 10 μm/s from region II to III. A total of 6 successive stimuli (one single pulse approx. every 2 mins) were applied (the first 5 of them are graphically represented), after which spontaneous occurring oscillations appeared (FIG. 14A-F). Each $Ca^{2+}$ "spike" displayed a rapid rate of rise followed by a slow decline. Significant photoprotein activity was also still remaining (determined by mechanical rupture of the cell membrane) after recording these $Ca^{2+}$ transients for approximately 45 minutes.
  from region II to III. A total of 6 successive stimuli (one single pulse approx. every 2 mins) were applied (the first 5 of them are graphically represented), after which spontaneous occuring oscillations appeared (FIG. 14A-F). Each $Ca^{2+}$ "spike" displayed a rapid rate of rise followed by a slow decline. Significant photoprotein activity was also still remaining (determined by mechanical rupture of the cell membrane) after recording these $Ca^{2+}$ transients for approximately 45 minutes.
Spontaneous activities recorded in organotypic slices infected with a replication defective adenoviral vector coding for GA (Ad5-GA) (FIG. 10). Long-term recordings (for up to 8 hours) can be undertaken when GA is expressed in tissue slices, such as organotypic slices from the cortex. In general, we find that photoprotein consumption and the level of sensitivity for detecting variations in $Ca^{2+}$ is relevant to the amount of reporter expressed, to the localization of the reporter and to the type of coelenterazine analogues used (Shimomura, 1997; Shimomura et al, 1993). This can vary from application to application, from cell to cell and needs to be optimized in each case, much the same, as it needs to be for fluorescent probes.

Result 5: Construction of a Transgenic Animal Expressing GFP-Aequorin to a Specific Cell-Type, Subcellular Compartment or Cellular Microdomain to Study Calcium Dynamics in Whole Animal Studies.

Transgenic animals have been constructed, which express targeted GFP-aequorin reporters. The GA transgene can be expressed in any cell type and/or at any stage of development. Expression has been made conditional by using a Lox-stop-Lox sequence immediately after the strong promoter, β-Actin (CAG). Selection of the expressing cells is made by using an appropriate endonuclease Cre, driven by specific promoters. To have the possibility to express in any cell, the transcription unit has been introduced by homologous recombination in ES cells in the reconstituted HPRT locus to minimize the influence of the integration site on the level of expression. Recombinant viruses containing CRE that are under the regulation of a cell specific promoter can also be used. In the example shown here for a transgenic mouse constructed with GFP-aequorin targeted to the mitochondrial matrix, activation of transgene expression has been induced in all cells and from the beginning of development by crossing these mice with a PGK-CRE mouse. Fluorescence imaging of whole embryos and neonatal mice reveals that the mtGA transgene is expressed in all cell types (FIGS. 15, 17, 18 and 19). The reporter protein is also well targeted to the mitochondrial matrix (FIGS. 16C2 & 18). Some advantage of GFP-aequorin is that it is not an endogenous protein normally expressed by mammalian cells and it has little interference with $Ca^{2+}$ signaling because of its low binding affinity. Accordingly, we do not find evidence of a abnormal phenotype in transgenic lines obtained with GFP-aequorin reporters.

Figure 17:
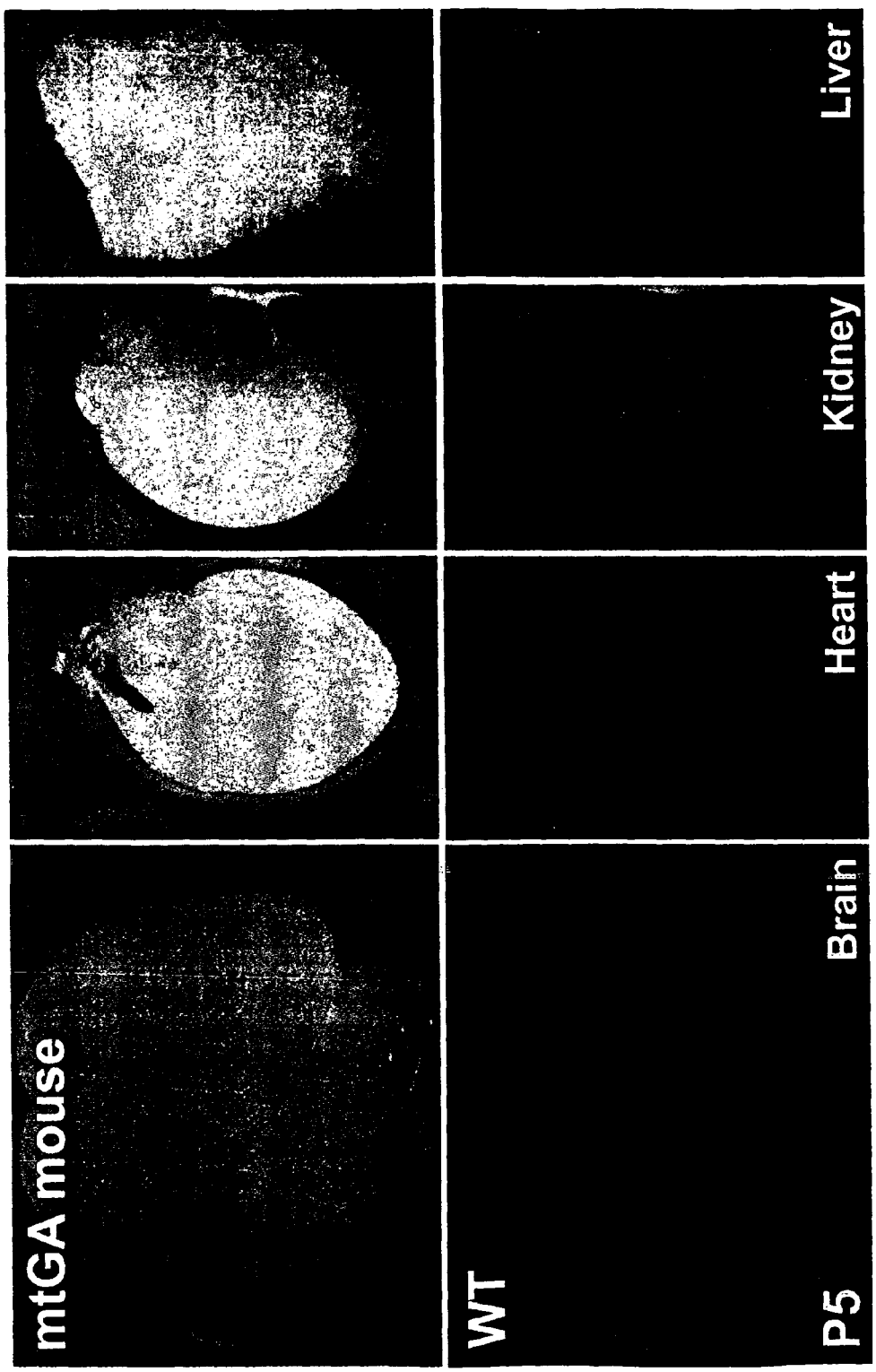
FIG. 17. GFP fluorescence images of organs excised from transgenic neonatal mice versus organs from wildtype mice. GFP fluorescence images of P5 transgenic mtGA vs wildtype mouse. Images were taken of the major organs and show strong levels of expression in all organs. Highest levels of expression are apparent in the heart and liver. No abnormalities in the organs are apparent when the transgene is activated at the beginning of development in all cells.

Confocal analysis shows expected expression patterns of the GA reporters after fusion to the signal peptide of cytochrome c for targeting to the mitochondrial matrix (mtGA) (FIG. 16C2). GFP fluorescence images of major organs indicate strong levels of reporter expression in the major organs (FIG. 17). Higher levels of expression are apparent in the heart and liver. In the brain, expression of the transgene is evident in both glial cells and neurons after comparison to antibodies against GFAP and NeuN, respectively (FIG. 19). These results show that the mtGA transgene is well targeted and expressed in all cells of the brain when transgenic mtGA reporter mice are crossed with PGK-CRE mice.

Figure 20:
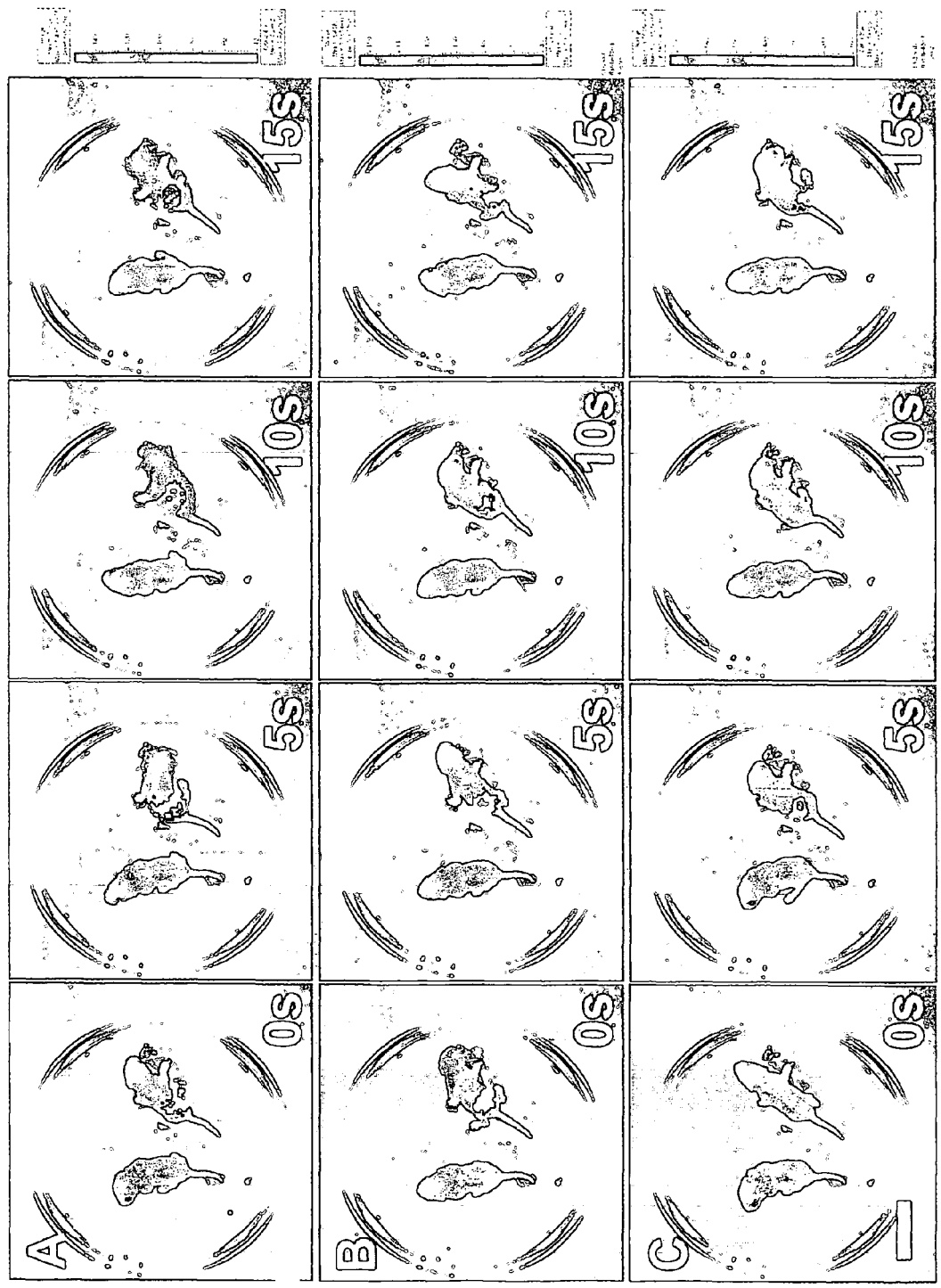
FIG. 20. Whole animal bioluminescence imaging of P1 mice with mitochondrially targeted GFP-aequorin. The mouse on the left handside is a wild-type mouse and the mouse on the right handside is a transgenic mouse expressing mitochondrially targeted GFP-aequorin in all cells. Both mice have been injected intraperitoneally with coelenterazine (4 µg/g). A-C, represent separate sequences where consecutive images were acquired over time. A grayscale photograph of the mice was first collected in the chamber under dim light emitting diode illumination, followed by the acquisition and overlay of the pseudocolor luminescent image. Each frame represents 5 seconds of light accumulation. Color bars corresponding to the light intensity from violet (least intense) to red (most intense) is given at the end of each sequence. Scale bar=2 cm.

Analysis of luminescence activities indicates that the GFP-aequorin protein is functional in respect to detection of $Ca^{2+}$. We have obtained preliminary data using our transgenic mice, showing that we can detect mitochondrial $Ca^{2+}$ oscillations in organotypic slices from the neocortex (FIG. 20). The $Ca^{2+}$ transients occurred synchronously across a large-scale area at a rate of once every 15-45 secs. As we are using bioluminescence to detect $Ca^{2+}$ activities, slice imaging can be undertaken for periods of up to 8 hours in real-time. Our results show that the GFP-aequorin reporter provides an excellent signal-to-noise ratio for detecting the $Ca^{2+}$ transients in brain slices from transgenic animals.

Figure 21:
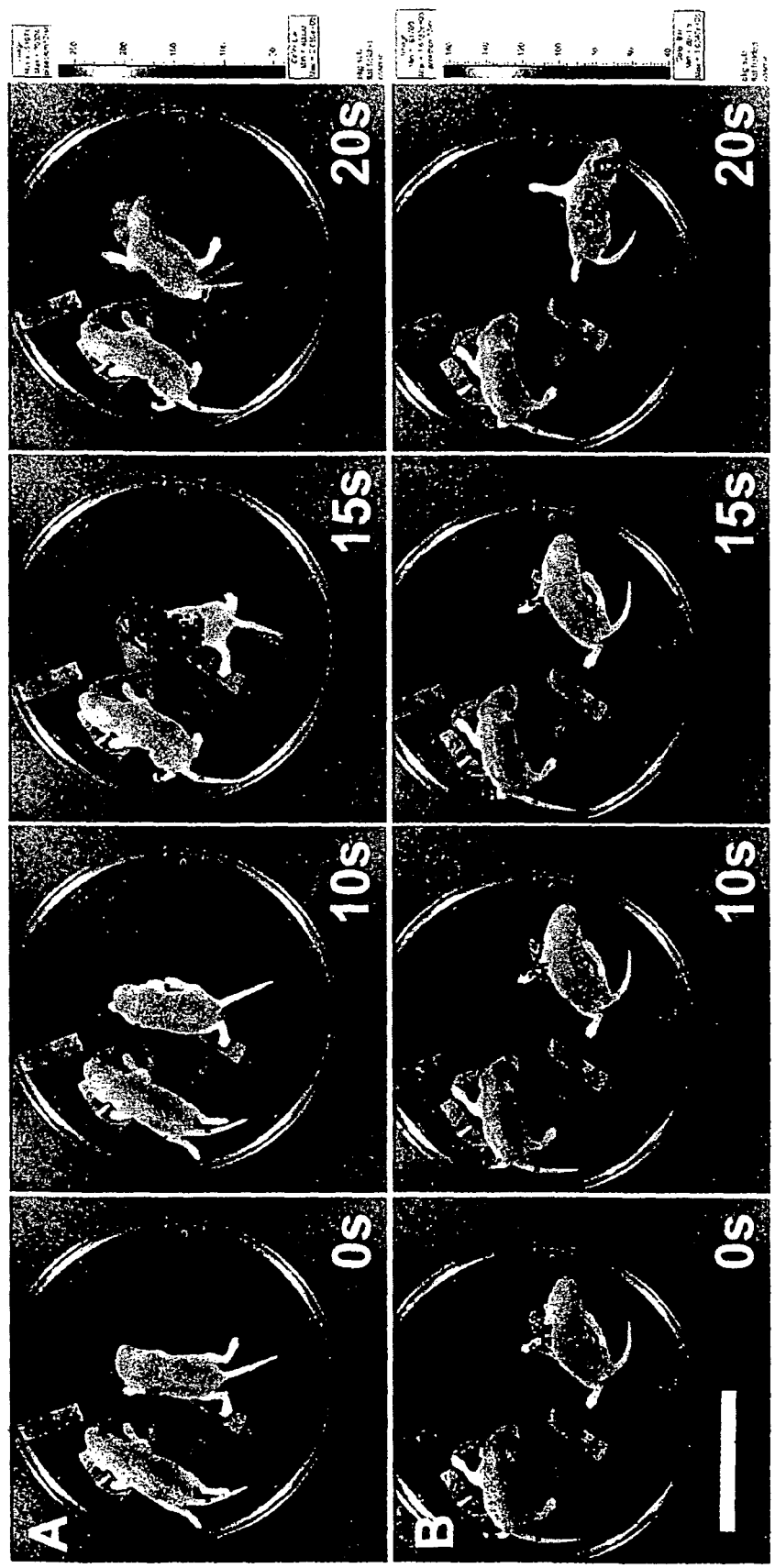
FIG. 21. Whole animal bioluminescence imaging of a P3 mouse with mitochondrially targeted GFP-aequorin. The mouse on the left handside is a wild-type mouse and the mouse on the right handside is a transgenic mouse expressing mitochondrially targeted GFP-aequorin in all cells. Both mice have been injected intraperitoneally with coelenterazine (4 µg/g). A & B represent separate sequences where consecutive images were acquired over time. A grayscale photograph of the mice was first collected in the chamber under dim light emitting diode illumination, followed by the acquisition and overlay of the pseudocolor luminescent image. Each frame represents 5 seconds of light accumulation. Color bars corresponding to the light intensity from violet (least intense) to red (most intense) is given at the end of each sequence. Scale bar=4 cm.
Figure 22:
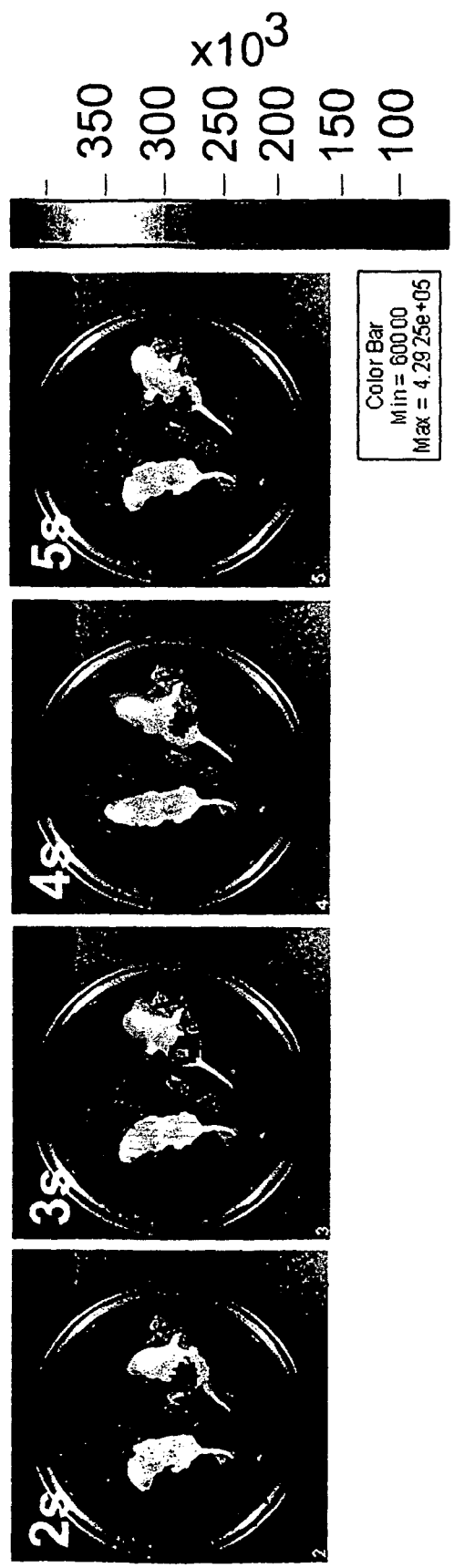
FIG. 22. Whole animal bioluminescence imaging of mitochondrial Ca2+ dynamics with higher time resolution. The mouse on the left handside is a wild-type mouse and the mouse on the right handside is a transgenic mouse expressing mitochondrially targeted GFP-aequorin in all cells. Both mice have been injected intraperitoneally with coelenterazine (4 μg/g). Exposure times are indicated on each consecutive frame, ranging from 2-5 seconds.
Figure 23:
FIG. 23. Whole animal bioluminescence imaging of mitochondrial Ca2+ with higher time resolution. The mouse on the left handside is a wild-type mouse and the mouse on the right handside is a transgenic mouse expressing mitochondrially targeted GFP-aequorin in all cells. Image represents 1 second of light accumulation. Color bar corresponds to the intensity of light. The image was acquired using the Xenogen IVIS 100 whole animal bioluminescence system. Binning=16, F/stop=1.

Bioluminescence was also detected in transgenic mice expressing mitochondrially targeted GFP-aequorin. To image $Ca^{2+}$-induced bioluminescence from within a transgenic mouse expressing GFP-aequorin reporters, coelenterazine needs to be injected (e.g. intra-peritoneally or by the tail vail). We tested whether local $Ca^{2+}$ dynamics can be detected in live mice, after injecting neonates intra-peritoneally with coelenterazine and then imaging them at different time resolutions. Transgenic mice were directly compared to non-transgenic mice, by imaging a series of consecutive images consisting of 5-second acquisition frames. Grayscale photographs of the mice were first collected to follow mouse movements and to correlate these images with the overlay of bioluminescence images. We found that sequence files showed dynamic emission of bioluminescence correlating to mouse movements (FIGS. 20 and 21). The bioluminescence detected was characteristic of light having short flash kinetics as it appeared in single frames and corresponding to mouse movements. At higher time resolutions, 2-4 second frames (FIG. 22), $Ca^{2+}$ signals could also be detected inside of the mitochondrial matrix of freely moving mice. We could also detect signals with a good signal-to-noise ratio using a 1-second acquisition time (FIG. 23). Short flashes of bioluminescence were detected in areas such as the hind legs, forelimbs, spinal cord, cerebral trunk and other dorsal areas of the body. In all cases, these $Ca^{2+}$ signals were synchronized with regions of the body where skeletal muscle contraction-relaxation was occurring according to what is seen in the greyscale photographs taken prior to each luminescent image. It has only been shown very recently using two-photon microscopy in vivo analysis of fluorescent $Ca^{2+}$ reporters, that skeletal muscle mitochondria take up and release $Ca^{2+}$ during muscle contraction-relaxation. However, this approach was more invasive, because it utilized excitation light and electroporation techniques as a means to deliver DNA into the muscle fibers and because it was necessary to detach the distal tendon and surgically expose the muscle fibers of interest for the in vivo imaging using two-photon microscopy. Furthermore, it was necessary to maintain mice under anaesthetics during the procedure and there is some evidence suggesting that volatile anaesthetics can directly affect complex proteins within the mitochondrial respiratory chain. Nevertheless, these studies produced images of mitochondrial $Ca^{2+}$ uptake and release during contraction-relaxation of the muscle fibers with very high spatial resolution.

Potential Application 1: Detection of Calcium Fluctuations Associated with Morphological or Developmental Changes in Neurons Using Genetically Targeted GFP-Aequorin.

$Ca^{2+}$ is believed to be a central modulator of growth cone motility in neurons. Using photolabile caged $Ca^{2+}$, studies have shown that transient elevations in $Ca^{2+}$ positively modulates growth cone motility. GAP43 is believed to be an important protein involved in axon guidance during development and in regeneration following nerve injury. The axonal/growth cone protein, GAP43 is believed to be associated with calmodulin at the membrane and is activated by the transient $Ca^{2+}$ increase believed to be associated with growth cone motility. Hence, GFP-Aequorin targeted to the post-synaptic density protein, GAP43, would enable localised calcium signalling and corresponding morphological changes associated with neurite outgrowth to be monitored during development and in neural regeneration.

Potential Application 2: Use of Targeted GFP-Aequorin to Monitor Receptor Function, Those Permeable to $Ca^{2+}$ or Those Associated with a Localised Increase in Calcium Concentration.

Example 1

Using GFP-Aequorin fused to PSD95 for specifically monitoring localised $Ca^{2+}$ increases after NMDA receptor activation and abnormalities associated with calcium signaling in neurological diseases, such as Alzheimer's diseases.

Example 2

Using targeted and low affinity GFP-Aequorin for selective detection of high calcium concentration microdomains in cell population studies for high-throughput screening (i.e. In multi-well format, 96, 386 or 1544 well plates) of pharmacological agents or chemical compound, or combinatorial compound libraries for detection of pharmacological candidates that could treat neurological diseases. This technique is considerably more powerful than those utilising fluorescent dyes that sense calcium.

Potential Application 3: Preclinical Trial Studies:

Dynamic images of $Ca^{2+}$ activity can be acquired by in vivo whole animal bioluminescence imaging of living subjects (FIGS. 15-18). The light produced penetrates mammalian tissues and can be externally detected and quantified using sensitive light-imaging systems. GFP-aequorin signals emerging from within living animals produce high signal-to-noise images of $Ca^{2+}$ fluxes that can be followed with high temporal resolution. This technique represents a powerful tool for performing non-invasive functional assays in living subjects and should provide more predictive animal data for preclinical trial studies.

Discussion

This invention thus provides a modified bioluminescent system comprising a fluorescent molecule covalently linked with a photoprotein, wherein the link between the two proteins has the function to stabilize the modified bioluminescent system and allow the transfer of the energy by Chemiluminescence Resonance Energy Transfer (CRET). In a preferred embodiment, the bioluminescent system comprises a GFP protein covalently linked to a aequorin protein, wherein the link between the two proteins has the function to stabilize the modified bioluminescent system and to allow the transfer of the energy by Chemiluminescence Resonance Energy Transfer (CRET).

This invention provides a composition comprising a recombinant polypeptide, wherein the composition has the functional characteristics of binding calcium ions and permitting measurable energy, said energy depending of the quantity of calcium bound and of the quantity of polypeptides in said composition in absence of any light excitation.

This invention incorporates a peptide linker having the function after translation to approach a donor site to an acceptor site in optimal conditions to permit a direct transfer of energy by chemiluminescence in a polypeptide according to the invention. Preferred linkers are described in PCT Application WO01/92300, published 6 Dec. 2001, U.S. application Ser. Nos. 09/863,901 and 10/307,389 the entire disclosures of which are relied upon and incorporated by reference herein.

Thus, this invention utilizes a recombinant polypeptide of the formula:

GFP-LINKER-AEQ;

wherein GFP is green fluorescent protein; AEQ is aequorin; and LINKER is a polypeptide of 4-63 amino acids, preferably 14-50 amino acids.

The LINKER can comprise the following amino acids:

(Gly Gly Ser Gly Ser Gly Gly Gln Ser)$_n$, (SEQ ID NO: 1) wherein n is 1-5. Preferably, n is 1 or n is 5. LINKER can also include the amino acid sequence Ser Gly Leu Arg Ser (SEQ ID NO: 7).

Another recombinant polypeptide for energy transfer from aequorin to green fluorescent protein by Chemiluminescence Resonance Energy Transfer (CRET) following activation of the aequorin in the presence of Ca$^{++}$ has the formula:

GFP-LINKER-AEQ;

wherein GFP is green fluorescent protein; AEQ is aequorin; and LINKER comprises the following amino acids:
(Gly Gly Ser Gly Ser Gly Gly Gln Ser)$_n$, (SEQ ID NO: 1) wherein n is 1-5; and wherein the fusion protein has an affinity for Ca$^{2+}$ ions and a half-life of at least 24 hours. The LINKER can include the amino acid sequence Ser Gly Leu Arg Ser (SEQ ID NO: 7). In addition, the recombinant polypeptide can further comprise a peptide signal sequence for targeting the recombinant polypeptide to a cell or to a subcellular compartment.

This invention also provides polynucleotides encoding recombinant polypeptides as described above.

Plasmids containing polynucleotides of the invention have been deposited at the Collection Nationale de Cultures de Microorganismes ("C.N.C.M."), Institut Pasteur, 28, rue du Docteur Roux, 75724 Paris Cedex 15, France, as follows:

| Plasmid | Accession No. | Deposit Date |
|---|---|---|
| PSDGA | I-3159 | Feb. 12, 2004 |

E. coli cells comprising the PSDGA plasmid can be cultivated in LB medium at 37° C., in conventional cell culture conditions.

Ca$^{2+}$ transients participate in a diverse array of signaling pathways, which are necessary for development, neuronal plasticity, neurotransmission, excitotoxicity and other important processes. Encoding Ca$^{2+}$-dependent activity at the cellular and subcellular level is complex, involving spatial, temporal and quantitative factors. Here we demonstrate an approach to quantitate local Ca$^{2+}$ signaling by visualizing bioluminescence of the genetically encoded recombinant polypeptide, GFP-aequorin. By fusion to a signal peptide or to proteins important in synaptic transmission, a set of Ca$^{2+}$ sensitive recombinant polypeptide that can be used to directly visualize local Ca$^{2+}$ signaling in single cells or in more complex systems have been constructed. By detection of bioluminescence, it is possible to measure local Ca$^{2+}$ signals having different spatial-temporal properties, with a good signal-to-noise ratio.

Toxicity and Degradation of the Recombinant GFP-Aequorin Polypeptide.

This invention shows that this bifunctional recombinant polypeptide can enable the investigation of calcium activities in neuronal networks, in specific subcellular compartments and in cellular microdomains, of dissociated cell cultures, acute or organotypic slices and transgenic animals.

The expression of this recombinant polypeptide of the invention in different biological systems has shown that there is no toxicity in vitro or in vivo, at the one-cell, the tissue or even the whole transgenic animal or plant stage. This result is also achieved when said recombinant polypeptide is strongly expressed. Therefore, no toxicity has been reported when the recombinant polypeptide is expressed from early stages of development right trough to the adult, in transgenic mice. Moreover, despite the fact that the recombinant polypeptide is neither an endogenous protein nor does it contains endogenous components, the expression does not perturb normal physiological function. No behavioural defects have been reported. The low Ca$^{2+}$ binding affinity of GFP-aequorin (see FIG. 2C), does not cause significant perturbation to Ca$^{2+}$ signals.

Another feature of this recombinant polypeptide is that despite its exogenous origin, there is no degradation of said recombinant protein according to the cell type where it is expressed in or the developmental stage.

The characteristics of these bifunctional recombinant polypeptides make them a useful tool to study localised Ca$^{2+}$ signaling in disease processes. In particular, a targeted bifunctional recombinant polypeptide could be used to monitor the function of a receptor when associated to a localised increase in the concentration of Ca$^{2+}$, such as studies of NMDA receptor function in neurodegenerative disease models, using the PSDGAmut protein, which targets to the postsynaptic density, including to NMDA receptors.

The characteristics of these bifunctional recombinant polypeptides make them an extremely useful tool for the visualisation of dynamic or fluctuating changes in Ca$^{2+}$ at central synapses that may occur over prolonged periods, such as between neuronal connections during development or with altered network properties that accompany learning and memory, aging and changes associated with chronic exposure to drugs.

The characteristics of these bifunctional recombinant polypeptides make them an extremely useful tool in diagnostics or in the drug discovery process. In particular, a targeted bifunctional recombinant polypeptide could be used to monitor specifically the function of a receptor that is associated with a known localised increase in the concentration of Ca$^{2+}$. GFP-Aequorin could be targeted to a specific cellular site associated with a high Ca$^{2+}$ concentration microdomain and used to monitor drug effects in a more specific fashion in cell populations using high-throughput screening. Current methods utilise non-targeted fluorescent indicators for this purpose and are subject to problems associated with photobleaching, phototoxicity, low signal-noise ratio, dye leakage, heterogenous dye distribution, detection of other calcium dynamics indirectly associated with receptor activation, eg. Calcium induced calcium release. A recent study of high-throughput drug candidate screening, demonstrated that the non-targeted version of GFP-Aequorin has a significantly better signal-to-noise ratio than that offered by fluorescent probes. This is particularly advantageous for monitoring small Ca$^{2+}$ fluxes such as those induced by activation of inhibitory G-proteins, which are implicated in a number of neurological diseases (Niedernberg et al. 2003). GFP-Aequorin could therefore also be useful for monitoring Ca$^{2+}$ fluxes associated with the nicotinic receptor subtype, known as the alpha-7 containing nicotinic receptor, which are difficult to detect with flourescent indicators.

Optical detection of Ca$^{2+}$ can offer a simple approach for visualizing 'real-time' dynamic activity and long-term cellular changes that are associated with specific phenotypes or pathologies. For example, characterizing the spatiotemporal specificity of Ca$^{2+}$ profiles in synaptic function is important to understand the mechanisms contributing to perturbed neuronal Ca$^{2+}$ homeostasis, which has been implicated in schizophrenia and early events associated with the onset of neurodegenerative diseases such as Alzheimer's, Parkinson's and Huntington's diseases (Lidow, 2003; Mattson and Chan, 2003; Stutzmann et al., 2004; Tang et al., 2003).

An advantage of working with bioluminescence is that recordings with very high time resolution can be undertaken over extended periods. For long-term recordings, the consumption of the aequorin photoprotein needs to be taken into consideration. However we have been able to undertake long-term recordings (for up to 9 hours) with very high time resolution (1 ms resolution) on tissue slices, including cortical slices. Overall, we find that photoprotein consumption and the level of sensitivity for detecting variations in $Ca^{2+}$ is relevant to the amount of recombinant polypeptide expressed, to the localization of the expressed recombinant polypeptide and to the type of coelenterazine analogues used (Shimomura, 1997; Shimomura et al, 1993). This can vary from application to application, from cell to cell and needs to be optimized in each case, much the same as it needs to be for fluorescent probes. $Ca^{2+}$ sensitive bioluminescent recombinant polypeptides could also represent the reporter of choice in studies on biological systems that are sensitive to light.

Comparison to $Ca^{2+}$ Sensitive Fluorescence Reporter Systems

Visualization of fluorescence requires an external light source for light excitation of the fluorescent molecule (light is generated through absorption of radiation), which causes photobleaching, phototoxicity and auto-fluorescence (high background with variable intensity over time). Bioluminescent reporters have significantly greater signal-to-noise ratio than fluorescent reporters. A high signal-to-noise ratio is desirable for better quality data in imaging applications, as low signal levels are less affected by interference.

Detection of bioluminescence is a non-invasive way to monitor biological processes in the living intact animal. Fluorescent reporters are a problem because light excitation on tissues results in a large degree of autofluorescence. Furthermore, light must pass through tissue to excite fluorescent molecules and then light emitted of a longer wavelength must pass back through tissue to be seen by the detector. Genetically encoded Ca2+ sensitive fluorescent reporters are sensitive to temperature and pH or contain calmodulin, which is a native protein of mammalian cells. Over-expression of calmodulin could produce a phenotype in transgenic animals.

Comparison of the Aequorin-Coelenterazine System to the Luciferase-Luciferin System for Whole Animal In-Vivo Bioluminescence Imaging The luciferase reporter system has been utilized for following infection processes, tumour progression and gene expression in the living animal. This system is now well established as an animal model for testing drug candidates in clinical trials. Our recent data in single-cells and brain slices, suggests that using GFP-aequorin as a bioluminescent reporter at the single-cell level compares favourably to the luciferase system. As GFP-aequorin is a recombinant polypeptide that can be used as reporter of $Ca^{2+}$ activities, we utilize recombinant polypeptide expressing-mice for following more dynamic changes in the living mouse and show that it is possible to detect GA bioluminescence with good temporal resolution at the whole animal level. Elevation of $[Ca^{2+}]_i$ concentrations in specific cellular domains, are correlated with the onset of many pathological processes. Calcium is also an important signalling ion involved in development and apoptotic processes. We have found in our studies that large $Ca^{2+}$ changes are associated with apoptotic events. An early event in this process is believed to involve mitochondrial release of $Ca^{2+}$. Since $Ca^{2+}$ levels in the mitochondria of a healthy cell at rest are generally close to cytosolic $[Ca^{2+}]$, an increase in mitochondrial $Ca^{2+}$ levels are likely to mark very early changes that lead to cell death. Mitochondria are now regarded unequivocally as the cells biosensor and changes in mitochondrially $Ca^{2+}$ handling are central to this property. This will offer an alternative approach to the luciferase reporter and broaden the applications possible with this technology. Combined with the continual improvement in detector technology and with eventual improvements in the chemistry of the co-factor, these recombinant polypeptide expressing-mice have the potential to become a powerful system of analysis in all aspects of biology and for clinical testing of new treatment modalities.

Finally, we have constructed a transgene encoding mtGA that is under the control of the strong promoter, β-Actin and also the Lox-Stop-Lox system. Results shown here indicate that the CRE-regulated transgene is functional in the mouse embryo. By inducing cell-type specific expression of the reporter protein at any developmental stage in the mouse, we can now study more precisely cellular processes occurring inside the living animal. For example, we can utilise a recombinant virus containing CRE that is under the regulation of a cell specific promoter. Oncogenic processes or tumour progression could therefore be studied in a selected cell type or tissue in acute or organotypic slices or at the whole animal level.

A major advantage is that these animals could be crossed with mutant animals or models of disease to investigate different pathologies. These animals can also provide a specific source of labelled tissues, cells and tumours for ex-vivo or in-vitro studies Definitions The following terms have the following meanings when used herein:

Luminescence

Emission of an electromagnetic radiation from an atom or molecule in UV, in visible or IR. This emission results from the transition from an electronically excited state towards a state from weaker energy, generally the ground state.

Fluorescence

Fluorescence produced by a singlet, very short, excited electronically. This luminescence disappears at the same time as the source from excitation.

Chemiluminescence

Luminescence resulting from a chemical reaction.

Bioluminescence

Visible chemiluminescence, produced by living organisms. The invention mimics the system naturally present in the jellyfish, without fixation to a support.

Bioluminescent System

The bioluminescent system according to the invention is a chimeric tripartite molecule within the middle a peptide linker and a coenzyme (i.e., coelenterazine). The first molecule and the second molecule covalently attached with the linker can be everything if they have for the first a donor site and for the second an acceptor site attached on it (receptors-linker-ligand, antibody-linker antigen). The chimeric protein can be fused to a fragment of tetanus toxin for its retrograde and transynaptic transport on axon by Coen, L., Osta, R., Maury, M., and Brulet, P., Construction of hybrid proteins that migrate retrogradely and transynaptically into the central nervous system. Proc. Natl. Acad. Sci. (USA) 94 (1997) 9400-9405, or fused to a membrane receptor.

Non-Radiative

No emission of photon from aequorin to the GTP when aequorin is bounded by calcium ions (therefore there is no transmission of blue light by aequorin in the invention, the energy transfer is directly made between the two proteins).

FRET System

Transfer of energy by resonance by fluorescence (i.e., between two variants of GFP).

References

Fluorescent indicators for Ca2+ based on green fluorescent proteins and calmodulin.

Miyawaki, A., Llopis, J., Heim, R., McCaffery, J. M., Adams, J. A., Ikura, M. and Tsien, R. Y. Nature, (1997) Vol. 388 pp. 882-887.

Detection in living cells of Ca2+-dependent changes in the fluorescence emission of an indicator composed of two green fluorescent protein variants linked by a calmodulin-binding sequence. A new class of fluorescent indicators.

Romoser, V. A., Hinkle, P. M. and Persechini, A., J. Biol. Chem., (1997) Vol. 272, pp. 13270-13274.

Cret

Transfer of energy by resonance by chemiluminescence (i.e., fusion protein with GFP-aequorin (jellyfish Aequorea) but without linker or GFP-obeline).

References

Chemiluminescence energy transfer.

Campbell, A. K., in Chemiluminescence: Principles and application in Biology and Medicine, Eds Ellis Horwood, Chichester, UK 1988, pp. 475-534.

Bret

Transfer of energy by resonance by bioluminescence (i.e., interaction between GFP and luciferase jellyfish Renilla).

References

A bioluminescence resonance energy transfer (BRET) system: application to interacting circadian clock protein.

Xu, Y., Piston, D. W. and Johnson, C. H. Proc. Natl. Acad. Sci., (USA) (1999) Vol. 96, pp. 151-156.

BIBLIOGRAPHY

The following references are cited herein. The entire disclosure of each of these references and each of the other references cited herein is relied upon and incorporated herein.

U.S. Patent Documents:

U.S. Pat. No. 6,662,039 B2 Optical probing of neuronal connections with fluorescent indicators. December 2003 Yuste et al.

Publications:

Allen, D. G., Blinks, J. R., and Prendergast, F. G. (1977). Aequorin luminescence: relation of light emission to calcium concentration—a calcium-independent component. Science 195, 996-998.

Augustine, G. J., Santamaria, F., and Tanaka, K. (2003). Local calcium signaling in neurons. Neuron 40, 331-346.

Baron, K. T., Wang, G. J., Padua, R. A., Campbell, C., and Thayer, S. A. (2003). NMDA-evoked consumption and recovery of mitochondrially targeted aequorin suggests increased Ca2+ uptake by a subset of mitochondria in hippocampal neurons. Brain Res 993, 124-132.

Baubet, V., Le Mouellic, H., Campbell, A. K., Lucas-Meunier, E., Fossier, P., and Brulet, P. (2000). Chimeric green fluorescent protein-aequorin as bioluminescent Ca2+ reporters at the single-cell level. Proc Natl Acad Sci USA 97, 7260-7265.

Bauer, P. J. (2001). The local Ca concentration profile in the vicinity of a Ca channel. Cell Biochem Biophys 35, 49-61.

Brini, M., Marsault, R., Bastianutto, C., Alvarez, J., Pozzan, T., and Rizzuto, R. (1995). Transfected aequorin in the measurement of cytosolic Ca2+ concentration ([Ca2+]c). A critical evaluation. J Biol Chem 270, 9896-9903.

Brini, M., Pinton, P., Pozzan, T., and Rizzuto, R. (1999). Targeted recombinant aequorins: tools for monitoring [Ca2+] in the various compartments of a living cell. Microsc Res Tech 46, 380-389.

Christopherson, K. S., Sweeney, N. T., Craven, S. E., Kang, R., El-Husseini Ael, D., and Bredt, D. S. (2003). Lipid- and protein-mediated multimerization of PSD-95: implications for receptor clustering and assembly of synaptic protein networks. J Cell Sci 116, 3213-3219.

Conroy, W. G., Liu, Z., Nai, Q., Coggan, J. S., and Berg, D. K. (2003). PDZ-containing proteins provide a functional postsynaptic scaffold for nicotinic receptors in neurons. Neuron 38, 759-771.

DiGregorio, D. A., Peskoff, A., and Vergara, J. L. (1999). Measurement of action potential-induced presynaptic calcium domains at a cultured neuromuscular junction. J Neurosci 19, 7846-7859.

Emmanouilidou, E., Teschemacher, A. G., Pouli, A. E., Nicholls, L. I., Seward, E. P., and Rutter, G. A. (1999). Imaging Ca2+ concentration changes at the secretory vesicle surface with a recombinant targeted cameleon. Curr Biol 9, 915-918.

Etter E F, Minta A, Poenie M, Fay F S. (1996) Near-membrane [Ca2+] transients resolved using the Ca2+ indicator FFP18. Proc Natl Acad Sci USA. 93(11):5368-5373.

Eusebi, F., Miledi, R., Parker, I., Stinnakre, J. (1985) Postsynaptic calcium influx at the giant synapse of the squid during activation by glutamate. J. Physiol. 369, 183-197.

Fernandez-Chacon, R., Shin, O. H., Konigstorfer, A., Matos, M. F., Meyer, A. C., Garcia, J., Gerber, S. H., Rizo, J., Sudhof, T. C., and Rosenmund, C. (2002). Structure/function analysis of Ca2+ binding to the C2A domain of synaptotagmin 1. J Neurosci 22, 8438-8446.

Filippin, L., Magalhaes, P. J., Di Benedetto, G., Colella, M., and Pozzan, T. (2003). Stable interactions between mitochondria and endoplasmic reticulum allow rapid accumulation of calcium in a subpopulation of mitochondria. J Biol Chem 278, 39224-39234.

Goldberg, J. H., Tamas, G., Aronov, D., and Yuste, R. (2003). Calcium microdomains in aspiny dendrites. Neuron 40, 807-821.

Gorokhovatsky A Y., Marchenkov V V., Rudenko N V., Ivashina T V., Ksenzenko V N., Burkhardt N., Semisotnov G V., Vinokurov L M., Alakhov Y B. (2004) Fusion of Aequorea victoria GFP and aequorin provides their Ca(2+)-induced interaction that results in red shift of GFP absorption and efficient bioluminescence energy transfer. Biochem. Biophys. Res. Commun. 320(3):703-711. Hara M, Bindokas V, Lopez J P, Kaihara Hara M, Bindokas V, Lopez J P, Kaihara K, Landa L R Jr, Harbeck M, Roe M W. (2004). Imaging endoplasmic reticulum calcium with a fluorescent biosensor in transgenic mice. Am J Physiol Cell Physiol. 287(4):C932-8.

Hasan M T, Friedrich R W, Euler T, Larkum M E, Giese G, Both M, Duebel J, Waters J, Bujard H, Griesbeck 0, Tsien R Y, Nagai T, Miyawaki A, Denk W. 2004. Functional fluorescent Ca2+ indicator proteins in transgenic mice under TET control. PLoS Biol. 2(6):763-75.

Jaffe, L F (1993) Classes and mechanisms of calcium waves. Cell Calcium 14(10), 736-745.

Kandler K, Katz L C. (1998) Coordination of neuronal activity in developing visual cortex by gap junction-mediated biochemical communication. J. Neurosci. 18(4):1419-27.

Kendall J M, Sala-Newby G, Ghalaut V, Dormer R L, Campbell A K. (1992) Engineering the CA(2+)-activated photoprotein aequorin with reduced affinity for calcium. Biochem Biophys Res Commun.187(2):1091-1097.

Knopfel T, Tomita K, Shimazaki R, Sakai R. (2003) Optical recordings of membrane potential using genetically targeted voltage-sensitive fluorescent proteins. Methods. 30(1): 42-8.

Kovalchuk, Y., Eilers, J., Lisman, J., and Konnerth, A. (2000). NMDA receptor-mediated subthreshold Ca2+ signals in spines of hippocampal neurons. J Neurosci 20, 1791-1799.

Lidow, M. S. (2003). Calcium signaling dysfunction in schizophrenia: a unifying approach. Brain Res Brain Res Rev 43, 70-84.

Lipp P, Egger M, Niggli E. (2002). Spatial characteristics of sarcoplasmic reticulum Ca2+ release events triggered by L-type Ca2+ current and Na+ current in guinea-pig cardiac myocytes. J. Physiol. 15; 542(Pt 2):383-93.

Llinas, R., Sugimori, M., and Silver, R. B. (1995). The concept of calcium concentration microdomains in synaptic transmission. Neuropharmacology 34, 1443-1451.

Llinas, R., Sugimori, M., and Silver, R. B. (1992). Microdomains of high calcium concentration in a presynaptic terminal. Science 256, 677-679.

Marsault, R., Murgia, M., Pozzan, T., and Rizzuto, R. (1997). Domains of high Ca2+ beneath the plasma membrane of living A7r5 cells. Embo J 16, 1575-1581.

Mattson, M. P., and Chan, S. L. (2003). Neuronal and glial calcium signaling in Alzheimer's disease. Cell Calcium 34, 385-397.

Miller, A. L., Karplus, E., and Jaffe, L. F. (1994). Imaging [Ca2+]i with aequorin using a photon imaging detector. Methods Cell Biol 40, 305-338.

Miyawaki, A., Llopis, J., Heim, R., McCaffery, J. M., Adams, J. A., Ikura, M., and Tsien, R. Y. (1997). Fluorescent indicators for Ca2+ based on green fluorescent proteins and calmodulin. Nature 388, 882-887.

Montero, M., Alonso, M. T., Carnicero, E., Cuchillo-lbanez, I., Albillos, A., Garcia, A. G., Garcia-Sancho, J., and Alvarez, J. (2000). Chromaffin-cell stimulation triggers fast millimolar mitochondrial Ca2+ transients that modulate secretion. Nat Cell Biol 2, 57-61.

Montero, M., Alvarez, J., Scheenen, W. J., Rizzuto, R., Meldolesi, J., and Pozzan, T. (1997). Ca2+ homeostasis in the endoplasmic reticulum: coexistence of high and low [Ca2+] subcompartments in intact HeLa cells. J Cell Biol 139, 601-611.

Montero, M., Brini, M., Marsault, R., Alvarez, J., Sitia, R., Pozzan, T., and Rizzuto, R. (1995). Monitoring dynamic changes in free Ca2+ concentration in the endoplasmic reticulum of intact cells. Embo J 14, 5467-5475.

Morise, H., Shimomura, O., Johnson, F. H., Winant, J. (1974) Intermolecular Energy Transfer in the Bioluminescent system. Biochemistry, 13(12) 2656-2662.

Mothet J P, Fossier P, Meunier F M, Stinnakre J, Tauc L, Baux G. (1998) Cyclic A DP-ribose and calcium-induced calcium release regulate neurotransmitter release at a cholinergic synapse of Aplysia. J. Physiol. 507 (Pt 2):405-14.

Nagai T, Yamada S, Tominaga T, Ichikawa M, Miyawaki A. (2004) Expanded dynamic range of fluorescent indicators for Ca(2+) by circularly permuted yellow fluorescent proteins. Proc Natl Acad Sci USA. 101(29):10554-9.

Neher, E. (1998). Vesicle pools and Ca2+ microdomains: new tools for understanding their roles in neurotransmitter release. Neuron 20, 389-399.

Niedernberg A, Tunaru S, Blaukat A, Ardati A, Kostenis E. (2003) Sphingosine 1-phosphate and dioleoylphosphatidic acid are low affinity agonists for the orphan receptor GPR63. Cell Signal. 15(4): 435-46.

Nimchinsky, E. A., Yasuda, R., Oertner, T. G., and Svoboda, K. (2004). The number of glutamate receptors opened by synaptic stimulation in single hippocampal spines. J Neurosci 24, 2054-2064.

Peterlin Z A, Kozioski J, Mao B Q, Tsiola A, Yuste R. (2000) Optical probing of neuronal circuits with calcium indicators. Proc Natl Acad Sci USA. 97(7): 3619-24.

Pivovarova, N. B., Pozzo-Miller, L. D., Hongpaisan, J., and Andrews, S. B. (2002). Correlated calcium uptake and release by mitochondria and endoplasmic reticulum of CA3 hippocampal dendrites after afferent synaptic stimulation. J Neurosci 22, 10653-10661.

Rizzuto, R., Simpson, A. W., Brini, M., and Pozzan, T. (1992). Rapid changes of mitochondrial Ca2+ revealed by specifically targeted recombinant aequorin. Nature 358, 325-327.

Shimomura O, Musicki B, Kishi Y, Inouye S. (1993) Light-emitting properties of recombinant semi-synthetic aequorins and recombinant fluorescein-conjugated aequorin for measuring cellular calcium. Cell Calcium.14(5):373-8.

Shimomura O, Inouye S, Musicki B, Kishi Y. (1990) Recombinant aequorin and recombinant semi-synthetic aequorins. Cellular Ca2+ ion indicators. Biochem J. 270(2):309-12.

Shimomura O, Johnson F H. (1978) Peroxidized coelenterazine, the active group in the photoprotein aequorin. Proc Natl Acad Sci USA. 75(6): 2611-5.

Stosiek C, Garaschuk O, Holthoff K, Konnerth A. (2003) In vivo two-photon calcium imaging of neuronal networks. Proc Natl Acad Sci U S. 100(12): 7319-24.

Stutzmann, G. E., Caccamo, A., LaFerla, F. M., and Parker, I. (2004). Dysregulated IP3 signaling in cortical neurons of knock-in mice expressing an Alzheimer's-linked mutation in presenilin1 results in exaggerated Ca2+ signals and altered membrane excitability. J Neurosci 24, 508-513.

Tang, T. S., Tu, H., Chan, E. Y., Maximov, A., Wang, Z., Wellington, C. L., Hayden, M. R., and Bezprozvanny, I. (2003). Huntingtin and huntingtin-associated protein 1 influence neuronal calcium signaling mediated by inositol-(1,4,5) triphosphate receptor type 1. Neuron 39, 227-239.

Varadi, A., and Rutter, G. A. (2002). Dynamic imaging of endoplasmic reticulum Ca2+ concentration in insulin-secreting MIN6 Cells using recombinant targeted cameleons: roles of sarco(endo)plasmic reticulum Ca2+-ATPase (SERCA)-2 and ryanodine receptors. Diabetes 51, S190-201.

Wang, G. J., Jackson, J. G., and Thayer, S. A. (2003). Altered distribution of mitochondria impairs calcium homeostasis in rat hippocampal neurons in culture. J Neurochem 87, 85-94.

Wu J Y, Lam Y W, Falk C X, Cohen L B, Fang J, Loew L, Prechtl J C, Kleinfeld D, Tsau Y. (1998) Voltage-sensitive dyes for monitoring multineuronal activity in the intact central nervous system. Histochem J. 30(3): 169-87.

Yu D, Baird G S, Tsien R Y, Davis R L. (2003) Detection of calcium transients in *Drosophila* mushroom body neurons with camgaroo reporters. J. Neurosci. 23(1):64-72.

The invention claimed is:

1. A method for the optical detection of $Ca^{2+}$ signals in a transgenic mouse or rat, wherein the method comprises:
   (A) providing a moving, live, transgenic neonatal or embryonic mouse or rat whose genome comprises a transcriptionally active transgene encoding a $Ca^{2+}$-sensitive polypeptide, which comprises aequorin linked to a fluorescent protein, wherein the link between the aequorin and fluorescent protein functions to allow transfer of energy by Chemiluminescence Resonance Energy Transfer (CRET) between the two proteins;
   (B) administering coelenterazine or a coelenterazine analog to the mouse or rat;
   (C) non-invasively monitoring photons emitted by the $Ca^{2+}$-sensitive polypeptide; and wherein
   (D) the photons are monitored in the spinal cord, cerebral trunk, hind legs, forelimb, or skin of the transgenic mouse or rat.

2. A method as claimed in claim 1, wherein the fluorescent protein is chosen from GFP (green fluorescent protein), CFP (cyan fluorescent protein), YFP (yellow fluorescent protein), and RFP (red fluorescent protein).

3. A method as claimed in claim 1, wherein the $Ca^{2+}$-sensitive polypeptide comprises a mutation, wherein the mutation is a Asp→Ala substitution at position 119 of aequorin.

4. A method as claimed in claim 1, wherein the photons, which are emitted by the $Ca^{2+}$-sensitive polypeptide and which are monitored, are synchronized with skeletal muscle contraction and relaxation in the transgenic mouse or rat.

5. A method as claimed in claim 1, wherein the $Ca^{2+}$-sensitive polypeptide is targeted to mitochondria, and the method comprises monitoring mitochondrial calcium oscillations in the transgenic mouse or rat by the non-invasive monitoring of the photons emitted by the $Ca^{2+}$-sensitive polypeptide.

6. A method as claimed in claim 1, wherein the aequorin is encoded by a transgene in an HPRT locus of the transgenic mouse or rat.

7. A method according to claim 1, wherein the chemiluminescent protein is covalently linked to the fluorescent protein.

8. A method as claimed in claim 1, wherein the photons are monitored in the hind legs.

9. A method as claimed in claim 1, wherein the photons are monitored in the forelimbs.

10. A method as claimed in claim 1, wherein the photons are monitored in the skin.

11. A method for the optical detection of $Ca^{2+}$ signals in transgenic neonatal or embryonic mice or rats, wherein the method comprises:
(A) providing a moving, live, transgenic, neonatal or embryonic mouse or rat whose genome comprises a transcriptionally active transgene encoding a $Ca^{2+}$-sensitive polypeptide comprising aequorin linked to a fluorescent protein, wherein the link between the aequorin and fluorescent protein functions to allow transfer of energy by Chemiluminescence Resonance Energy Transfer (CRET) between the two proteins;
(B) administering coelenterazine or a coelenterazine analog to the mouse or rat; and
(C) non-invasively monitoring photons emitted by the $Ca^{2+}$-sensitive polypeptide.

12. A method as claimed in claim 1, wherein the photons are monitored in the cerebral trunk.

13. A method as claimed in claim 1, wherein the photons are monitored in the spinal cord.

14. A method as claimed in claim 1, wherein the $Ca^{2+}$-sensitive polypeptide comprises a signal peptide capable of targeting the polypeptide to a specific cellular domain or compartment.

15. A method as claimed in claim 14, wherein the specific cellular domain or compartment is selected from the nucleus, cytoplasm, mitochondria, endoplasmic reticulum, or plasma membrane.

16. A method as claimed in claim 11, wherein the $Ca^{2+}$-sensitive polypeptide comprises a signal peptide capable of targeting the polypeptide to a specific cellular domain or compartment.

17. A method as claimed in claim 16, wherein the specific cellular domain or compartment is selected from the nucleus, cytoplasm, mitochondria, endoplasmic reticulum, or plasma membrane.

* * * * *

SEQUENCE LISTING

<160> NUMBER OF SEQ ID NOS: 7

<210> SEQ ID NO 1
<211> LENGTH: 45
<212> TYPE: PRT

```
<213> ORGANISM: Artificial Sequence
<220> FEATURE:
<223> OTHER INFORMATION: Description of Artificial Sequence: Synthetic
      linker peptide
<220> FEATURE:
<223> OTHER INFORMATION: Sequence may encompass 1 to 5
      [Gly-Gly-Ser-Gly-Ser-Gly-Gly-Gln-Ser] repeats; see specification
      for further embodiments

<400> SEQUENCE: 1

Gly Gly Ser Gly Ser Gly Gly Gln Ser Gly Gly Ser Gly Ser Gly Gly
 1               5                  10                  15

Gln Ser Gly Gly Ser Gly Ser Gly Gly Gln Ser Gly Gly Ser Gly Ser
             20                  25                  30

Gly Gly Gln Ser Gly Gly Ser Gly Ser Gly Gly Gln Ser
         35                  40                  45

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: Synthetic
      flexible linker sequence

<400> SEQUENCE: 2
aattcggtcc ggcgggagcg gatccggcgg ccagtccccg c                    41

<210> SEQ ID NO 3
<211> LENGTH: 3660
<212> TYPE: DNA
<213> ORGANISM: Artificial Sequence
<220> FEATURE:
<223> OTHER INFORMATION: Description of Artificial Sequence: Synthetic
      coding sequence contained in PSDGA vector
<220> FEATURE:
<221> NAME/KEY: CDS
<222> LOCATION: (1)..(3657)

<400> SEQUENCE: 3 atg gac tgt ctc tgt ata gtg aca acc aag aaa tac cgc tac caa gat    48
Met Asp Cys Leu Cys Ile Val Thr Thr Lys Lys Tyr Arg Tyr Gln Asp
 1               5                  10                  15 gaa gac acg ccc cct ctg gaa cac agc ccg gcc cac ctc ccc aac cag    96
Glu Asp Thr Pro Pro Leu Glu His Ser Pro Ala His Leu Pro Asn Gln
             20                  25                  30 gcc aat tct ccc cct gtg att gtc aac acg gac acc cta gaa gcc cca   144
Ala Asn Ser Pro Pro Val Ile Val Asn Thr Asp Thr Leu Glu Ala Pro
         35                  40                  45 gga tat gag ttg cag gtg aat gga aca gag ggg gag atg gag tat gag   192
Gly Tyr Glu Leu Gln Val Asn Gly Thr Glu Gly Glu Met Glu Tyr Glu
     50                  55                  60 gag atc aca ttg gaa agg ggt aac tca ggt ctg ggc ttc agc atc gca   240
Glu Ile Thr Leu Glu Arg Gly Asn Ser Gly Leu Gly Phe Ser Ile Ala
 65                  70                  75                  80 ggt ggc act gac aac ccg cac atc ggt gac gac ccg tcc att ttt atc   288
Gly Gly Thr Asp Asn Pro His Ile Gly Asp Asp Pro Ser Ile Phe Ile
                 85                  90                  95 acc aag atc att cct ggt ggg gct gca gcc cag gat ggc cgc ctc agg   336
Thr Lys Ile Ile Pro Gly Gly Ala Ala Ala Gln Asp Gly Arg Leu Arg
            100                 105                 110 gtc aat gac agc atc ctg ttt gta aat gaa gtg gat gtt cgg gag gtg   384
Val Asn Asp Ser Ile Leu Phe Val Asn Glu Val Asp Val Arg Glu Val
        115                 120                 125 acc cat tca gct gcg gtg gag gcc ctc aaa gag gca ggt tcc atc gtt   432
```

```
                Thr His Ser Ala Ala Val Glu Ala Leu Lys Glu Ala Gly Ser Ile Val
                    130                 135                 140 cgc ctc tat gtc atg cgc cgg aaa ccc cca gcc gaa aag gtc atg gag       480
Arg Leu Tyr Val Met Arg Arg Lys Pro Pro Ala Glu Lys Val Met Glu
145                 150                 155                 160 atc aaa ctc atc aaa ggg cct aaa gga ctt ggc ttc agc att gcg ggg       528
Ile Lys Leu Ile Lys Gly Pro Lys Gly Leu Gly Phe Ser Ile Ala Gly
                165                 170                 175 ggc gtt ggg aac cag cac atc cct gga gat aac agc atc tat gta acg       576
Gly Val Gly Asn Gln His Ile Pro Gly Asp Asn Ser Ile Tyr Val Thr
            180                 185                 190 aag atc atc gaa gga ggt gct gcc cac aag gat ggc agg ttg cag att       624
Lys Ile Ile Glu Gly Gly Ala Ala His Lys Asp Gly Arg Leu Gln Ile
        195                 200                 205 gga gac aag atc ctg gcg gtc aac agt gtg ggg ctg gag gac gtc atg       672
Gly Asp Lys Ile Leu Ala Val Asn Ser Val Gly Leu Glu Asp Val Met
210                 215                 220 cac gag gat gcc gtg gca gcc ctg aag aac aca tat gac gtt gtg tac       720
His Glu Asp Ala Val Ala Ala Leu Lys Asn Thr Tyr Asp Val Val Tyr
225                 230                 235                 240 cta aag gtg gcc aag ccc agc aat gcc tac ctg agt gac agc tat gct       768
Leu Lys Val Ala Lys Pro Ser Asn Ala Tyr Leu Ser Asp Ser Tyr Ala
                245                 250                 255 ccc cca gac atc aca acc tcg tat tct cag cac ctg gac aat gag atc       816
Pro Pro Asp Ile Thr Thr Ser Tyr Ser Gln His Leu Asp Asn Glu Ile
            260                 265                 270 agt cat agc agc tac ttg ggc act gac tac ccc aca gcc atg acc ccc       864
Ser His Ser Ser Tyr Leu Gly Thr Asp Tyr Pro Thr Ala Met Thr Pro
        275                 280                 285 act tcc cct cgg cgc tac tcc cct gtg gcc aag gac ctg ctg ggg gag       912
Thr Ser Pro Arg Arg Tyr Ser Pro Val Ala Lys Asp Leu Leu Gly Glu
290                 295                 300 gaa gac att ccc cgg gaa cca agg cgg atc gtg atc cat cgg ggc tcc       960
Glu Asp Ile Pro Arg Glu Pro Arg Arg Ile Val Ile His Arg Gly Ser
305                 310                 315                 320 acc ggc ctg ggc ttc aac atc gtg ggc ggc gag gat ggt gaa ggc atc      1008
Thr Gly Leu Gly Phe Asn Ile Val Gly Gly Glu Asp Gly Glu Gly Ile
                325                 330                 335 ttc atc tcc ttc atc ctt gct ggg ggt cca gcc gac ctc agt ggg gag      1056
Phe Ile Ser Phe Ile Leu Ala Gly Gly Pro Ala Asp Leu Ser Gly Glu
            340                 345                 350 cta cgg aag ggg gac cag atc ctg tcg gtc aat ggt gtt gac ctc cgc      1104
Leu Arg Lys Gly Asp Gln Ile Leu Ser Val Asn Gly Val Asp Leu Arg
        355                 360                 365 aat gcc agt cac gaa cag gct gcc att gcc ctg aag aat gcg ggt cag      1152
Asn Ala Ser His Glu Gln Ala Ala Ile Ala Leu Lys Asn Ala Gly Gln
370                 375                 380 acg gtc acg atc atc gct cag tat aaa cca gaa gag tat agt cga ttc      1200
Thr Val Thr Ile Ile Ala Gln Tyr Lys Pro Glu Glu Tyr Ser Arg Phe
385                 390                 395                 400 gag gcc aag atc cat gat ctt cgg gaa cag ctc atg aat agt agc cta      1248
Glu Ala Lys Ile His Asp Leu Arg Glu Gln Leu Met Asn Ser Ser Leu
                405                 410                 415 ggc tca ggg act gca tcc ttg cga agc aac ccc aag agg ggc ttc tac      1296
Gly Ser Gly Thr Ala Ser Leu Arg Ser Asn Pro Lys Arg Gly Phe Tyr
            420                 425                 430 att agg gcc ctg ttt gat tac gac aag acc aag gac tgc ggt ttc ttg      1344
Ile Arg Ala Leu Phe Asp Tyr Asp Lys Thr Lys Asp Cys Gly Phe Leu
        435                 440                 445 agc cag gcc ctg agc ttc cgc ttc ggg gat gtg ctt cat gtc att gac      1392
Ser Gln Ala Leu Ser Phe Arg Phe Gly Asp Val Leu His Val Ile Asp
```

```
                Ser Gln Ala Leu Ser Phe Arg Phe Gly Asp Val Leu His Val Ile Asp
                    450                 455                 460 gct ggt gac gaa gag tgg tgg caa gca cgg cgg gtc cac tcc gac agt      1440
Ala Gly Asp Glu Glu Trp Trp Gln Ala Arg Arg Val His Ser Asp Ser
465                 470                 475                 480 gag acc gac gac att ggc ttc att ccc agc aaa cgg cgg gtc gag cga      1488
Glu Thr Asp Asp Ile Gly Phe Ile Pro Ser Lys Arg Arg Val Glu Arg
                485                 490                 495 cga gag tgg tca agg tta aag gcc aag gac tgg ggc tcc agc tct gga      1536
Arg Glu Trp Ser Arg Leu Lys Ala Lys Asp Trp Gly Ser Ser Ser Gly
            500                 505                 510 tca cag ggt cga gaa gac tcg gtt ctg agc tat gag acg gtg acc cag      1584
Ser Gln Gly Arg Glu Asp Ser Val Leu Ser Tyr Glu Thr Val Thr Gln
        515                 520                 525 atg gaa gtg cac tat gct cgt ccc atc atc atc ctt gga ccc acc aaa      1632
Met Glu Val His Tyr Ala Arg Pro Ile Ile Ile Leu Gly Pro Thr Lys
    530                 535                 540 gac cgt gcc aac gat gat ctt ctc tcc gag ttc ccc gac aag ttt gga      1680
Asp Arg Ala Asn Asp Asp Leu Leu Ser Glu Phe Pro Asp Lys Phe Gly
545                 550                 555                 560 tcc tgt gtc cct cat acg aca cgt cct aag cgg gaa tat gag ata gac      1728
Ser Cys Val Pro His Thr Thr Arg Pro Lys Arg Glu Tyr Glu Ile Asp
                565                 570                 575 ggc cgg gat tac cac ttt gtc tcc tcc cgg gag aaa atg gag aag gac      1776
Gly Arg Asp Tyr His Phe Val Ser Ser Arg Glu Lys Met Glu Lys Asp
            580                 585                 590 atc cag gca cac aag ttc att gag gct ggc cag tac aac agc cac ctc      1824
Ile Gln Ala His Lys Phe Ile Glu Ala Gly Gln Tyr Asn Ser His Leu
        595                 600                 605 tat ggg acc agc gtc cag tct gtg cga gag gta gca gag cag ggg aag      1872
Tyr Gly Thr Ser Val Gln Ser Val Arg Glu Val Ala Glu Gln Gly Lys
    610                 615                 620 cac tgc atc ctc gat gtc tcg gcc aat gcc gtg cgg cgg ctg cag gcg      1920
His Cys Ile Leu Asp Val Ser Ala Asn Ala Val Arg Arg Leu Gln Ala
625                 630                 635                 640 gcc cac ctg cac ccc atc gcc atc ttc atc cgt ccc cgc tcc ctg gag      1968
Ala His Leu His Pro Ile Ala Ile Phe Ile Arg Pro Arg Ser Leu Glu
                645                 650                 655 aat gtg cta gag atc aat aag cgg atc aca gag gag caa gcc cgg aaa      2016
Asn Val Leu Glu Ile Asn Lys Arg Ile Thr Glu Glu Gln Ala Arg Lys
            660                 665                 670 gcc ttc gac aga gcc acg aag ctg gag cag gag ttc aca gag tgc ttc      2064
Ala Phe Asp Arg Ala Thr Lys Leu Glu Gln Glu Phe Thr Glu Cys Phe
        675                 680                 685 tca gcc atc gta gag ggc gac agc ttt gaa gag atc tat cac aaa gtg      2112
Ser Ala Ile Val Glu Gly Asp Ser Phe Glu Glu Ile Tyr His Lys Val
    690                 695                 700 aaa cgt gtc att gaa gac ctc tca ggc ccc tac atc tgg gtc cca gcc      2160
Lys Arg Val Ile Glu Asp Leu Ser Gly Pro Tyr Ile Trp Val Pro Ala
705                 710                 715                 720 cga gag aga ctc tcc aat tcg gtc cgg cgg gag cgg atc cgg cgg cca      2208
Arg Glu Arg Leu Ser Asn Ser Val Arg Arg Glu Arg Ile Arg Arg Pro
                725                 730                 735 gtc ccc gcg ggc ccc acc atg agc aag ggc gag gag ctg ttc acc ggg      2256
Val Pro Ala Gly Pro Thr Met Ser Lys Gly Glu Glu Leu Phe Thr Gly
            740                 745                 750 gtg gtg ccc atc ctg gtc gag ctg gac ggc gac gta aac ggc cac aag      2304
Val Val Pro Ile Leu Val Glu Leu Asp Gly Asp Val Asn Gly His Lys
        755                 760                 765 ttc agc gtg tcc ggc gag ggc gag ggc gat gcc acc tac ggc aag ctg      2352
```

-continued

| | | |
|---|---|---|
| Phe Ser Val Ser Gly Glu Gly Glu Gly Asp Ala Thr Tyr Gly Lys Leu<br>770                        775                        780 | |
| acc ctg aag ttc atc tgc acc acc ggc aag ctg ccc gtg ccc tgg ccc<br>Thr Leu Lys Phe Ile Cys Thr Thr Gly Lys Leu Pro Val Pro Trp Pro<br>785                        790                        795                        800 | 2400 |
| acc ctc gtg acc acc ctg acc tac ggc gtg cag tgc ttc agc cgc tac<br>Thr Leu Val Thr Thr Leu Thr Tyr Gly Val Gln Cys Phe Ser Arg Tyr<br>805                        810                        815 | 2448 |
| ccc gac cac atg aag cag cac gac ttc ttc aag tcc gcc atg ccc gaa<br>Pro Asp His Met Lys Gln His Asp Phe Phe Lys Ser Ala Met Pro Glu<br>820                        825                        830 | 2496 |
| ggc tac gtc cag gag cgc acc atc ttc ttc aag gac gac ggc aac tac<br>Gly Tyr Val Gln Glu Arg Thr Ile Phe Phe Lys Asp Asp Gly Asn Tyr<br>835                        840                        845 | 2544 |
| aag acc cgc gcc gag gtg aag ttc gag ggc gac acc ctg gtg aac cgc<br>Lys Thr Arg Ala Glu Val Lys Phe Glu Gly Asp Thr Leu Val Asn Arg<br>850                        855                        860 | 2592 |
| atc gag ctg aag ggc atc gac ttc aag gag gac ggc aac atc ctg ggg<br>Ile Glu Leu Lys Gly Ile Asp Phe Lys Glu Asp Gly Asn Ile Leu Gly<br>865                        870                        875                        880 | 2640 |
| cac aag ctg gag tac aac tac aac agc cac aac gtc tat atc atg gcc<br>His Lys Leu Glu Tyr Asn Tyr Asn Ser His Asn Val Tyr Ile Met Ala<br>885                        890                        895 | 2688 |
| gac aag cag aag aac ggc atc aag gcc aac ttc aag atc cgc cac aac<br>Asp Lys Gln Lys Asn Gly Ile Lys Ala Asn Phe Lys Ile Arg His Asn<br>900                        905                        910 | 2736 |
| atc gag gac ggc agc gtg cag ctc gcc gac cac tac cag cag aac acc<br>Ile Glu Asp Gly Ser Val Gln Leu Ala Asp His Tyr Gln Gln Asn Thr<br>915                        920                        925 | 2784 |
| ccc atc ggc gac ggc ccc gtg ctg ctg ccc gac aac cac tac ctg agc<br>Pro Ile Gly Asp Gly Pro Val Leu Leu Pro Asp Asn His Tyr Leu Ser<br>930                        935                        940 | 2832 |
| acc cag tcc gcc ctg agc aaa gac ccc aac gag aag cgc gat cac atg<br>Thr Gln Ser Ala Leu Ser Lys Asp Pro Asn Glu Lys Arg Asp His Met<br>945                        950                        955                        960 | 2880 |
| gtc ctg ctg gag ttc gtg acc gcc gcc ggg atc act cac ggc atg gac<br>Val Leu Leu Glu Phe Val Thr Ala Ala Gly Ile Thr His Gly Met Asp<br>965                        970                        975 | 2928 |
| gag ctg tac aag tcc ggc ggg agc gga tcc ggc ggc cag tcc ggc ggg<br>Glu Leu Tyr Lys Ser Gly Gly Ser Gly Ser Gly Gly Gln Ser Gly Gly<br>980                        985                        990 | 2976 |
| agc gga tcc ggc ggc cag tcc ggc ggg agc gga tcc ggc ggc cag tcc<br>Ser Gly Ser Gly Gly Gln Ser Gly Gly Ser Gly Ser Gly Gly Gln Ser<br>995                        1000                       1005 | 3024 |
| ggc ggg agc gga tcc ggc ggc cag tcc ggc ggg agc gga tcc ggc ggc<br>Gly Gly Ser Gly Ser Gly Gly Gln Ser Gly Gly Ser Gly Ser Gly Gly<br>1010                      1015                      1020 | 3072 |
| cag tcc gga ctc aga tct gtc aaa ctt aca tca gac ttc gac aac cca<br>Gln Ser Gly Leu Arg Ser Val Lys Leu Thr Ser Asp Phe Asp Asn Pro<br>1025                      1030                      1035                      1040 | 3120 |
| aga tgg att gga cga cac aag cat atg ttc aat ttc ctt gat gtc aac<br>Arg Trp Ile Gly Arg His Lys His Met Phe Asn Phe Leu Asp Val Asn<br>                                    1045                      1050                      1055 | 3168 |
| cac aat gga aaa atc tct ctt gac gag atg gtc tac aag gca tct gat<br>His Asn Gly Lys Ile Ser Leu Asp Glu Met Val Tyr Lys Ala Ser Asp<br>                                    1060                      1065                      1070 | 3216 |
| att gtc atc aat aac ctt gga gca aca cct gag caa gcc aaa cga cac<br>Ile Val Ile Asn Asn Leu Gly Ala Thr Pro Glu Gln Ala Lys Arg His<br>1075                      1080                      1085 | 3264 |
| aaa gat gct gtg gaa gcc ttc ttc gga gga gct gga atg aaa tat ggt | 3312 |

-continued

```
Lys Asp Ala Val Glu Ala Phe Phe Gly Gly Ala Gly Met Lys Tyr Gly
    1090                1095                1100 gtg gaa act gat tgg cct gca tat att gaa gga tgg aaa aaa ttg gct    3360
Val Glu Thr Asp Trp Pro Ala Tyr Ile Glu Gly Trp Lys Lys Leu Ala
1105                1110                1115                1120 act gat gaa ttg gag aaa tac gcc aaa aac gaa cca acc ctc atc cgc    3408
Thr Asp Glu Leu Glu Lys Tyr Ala Lys Asn Glu Pro Thr Leu Ile Arg
            1125                1130                1135 atc tgg ggt gat gct ttg ttt gat atc gtt gac aaa gat caa aat gga    3456
Ile Trp Gly Asp Ala Leu Phe Asp Ile Val Asp Lys Asp Gln Asn Gly
        1140                1145                1150 gct att aca ctg gat gaa tgg aaa gca tac acc aaa gct gct ggt atc    3504
Ala Ile Thr Leu Asp Glu Trp Lys Ala Tyr Thr Lys Ala Ala Gly Ile
    1155                1160                1165 atc caa tca tca gaa gat tgc gag gaa aca ttc aga gtg tgc gat att    3552
Ile Gln Ser Ser Glu Asp Cys Glu Glu Thr Phe Arg Val Cys Asp Ile
1170                1175                1180 gat gaa agt gga caa ctc gat gtt gat gag atg aca aga cag cat ctg    3600
Asp Glu Ser Gly Gln Leu Asp Val Asp Glu Met Thr Arg Gln His Leu
1185                1190                1195                1200 gga ttt tgg tac acc atg gat cct gct tgc gaa aag ctc tac ggt gga    3648
Gly Phe Trp Tyr Thr Met Asp Pro Ala Cys Glu Lys Leu Tyr Gly Gly
            1205                1210                1215 gct gtc ccc taa                                                    3660
Ala Val Pro <210> SEQ ID NO 4
<211> LENGTH: 1219
<212> TYPE: PRT
<213> ORGANISM: Artificial Sequence
<220> FEATURE:
<223> OTHER INFORMATION: Description of Artificial Sequence: Synthetic
      coding sequence contained in PSDGA vector

<400> SEQUENCE: 4

Met Asp Cys Leu Cys Ile Val Thr Thr Lys Lys Tyr Arg Tyr Gln Asp
1               5                   10                  15

Glu Asp Thr Pro Pro Leu Glu His Ser Pro Ala His Leu Pro Asn Gln
            20                  25                  30

Ala Asn Ser Pro Pro Val Ile Val Asn Thr Asp Thr Leu Glu Ala Pro
        35                  40                  45

Gly Tyr Glu Leu Gln Val Asn Gly Thr Glu Gly Glu Met Glu Tyr Glu
    50                  55                  60

Glu Ile Thr Leu Glu Arg Gly Asn Ser Gly Leu Gly Phe Ser Ile Ala
65                  70                  75                  80

Gly Gly Thr Asp Asn Pro His Ile Gly Asp Asp Pro Ser Ile Phe Ile
                85                  90                  95

Thr Lys Ile Ile Pro Gly Gly Ala Ala Ala Gln Asp Gly Arg Leu Arg
            100                 105                 110

Val Asn Asp Ser Ile Leu Phe Val Asn Glu Val Asp Val Arg Glu Val
        115                 120                 125

Thr His Ser Ala Ala Val Glu Ala Leu Lys Glu Ala Gly Ser Ile Val
    130                 135                 140

Arg Leu Tyr Val Met Arg Arg Lys Pro Pro Ala Glu Lys Val Met Glu
145                 150                 155                 160

Ile Lys Leu Ile Lys Gly Pro Lys Gly Leu Gly Phe Ser Ile Ala Gly
                165                 170                 175

Gly Val Gly Asn Gln His Ile Pro Gly Asp Asn Ser Ile Tyr Val Thr
            180                 185                 190
```

```
Lys Ile Ile Glu Gly Ala Ala His Lys Asp Gly Arg Leu Gln Ile
    195                 200                 205
Gly Asp Lys Ile Leu Ala Val Asn Ser Val Gly Leu Glu Asp Val Met
210                 215                 220
His Glu Asp Ala Val Ala Leu Lys Asn Thr Tyr Asp Val Val Tyr
225                 230                 235                 240
Leu Lys Val Ala Lys Pro Ser Asn Ala Tyr Leu Ser Asp Ser Tyr Ala
                245                 250                 255
Pro Pro Asp Ile Thr Thr Ser Tyr Ser Gln His Leu Asp Asn Glu Ile
            260                 265                 270
Ser His Ser Ser Tyr Leu Gly Thr Asp Tyr Pro Thr Ala Met Thr Pro
    275                 280                 285
Thr Ser Pro Arg Arg Tyr Ser Pro Val Ala Lys Asp Leu Leu Gly Glu
    290                 295                 300
Glu Asp Ile Pro Arg Glu Pro Arg Arg Ile Val Ile His Arg Gly Ser
305                 310                 315                 320
Thr Gly Leu Gly Phe Asn Ile Val Gly Gly Glu Asp Gly Glu Gly Ile
                325                 330                 335
Phe Ile Ser Phe Ile Leu Ala Gly Gly Pro Ala Asp Leu Ser Gly Glu
                340                 345                 350
Leu Arg Lys Gly Asp Gln Ile Leu Ser Val Asn Gly Val Asp Leu Arg
    355                 360                 365
Asn Ala Ser His Glu Gln Ala Ala Ile Ala Leu Lys Asn Ala Gly Gln
    370                 375                 380
Thr Val Thr Ile Ile Ala Gln Tyr Lys Pro Glu Glu Tyr Ser Arg Phe
385                 390                 395                 400
Glu Ala Lys Ile His Asp Leu Arg Glu Gln Leu Met Asn Ser Ser Leu
                405                 410                 415
Gly Ser Gly Thr Ala Ser Leu Arg Ser Asn Pro Lys Arg Gly Phe Tyr
                420                 425                 430
Ile Arg Ala Leu Phe Asp Tyr Asp Lys Thr Lys Asp Cys Gly Phe Leu
                435                 440                 445
Ser Gln Ala Leu Ser Phe Arg Phe Gly Asp Val Leu His Val Ile Asp
    450                 455                 460
Ala Gly Asp Glu Glu Trp Trp Gln Ala Arg Arg Val His Ser Asp Ser
465                 470                 475                 480
Glu Thr Asp Asp Ile Gly Phe Ile Pro Ser Lys Arg Arg Val Glu Arg
                485                 490                 495
Arg Glu Trp Ser Arg Leu Lys Ala Lys Asp Trp Gly Ser Ser Ser Gly
                500                 505                 510
Ser Gln Gly Arg Glu Asp Ser Val Leu Ser Tyr Glu Thr Val Thr Gln
    515                 520                 525
Met Glu Val His Tyr Ala Arg Pro Ile Ile Ile Leu Gly Pro Thr Lys
    530                 535                 540
Asp Arg Ala Asn Asp Asp Leu Leu Ser Glu Phe Pro Asp Lys Phe Gly
545                 550                 555                 560
Ser Cys Val Pro His Thr Thr Arg Pro Lys Arg Glu Tyr Glu Ile Asp
                565                 570                 575
Gly Arg Asp Tyr His Phe Val Ser Ser Arg Glu Lys Met Glu Lys Asp
                580                 585                 590
Ile Gln Ala His Lys Phe Ile Glu Ala Gly Gln Tyr Asn Ser His Leu
    595                 600                 605
Tyr Gly Thr Ser Val Gln Ser Val Arg Glu Val Ala Glu Gln Gly Lys
```

-continued

```
            610                 615                 620
His Cys Ile Leu Asp Val Ser Ala Asn Ala Val Arg Arg Leu Gln Ala
625                 630                 635                 640

Ala His Leu His Pro Ile Ala Ile Phe Ile Arg Pro Arg Ser Leu Glu
            645                 650                 655

Asn Val Leu Glu Ile Asn Lys Arg Ile Thr Glu Gln Ala Arg Lys
            660                 665                 670

Ala Phe Asp Arg Ala Thr Lys Leu Glu Gln Phe Thr Glu Cys Phe
            675                 680                 685

Ser Ala Ile Val Glu Gly Asp Ser Phe Glu Ile Tyr His Lys Val
690                 695                 700

Lys Arg Val Ile Glu Asp Leu Ser Gly Pro Tyr Ile Trp Val Pro Ala
705                 710                 715                 720

Arg Glu Arg Leu Ser Asn Ser Val Arg Glu Arg Ile Arg Arg Pro
            725                 730                 735

Val Pro Ala Gly Pro Thr Met Ser Lys Gly Glu Glu Leu Phe Thr Gly
            740                 745                 750

Val Val Pro Ile Leu Val Glu Leu Asp Gly Asp Val Asn Gly His Lys
            755                 760                 765

Phe Ser Val Ser Gly Glu Gly Glu Gly Asp Ala Thr Tyr Gly Lys Leu
770                 775                 780

Thr Leu Lys Phe Ile Cys Thr Thr Gly Lys Leu Pro Val Pro Trp Pro
785                 790                 795                 800

Thr Leu Val Thr Thr Leu Thr Tyr Gly Val Gln Cys Phe Ser Arg Tyr
            805                 810                 815

Pro Asp His Met Lys Gln His Asp Phe Phe Lys Ser Ala Met Pro Glu
            820                 825                 830

Gly Tyr Val Gln Glu Arg Thr Ile Phe Phe Lys Asp Asp Gly Asn Tyr
            835                 840                 845

Lys Thr Arg Ala Glu Val Lys Phe Glu Gly Asp Thr Leu Val Asn Arg
850                 855                 860

Ile Glu Leu Lys Gly Ile Asp Phe Lys Glu Asp Gly Asn Ile Leu Gly
865                 870                 875                 880

His Lys Leu Glu Tyr Asn Tyr Asn Ser His Asn Val Tyr Ile Met Ala
            885                 890                 895

Asp Lys Gln Lys Asn Gly Ile Lys Ala Asn Phe Lys Ile Arg His Asn
            900                 905                 910

Ile Glu Asp Gly Ser Val Gln Leu Ala Asp His Tyr Gln Gln Asn Thr
            915                 920                 925

Pro Ile Gly Asp Gly Pro Val Leu Leu Pro Asp Asn His Tyr Leu Ser
            930                 935                 940

Thr Gln Ser Ala Leu Ser Lys Asp Pro Asn Glu Lys Arg Asp His Met
945                 950                 955                 960

Val Leu Leu Glu Phe Val Thr Ala Ala Gly Ile Thr His Gly Met Asp
            965                 970                 975

Glu Leu Tyr Lys Ser Gly Gly Ser Gly Gly Gln Ser Gly Gly
            980                 985                 990

Ser Gly Ser Gly Gly Gln Ser Gly Gly Ser Gly Gly Gln Ser
            995                 1000                1005

Gly Gly Ser Gly Ser Gly Gly Gln Ser Gly Gly Ser Gly Gly Gly
    1010                1015                1020

Gln Ser Gly Leu Arg Ser Val Lys Leu Thr Ser Asp Phe Asp Asn Pro
1025                1030                1035                1040
```

```
Arg Trp Ile Gly Arg His Lys His Met Phe Asn Phe Leu Asp Val Asn
            1045                1050                1055

His Asn Gly Lys Ile Ser Leu Asp Glu Met Val Tyr Lys Ala Ser Asp
        1060                1065                1070

Ile Val Ile Asn Asn Leu Gly Ala Thr Pro Glu Gln Ala Lys Arg His
    1075                1080                1085

Lys Asp Ala Val Glu Ala Phe Phe Gly Gly Ala Gly Met Lys Tyr Gly
    1090                1095                1100

Val Glu Thr Asp Trp Pro Ala Tyr Ile Glu Gly Trp Lys Lys Leu Ala
1105                1110                1115                1120

Thr Asp Glu Leu Glu Lys Tyr Ala Lys Asn Gly Pro Thr Leu Ile Arg
            1125                1130                1135

Ile Trp Gly Asp Ala Leu Phe Asp Ile Val Asp Lys Asp Gln Asn Gly
        1140                1145                1150

Ala Ile Thr Leu Asp Glu Trp Lys Ala Tyr Thr Lys Ala Ala Gly Ile
    1155                1160                1165

Ile Gln Ser Ser Glu Asp Cys Glu Glu Thr Phe Arg Val Cys Asp Ile
    1170                1175                1180

Asp Glu Ser Gly Gln Leu Asp Val Asp Glu Met Thr Arg Gln His Leu
1185                1190                1195                1200

Gly Phe Trp Tyr Thr Met Asp Pro Ala Cys Glu Lys Leu Tyr Gly Gly
            1205                1210                1215

Ala Val Pro

<210> SEQ ID NO 5
<211> LENGTH: 1539
<212> TYPE: DNA
<213> ORGANISM: Artificial Sequence
<220> FEATURE:
<223> OTHER INFORMATION: Description of Artificial Sequence: Synthetic
      coding sequence contained in mtGA vector
<220> FEATURE:
<221> NAME/KEY: CDS
<222> LOCATION: (1)..(1536)

<400> SEQUENCE: 5 atg tcc gtc ctg acg ccg ctg ctg ctg cgg ggc ttg aca ggc tcg gcc      48
Met Ser Val Leu Thr Pro Leu Leu Leu Arg Gly Leu Thr Gly Ser Ala
1               5                   10                  15 cgg cgg ctc cca gtg ccg cgc gcc aag atc cat tcg ttg ctg cag ccg      96
Arg Arg Leu Pro Val Pro Arg Ala Lys Ile His Ser Leu Leu Gln Pro
            20                  25                  30 cgg gcc acc atg agc aag ggc gag gag ctg ttc acc ggg gtg gtg ccc     144
Arg Ala Thr Met Ser Lys Gly Glu Glu Leu Phe Thr Gly Val Val Pro
        35                  40                  45 atc ctg gtc gag ctg gac ggc gac gta aac ggc cac aag ttc agc gtg     192
Ile Leu Val Glu Leu Asp Gly Asp Val Asn Gly His Lys Phe Ser Val
    50                  55                  60 tcc ggc gag ggc gag ggc gat gcc acc tac ggc aag ctg acc ctg aag     240
Ser Gly Glu Gly Glu Gly Asp Ala Thr Tyr Gly Lys Leu Thr Leu Lys
65                  70                  75                  80 ttc atc tgc acc acc ggc aag ctg ccc gtg ccc tgg ccc acc ctc gtg     288
Phe Ile Cys Thr Thr Gly Lys Leu Pro Val Pro Trp Pro Thr Leu Val
                85                  90                  95 acc acc ctg acc tac ggc gtg cag tgc ttc agc cgc tac ccc gac cac     336
Thr Thr Leu Thr Tyr Gly Val Gln Cys Phe Ser Arg Tyr Pro Asp His
            100                 105                 110 atg aag cag cac gac ttc ttc aag tcc gcc atg ccc gaa ggc tac gtc     384
Met Lys Gln His Asp Phe Phe Lys Ser Ala Met Pro Glu Gly Tyr Val
        115                 120                 125
```

```
cag gag cgc acc atc ttc ttc aag gac gac ggc aac tac aag acc cgc      432
Gln Glu Arg Thr Ile Phe Phe Lys Asp Asp Gly Asn Tyr Lys Thr Arg
    130                 135                 140 gcc gag gtg aag ttc gag ggc gac acc ctg gtg aac cgc atc gag ctg      480
Ala Glu Val Lys Phe Glu Gly Asp Thr Leu Val Asn Arg Ile Glu Leu
145                 150                 155                 160 aag ggc atc gac ttc aag gag gac ggc aac atc ctg ggg cac aag ctg      528
Lys Gly Ile Asp Phe Lys Glu Asp Gly Asn Ile Leu Gly His Lys Leu
                165                 170                 175 gag tac aac tac aac agc cac aac gtc tat atc atg gcc gac aag cag      576
Glu Tyr Asn Tyr Asn Ser His Asn Val Tyr Ile Met Ala Asp Lys Gln
            180                 185                 190 aag aac ggc atc aag gcc aac ttc aag atc cgc cac aac atc gag gac      624
Lys Asn Gly Ile Lys Ala Asn Phe Lys Ile Arg His Asn Ile Glu Asp
        195                 200                 205 ggc agc gtg cag ctc gcc gac cac tac cag cag aac acc ccc atc ggc      672
Gly Ser Val Gln Leu Ala Asp His Tyr Gln Gln Asn Thr Pro Ile Gly
    210                 215                 220 gac ggc ccc gtg ctg ctg ccc gac aac cac tac ctg agc acc cag tcc      720
Asp Gly Pro Val Leu Leu Pro Asp Asn His Tyr Leu Ser Thr Gln Ser
225                 230                 235                 240 gcc ctg agc aaa gac ccc aac gag aag cgc gat cac atg gtc ctg ctg      768
Ala Leu Ser Lys Asp Pro Asn Glu Lys Arg Asp His Met Val Leu Leu
                245                 250                 255 gag ttc gtg acc gcc gcc ggg atc act cac ggc atg gac gag ctg tac      816
Glu Phe Val Thr Ala Ala Gly Ile Thr His Gly Met Asp Glu Leu Tyr
                260                 265                 270 aag tcc ggc ggg agc gga tcc ggc ggc cag tcc ggc ggg agc gga tcc      864
Lys Ser Gly Gly Ser Gly Ser Gly Gly Gln Ser Gly Gly Ser Gly Ser
            275                 280                 285 ggc ggc cag tcc ggc ggg agc gga tcc ggc ggc cag tcc ggc ggg agc      912
Gly Gly Gln Ser Gly Gly Ser Gly Ser Gly Gly Gln Ser Gly Gly Ser
        290                 295                 300 gga tcc ggc ggc cag tcc ggc ggg agc gga tcc ggc ggc cag tcc gga      960
Gly Ser Gly Gly Gln Ser Gly Gly Ser Gly Ser Gly Gly Gln Ser Gly
305                 310                 315                 320 ctc aga tct gtc aaa ctt aca tca gac ttc gac aac cca aga tgg att     1008
Leu Arg Ser Val Lys Leu Thr Ser Asp Phe Asp Asn Pro Arg Trp Ile
                325                 330                 335 gga cga cac aag cat atg ttc aat ttc ctt gat gtc aac cac aat gga     1056
Gly Arg His Lys His Met Phe Asn Phe Leu Asp Val Asn His Asn Gly
                340                 345                 350 aaa atc tct ctt gac gag atg gtc tac aag gca tct gat att gtc atc     1104
Lys Ile Ser Leu Asp Glu Met Val Tyr Lys Ala Ser Asp Ile Val Ile
            355                 360                 365 aat aac ctt gga gca aca cct gag caa gcc aaa cga cac aaa gat gct     1152
Asn Asn Leu Gly Ala Thr Pro Glu Gln Ala Lys Arg His Lys Asp Ala
        370                 375                 380 gtg gaa gcc ttc ttc gga gga gct gga atg aaa tat ggt gtg gaa act     1200
Val Glu Ala Phe Phe Gly Gly Ala Gly Met Lys Tyr Gly Val Glu Thr
385                 390                 395                 400 gat tgg cct gca tat att gaa gga tgg aaa aaa ttg gct act gat gaa     1248
Asp Trp Pro Ala Tyr Ile Glu Gly Trp Lys Lys Leu Ala Thr Asp Glu
                405                 410                 415 ttg gag aaa tac gcc aaa aac gaa cca acc ctc atc cgc atc tgg ggt     1296
Leu Glu Lys Tyr Ala Lys Asn Glu Pro Thr Leu Ile Arg Ile Trp Gly
                420                 425                 430 gat gct ttg ttt gat atc gtt gac aaa gat caa aat gga gct att aca     1344
Asp Ala Leu Phe Asp Ile Val Asp Lys Asp Gln Asn Gly Ala Ile Thr
            435                 440                 445
```

| | | | | | | | | | | | | | | | |
|---|---|---|---|---|---|---|---|---|---|---|---|---|---|---|---|
| ctg | gat | gaa | tgg | aaa | gca | tac | acc | aaa | gct | gct | ggt | atc | atc | caa | tca | 1392 |
| Leu | Asp | Glu | Trp | Lys | Ala | Tyr | Thr | Lys | Ala | Ala | Gly | Ile | Ile | Gln | Ser | |
| | 450 | | | | | 455 | | | | | 460 | | | | | |
| tca | gaa | gat | tgc | gag | gaa | aca | ttc | aga | gtg | tgc | gat | att | gat | gaa | agt | 1440 |
| Ser | Glu | Asp | Cys | Glu | Glu | Thr | Phe | Arg | Val | Cys | Asp | Ile | Asp | Glu | Ser | |
| 465 | | | | | 470 | | | | | 475 | | | | | 480 | |
| gga | caa | ctc | gat | gtt | gat | gag | atg | aca | aga | cag | cat | ctg | gga | ttt | tgg | 1488 |
| Gly | Gln | Leu | Asp | Val | Asp | Glu | Met | Thr | Arg | Gln | His | Leu | Gly | Phe | Trp | |
| | | | | 485 | | | | | 490 | | | | | 495 | | |
| tac | acc | atg | gat | cct | gct | tgc | gaa | aag | ctc | tac | ggt | gga | gct | gtc | ccc | 1536 |
| Tyr | Thr | Met | Asp | Pro | Ala | Cys | Glu | Lys | Leu | Tyr | Gly | Gly | Ala | Val | Pro | |
| | | | 500 | | | | | 505 | | | | | 510 | | | |
| taa | | | | | | | | | | | | | | | | 1539 |

<210> SEQ ID NO 6
<211> LENGTH: 512
<212> TYPE: PRT
<213> ORGANISM: Artificial Sequence
<220> FEATURE:
<223> OTHER INFORMATION: Description of Artificial Sequence: Synthetic
      coding sequence contained in mtGA vector

<400> SEQUENCE: 6

Met Ser Val Leu Thr Pro Leu Leu Arg Gly Leu Thr Gly Ser Ala
 1               5                  10                  15

Arg Arg Leu Pro Val Pro Arg Ala Lys Ile His Ser Leu Leu Gln Pro
                20                  25                  30

Arg Ala Thr Met Ser Lys Gly Glu Glu Leu Phe Thr Gly Val Val Pro
            35                  40                  45

Ile Leu Val Glu Leu Asp Gly Asp Val Asn Gly His Lys Phe Ser Val
        50                  55                  60

Ser Gly Glu Gly Glu Gly Asp Ala Thr Tyr Gly Lys Leu Thr Leu Lys
65                  70                  75                  80

Phe Ile Cys Thr Thr Gly Lys Leu Pro Val Pro Trp Pro Thr Leu Val
                85                  90                  95

Thr Thr Leu Thr Tyr Gly Val Gln Cys Phe Ser Arg Tyr Pro Asp His
            100                 105                 110

Met Lys Gln His Asp Phe Phe Lys Ser Ala Met Pro Glu Gly Tyr Val
        115                 120                 125

Gln Glu Arg Thr Ile Phe Phe Lys Asp Asp Gly Asn Tyr Lys Thr Arg
    130                 135                 140

Ala Glu Val Lys Phe Glu Gly Asp Thr Leu Val Asn Arg Ile Glu Leu
145                 150                 155                 160

Lys Gly Ile Asp Phe Lys Glu Asp Gly Asn Ile Leu Gly His Lys Leu
                165                 170                 175

Glu Tyr Asn Tyr Asn Ser His Asn Val Tyr Ile Met Ala Asp Lys Gln
            180                 185                 190

Lys Asn Gly Ile Lys Ala Asn Phe Lys Ile Arg His Asn Ile Glu Asp
        195                 200                 205

Gly Ser Val Gln Leu Ala Asp His Tyr Gln Gln Asn Thr Pro Ile Gly
    210                 215                 220

Asp Gly Pro Val Leu Leu Pro Asp Asn His Tyr Leu Ser Thr Gln Ser
225                 230                 235                 240

Ala Leu Ser Lys Asp Pro Asn Glu Lys Arg Asp His Met Val Leu Leu
                245                 250                 255

Glu Phe Val Thr Ala Ala Gly Ile Thr His Gly Met Asp Glu Leu Tyr
            260                 265                 270

```
Lys Ser Gly Gly Ser Gly Ser Gly Gly Gln Ser Gly Gly Ser Gly Ser
            275                 280                 285
Gly Gly Gln Ser Gly Gly Ser Gly Ser Gly Gly Gln Ser Gly Gly Ser
            290                 295                 300
Gly Ser Gly Gly Gln Ser Gly Gly Ser Gly Ser Gly Gly Gln Ser Gly
305                 310                 315                 320
Leu Arg Ser Val Lys Leu Thr Ser Asp Phe Asp Asn Pro Arg Trp Ile
            325                 330                 335
Gly Arg His Lys His Met Phe Asn Phe Leu Asp Val Asn His Asn Gly
            340                 345                 350
Lys Ile Ser Leu Asp Glu Met Val Tyr Lys Ala Ser Asp Ile Val Ile
            355                 360                 365
Asn Asn Leu Gly Ala Thr Pro Glu Gln Ala Lys Arg His Lys Asp Ala
            370                 375                 380
Val Glu Ala Phe Phe Gly Gly Ala Gly Met Lys Tyr Gly Val Glu Thr
385                 390                 395                 400
Asp Trp Pro Ala Tyr Ile Glu Gly Trp Lys Lys Leu Ala Thr Asp Glu
            405                 410                 415
Leu Glu Lys Tyr Ala Lys Asn Glu Pro Thr Leu Ile Arg Ile Trp Gly
            420                 425                 430
Asp Ala Leu Phe Asp Ile Val Asp Lys Asp Gln Asn Gly Ala Ile Thr
            435                 440                 445
Leu Asp Glu Trp Lys Ala Tyr Thr Lys Ala Ala Gly Ile Ile Gln Ser
            450                 455                 460
Ser Glu Asp Cys Glu Glu Thr Phe Arg Val Cys Asp Ile Asp Glu Ser
465                 470                 475                 480
Gly Gln Leu Asp Val Asp Glu Met Thr Arg Gln His Leu Gly Phe Trp
            485                 490                 495
Tyr Thr Met Asp Pro Ala Cys Glu Lys Leu Tyr Gly Gly Ala Val Pro
            500                 505                 510

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 7

Ser Gly Leu Arg Ser
 1               5
```